United States Patent [19]
Dean et al.

[11] Patent Number: 6,136,603
[45] Date of Patent: Oct. 24, 2000

[54] ANTISENSE MODULATION OF INTERLEUKIN-5 SIGNAL TRANSDUCTION

[75] Inventors: Nicholas M. Dean, Olivenhain; James G. Karras, San Marcos; Robert McKay, San Diego, all of Calif.

[73] Assignee: Isis Pharmaceuticals Inc., Carlsbad, Calif.

[21] Appl. No.: 09/280,799

[22] Filed: Mar. 26, 1999

[51] Int. Cl.⁷ .............................. C07H 21/04; C12Q 1/68; C12N 15/85
[52] U.S. Cl. .............................. 435/375; 435/6; 435/91.1; 435/366; 536/23.1; 536/24.31; 536/24.33; 536/24.5
[58] Field of Search .............................. 435/6, 91.1, 375; 536/24.5, 24.1, 24.3; 514/44

[56] References Cited

U.S. PATENT DOCUMENTS

| | | | |
|---|---|---|---|
| 5,616,490 | 4/1997 | Sullivan et al. | 435/366 |
| 5,821,091 | 10/1998 | Dolganov | 435/91.2 |

FOREIGN PATENT DOCUMENTS

| | | |
|---|---|---|
| WO 95/23225 | 8/1995 | WIPO . |
| WO 96/40162 | 12/1996 | WIPO . |
| 97/27284 | 7/1997 | WIPO . |
| 98/38306 | 9/1998 | WIPO . |

OTHER PUBLICATIONS

Branch TIBS 23 pp. 45–50, Feb. 1998.
Flanagan et al., Nature Biotech. 17: 48–52, Jan. 1999.
Milner et al., Nature Biotech. 15: 537–541, Jun. 1997.

Imamura, et al., "The Murine Interleukin–5 Receptor α–Subunit Gene: Characterization of the Gene Structure and Chromosome Mapping", *DNA Cell Biol*, 1994 13:283–292.

Tavernier et al., "Molecular basis of the membrane–anchored and two soluble isoforms of the human interleukin 5 receptor αto subunit", *Proc.Natl.Acad.Sci. USA*, 1992 89: 7041045.

Tuypens et al., "Organization and chromosomal localization of the human interleukin 5 receptor α–chain gene", *Eur.Cytokine Netw.*, 1992, 3:451–459.

Weltman and Karim, "Interleukin–5: A Proeosinophil Cytokine Mediator of Inflammation in Asthma and a Target for Antisense Therapy", *Allergy Asthma Proc.*, 1998, 19: 257–261.

*Primary Examiner*—George C. Elliott
*Assistant Examiner*—Melissa Schmidt
*Attorney, Agent, or Firm*—Law Offices of Jane Massey Licata

[57] ABSTRACT

Compositions and methods are provided for antisense modulation of interleukin-5 signal transduction. Antisense compounds, particularly antisense oligonucleotides, targeted to nucleic acids encoding interleukin-5 and interleukin-5 receptorα are preferred. Methods of using these compounds for modulation of interleukin-5 signal transduction and for treatment of diseases associated with interleukin-5 signal transduction are also provided.

32 Claims, No Drawings

SEQUENCE LISTING

<160> NUMBER OF SEQ ID NOS: 208

<210> SEQ ID NO 1
<211> LENGTH: 6727
<212> TYPE: DNA
<213> ORGANISM: Mus musculus

<400> SEQUENCE: 1

| | | | | | |
|---|---|---|---|---|---|
| tgtacctccc | acatctgctg | gtgtgtacca | ccacacctag | taagatattc | tcaacattta | 60 |
| tgtattttag | cctaaccctg | ttggaggtat | acatttgaat | acattttttc | tcactttatc | 120 |
| aggaattgag | tttaacacat | attaaagcag | gtgtggggca | gggaggggg | gataaaaaag | 180 |
| aaggtgctca | agaaaagccg | atcacgctcc | caagagtgtg | agcatgggcg | tctctagaga | 240 |
| gatccgccat | atatgcacaa | cttttaaaga | gaaattcaat | aaccagaatg | gagtgtaaat | 300 |
| gtggatcaaa | gttgtagaaa | cattctttta | tgttatagaa | aatgcttttt | aagcagggt | 360 |
| gggggtcaag | atgttaacta | ttattaaaga | gcaaaaaaaa | aaaatgcat | tttgtttgaa | 420 |
| gacccagggc | actggaaacc | ctgagtttca | ggactcgcct | ttattaggtg | tcctctatct | 480 |
| gattgttagc | aattattcat | ttcctcagag | agagaataaa | ttgcttgggg | attcggccct | 540 |
| gctctgcgct | cttcctttgc | tgaaggccag | cgctgaagac | ttcagagtca | tgagaaggat | 600 |
| gcttctgcac | ttgagtgttc | tgactctcag | ctgtgtctgg | gccactgcca | tggagattcc | 660 |
| catgagcaca | gtggtgaaag | agaccttgac | acagctgtcc | gctcaccgag | ctctgttgac | 720 |
| aagcaatgag | gtaaagtata | acttattcct | tcagctttgt | ttttaagatc | aggaccttgc | 780 |
| tataccgctc | tgactggcct | caaacttgct | atgtagggta | ggctgtccta | accctacca | 840 |
| gatctcctta | cctatgtctc | ccaaatacta | ggattacaga | cacattacct | tgcctgacgc | 900 |
| tatggttctt | cagaatgcat | aaatagctgc | atttggcctt | taatcccaga | acttgggagg | 960 |
| cagggtcagg | tggatctctg | tgagttcaag | gccagacttg | tctacgtggc | cagttacagg | 1020 |
| acagccagag | ctaaagcaag | accctgattc | aaaataattt | ttttttcaaaa | caaaaaaaaa | 1080 |
| aaacccaaac | catttgtggc | aattcatttc | taaacataaa | gatctgcttt | aaatagtgca | 1140 |
| attatggctt | gttcccttgc | cttcttgctc | ccgttctgtc | ctcttgtccc | actctctccc | 1200 |
| cattccaccc | ccaccatgtg | ctcatggccc | gcatctctac | ttctctactc | tctttctctc | 1260 |
| cctctcccct | ccttcttcct | ttccctctct | ctctccctct | tcttctcctc | ctctctttct | 1320 |
| ctctctctcc | ctctctctct | ctctttctct | ctctctctgc | tttttttctat | ctctactacc | 1380 |
| ctctcaactc | ccctctccat | gccctgaata | agctctattc | tatactaaaa | aaaaaaagt | 1440 |
| gcaattatga | atgtgttagt | gttaatgcac | aggtgataac | cctatcacca | gcaagcattg | 1500 |
| cattaaaaaa | ggcaacggac | tctctttagg | atgaccctat | gatgttcttt | cctttgcaga | 1560 |
| cgatgaggct | tcctgtccct | actcataaaa | atgtaagtta | ttctttactg | ccgtgcttgc | 1620 |
| atgagtaagt | cagcttcgca | tactaagcta | taagtcatct | gcatctagct | ttctggtgtt | 1680 |
| gtgtgtgtct | gggatgggga | cctctctagg | tctcaagctc | ctgggttcaa | gtgattctct | 1740 |
| tgccttgata | gagcagctgg | gacacaggcc | tgtgccacca | cacccagcag | agcttttgat | 1800 |
| ttcagttaaa | ctgtttgact | ttcttggaaa | agaaaattta | tgtaggtaga | tatgaaagtt | 1860 |
| tgtgcttata | aataaaaaga | atatgagagt | ggcaaattat | gtaatcccag | tacttgggag | 1920 |
| ccaaaggcag | gggtagtctg | agtctagggc | cagcttagat | acattgccct | gtatgtatca | 1980 |
| aaagtaaatc | ctataaataa | ataaacaaaa | acattagagg | gctggagata | taagctctgt | 2040 |

-continued

```
tgatagatgg cctaatatgc tgggttgact cttagcaccc cataaactaa acatggaagt    2100
acctggctgt aatctcatga tggtgaaatg gaggcgggaa gatcataggt tcaaggtcat    2160
cctcagctac atttttgagc tagaggccag cctgggctat gagacacgca aaaccacca    2220 gccaattaat attaggaatg ctttgagct agatctgtta tgtaagtggc cagctggagc    2280
tgtcagtcat acatctcaca gcctcacaag attctttgca tggcgagagg tcctgctggg    2340 ctcccttttgg ctctgtccat ggctctcttc atcctagtgc ctctctttgt tttccttgtc    2400
ttatttctta ctgctgagga tcaagcccag ggccttcagt gtgtgaagtg agcactctac    2460
cactgaattc cagagcccgc ccactctaat gcctttctga agtattaag agtttagggt    2520 tatatattcc ttttgtttat tttatgtgta tgagcatttt gcctgcatat atatatatat    2580
atatatatat atatatatat gtgtgtgtgt gtgtgtgtgt gtgtgtatat atatatgtat    2640
gtatgtatgt atgtatgtat gtatgtatat gtgtgtgtgt gtgtgtgtgt gtgtgtgtgt    2700
gttccacgta tgtgtctatg tgtctggtgt tcctgaaggc taaagaagg gcatcagatc    2760 acctggggct ggatatgcag atggttgtga gccaaccatc tggatgctgg gaactgcatc    2820
aagtgttctt aaccactgag ccatctctcc cgctcagagg gttatattct taggtaatga    2880
tagaaagaca taaaaatatc atgaatgcct ttattaataa tttctaaaca gtttaatgaa    2940
tatgactatg tagtgatatt gtatacattt caatattatc ttattctagc gtaaagtaca    3000
ttatttaact ttttctaaat agaagaaaat tcatcagcct aaatttcaaa agaaaatatt    3060
aatatgggtg tggtaccact cacctttaat ccagatggtt gtgagccacc acaagggtgc    3120
tggtaactga acccaggtcc tctggaagag gacccagtga tcttaaccac tgagccatct    3180
ccccagcccc aatcctaact ttgggttcat tttttttgaaa tgatctcatg tagcactagc    3240
tggcctcaaa ctctatgtat cagaggctgg ccttcaactc ctgatcctct tacctcaact    3300
tcctgaatgc tggcattaca gataagcacc atcacatctt gtattgtctg gggttttta    3360 ttgatgcatt taaattgcat gtatttattg catatggcat gatatttcaa aatatgtgta    3420
cgttgtgggc agtctgatct atttgcttct tgataatctt ctttcagcac cagctatgca    3480
ttggagaaat ctttcagggg ctagacatac tgaagaatca aactgtccgt gggggtactg    3540
tggaaatgct attccaaaac ctgtcattaa taaagaaata cattgaccgc caaaaagtaa    3600
gttccccagg gaccctgtga atccggctgc agctggttct ccaggagcca acctgacagt    3660
ctgttctttt cacaggagaa gtgtggcgag gagagacgga ggacgaggca gttcctggat    3720
tacctgcaag agttccttgg tgtgatgagt acagagtggg caatggaagg ctgaggctga    3780
gctgctccat ggtgacagga cttcacaatt taagttaaat tgtcaacaga tgcaaaaacc    3840
ccacaaaact gtgcaaatgc aagggatacc atatgctgtt tccatttata tttatgtcct    3900
gtagtcagtt aaacctatct atgtccatat atgcaaagtg tttaaccttt ttgtatacgc    3960
ataaaagaaa ttcctgtagc gcaggctggc ctcaaactgg taatgtagcc aaggataacc    4020
ttgaatttct gatcctcctg cctcctcttc ctgaaggctg aggttacaga catgcaccat    4080
tgccactagt tcatgaagtg ctggagatgg aacccaaggc tttgtgcatg ttaccaactg    4140
agttatactc cctcccctc atcctcttcg ttgcatcagg gtctcaagta ttccaggctg    4200
actttgaact cagtgtgtag ccaagggtga ccctgaactc ttggtccaga tggacgcagg    4260
aggatcacat acccaacctt agcatccttt ctcctagccc ctttagatag atgatactta    4320
atgactctct tgctgaggga tgccacaccg gggcttcctg ctcctatcta acttcaattt    4380
```

-continued

```
aatacccact agtcaatctc tcctcaactc cctgctactc tccccaaact ctagtaagcc    4440
cacttctatt tcttggggag agagaaggtt gacttttctt atgtcctatg tatgaatcag    4500
actgtgccat gactgtgcct ctgtgcctgg agcagctgga ttttggaaaa gaaaagggac    4560
atctccttgc agtgtgaatg agagccagcc acatgctggg ccttacttct ccgtgtaact    4620
gaacttaaga agcaaagtaa ataccacaac cttactaccc catgccaaca gaaagcataa    4680
aatggttggg atgttattca ggtatcaggg tcactggaga agcctccccc agtttactcc    4740
aggaaaaaca gatgtatgct tttatttaat tctgtaagat gttcatatta tttatgatgg    4800
attcagtaag ttaatatttta ttacaacgta tataatattc taataaagca gaagggacaa    4860
ctcaaattca gtttgctatt ggtcttttct aaccctgggt gtgtgcaggg acccagagga    4920
gagactgagt atgtcctgac taagcacttt cagctcctta gagcttcagg gagcaccaag    4980
ggtggacttg gtagtggtat cgggagcaag aacaagggct gggactgagc ctggatctcc    5040
ctatgtagga gtatgtccag atggctcagg gtgaacagga gaggaatgaa tgagaggatg    5100
aatgaatgaa tgaataaatg aatgaatggg agatcgctcc attaataaag tgcttgctgt    5160
acaaggatga agagctgagt tcgagctcca aaacccattt cagaaagctg gcatggtgg    5220 gggcacactt gtagtcctga cactgggaga cagaaatagc cagatccctg gggctctctg    5280
ttcagccaac ctaaatgaat tggtgagttc tggaccagtg agagatcttc tctcaaaaag    5340
caaggtggaa gccgagcgtg gtgacacacg cctttaattc cagcacttgg gaggcagagg    5400
caggcggatt tctgagttcg aggccagcct ggtctacaaa gtgagttcca ggacagccag    5460
ggctacacag agaaaccctg tctcaaaaaa caaacaaaca aacaaacaaa caaaccacca    5520
tgaactacct gtgtatgcat gttgtgtgtg cttgcattgt gcaggtcaaa tgaacacact    5580
gggactcttc cactaacact ctctacctcg ttccctaaga gggtctcctg ctgaacatgg    5640
agtttcccat ttcttttggt taggctggca gccagccagc aagtcccagc gatcctcctg    5700
tctcctcttc ctcctgctca gccccagggg tggagtctta ggtatgcgtg gccatgccag    5760 gcttttttcca tgggtgctgg agatccagac gcagcttctc atgttcgcgc agtggcactc    5820
ttgcccactg aagcatcttc catcttgccc actgaagcat ctcccatctt acccactcaa    5880
gcatcttcca tcttacccac tcaagcatct tccatcttac ccactcaagc atcttccatc    5940
ttacccactc aagcatcttc cagctcctta gtatgttttt tttttaaaca tgtacttggc    6000 ttttttaaaat tgtaataaac taaggtata caatatgtat tgattgatat gcttacttat    6060
gtatttatct ttattttctt atttttttaa aaaatttatt ttatttatat gaatacactg    6120
tagctgactt cagacacacc agaacagggc attggatccc attacggatg gttgtgagcc    6180
accatgtggt tgctgggaat tgaactcagg acctttggaa gaacagtctc tctggctctg    6240
tagttatctt tcagtatact tttccttgaa aattttatat gtctgtgcga tctattctgg    6300
tcctaccatt cactctcact cttcctggac ttcccagtat ggccccctcc cgatttcaaa    6360
tcttctcact cttatttttt agcccactga gttcagttag tgttgtccct atgagcacgt    6420
gtggaccatc tacttgagct taggcaacct accagtggcc acatccctac aggaaaggta    6480
ctcttcctct cttggtggcc ataaaccccc aacgggtcct cacataggc aggagcctta    6540 ggagtttccc tccccattca tactaaactt tggttggctt gatggtgtga agataaccac    6600
agctgctgtg aggtcctgag tacaagggcc aagtcacgtc caggaggcag catctcacag    6660
tacttacccc cagtctctgg ctcgaacatc cttcccacca tccccttca tcatgttcct    6720 taagctt                                                              6727
```

```
<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 2
cccaagcaat ttattctctc                                              20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 3
tcagcaaagg aagagcgcag                                              20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 4
cactgtgctc atgggaatct                                              20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 5
actttacctc attgcttgtc                                              20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 6
tcagagcggt atagcaaggt                                              20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 7
ctcatcgtct gcaaaggaaa                                              20

<210> SEQ ID NO 8
<211> LENGTH: 20
<212> TYPE: DNA
<213> ORGANISM: Artificial Sequence
<220> FEATURE:
```

<223> OTHER INFORMATION: Description of Artificial Sequence:Synthetic

<400> SEQUENCE: 8
tatgagtagg gacaggaagc                                              20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 9
atttttatga gtagggacag                                              20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 10
agcacggcag taaagaataa                                              20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 11
acaaggaaaa caaagagagg                                              20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 12
ctggtgctga aagaagatta                                              20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 13
ccacggacag tttgatcctt                                              20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 14
aatgacaggt tttggaatag                                              20

```
<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 15
gcggtcaatg tatttctttta                                                    20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 16
ggaacttact ttttggcggt                                                     20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 17
cagactgtca ggttggctcc                                                     20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 18
tcctcgccac acttctcctg                                                     20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 19
aactgcctcg tcctccgtct                                                     20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 20
tactcatcac accaaggaac                                                     20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence:Synthetic
```

-continued

<400> SEQUENCE: 21
ctcagcctca gccttccatt                    20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 22
ttaaattgtg aagtcctgtc                    20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 23
aaatataaat ggaaacagca                    20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 24
ctacaggaca taaatataaa                    20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 25
tatacaaaaa ggttaaacac                    20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 26
ggttatcctt ggctacatta                    20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 27
aactgcctcc tcctccgtct                    20

<210> SEQ ID NO 28
<211> LENGTH: 20

```
<212> TYPE: DNA
<213> ORGANISM: Artificial Sequence
<220> FEATURE:
<223> OTHER INFORMATION: Description of Artificial Sequence:Synthetic

<400> SEQUENCE: 28
aactgccacc tgctccgtct                                             20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 29
aactggcacc tgcaccgtct                                             20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 30
ggttatccta ggctacatta                                             20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 31
ggttatcgta gcctacatta                                             20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 32
ggttaacgta gccaacatta                                             20

<210> SEQ ID NO 33
<211> LENGTH: 29
<212> TYPE: DNA
<213> ORGANISM: Artificial Sequence
<220> FEATURE:
<223> OTHER INFORMATION: Description of Artificial Sequence:Synthetic

<400> SEQUENCE: 33
agtgttctga ctctcagctg tgtctgggc                                   29

<210> SEQ ID NO 34
<211> LENGTH: 24
<212> TYPE: DNA
<213> ORGANISM: Artificial Sequence
<220> FEATURE:
<223> OTHER INFORMATION: Description of Artificial Sequence:Synthetic

<400> SEQUENCE: 34
```

```
ttcagagtca tgagaaggat gctt                                    24

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence:Synthetic

<400> SEQUENCE: 35
accactgtgc tcatgggaat ct                                      22

<210> SEQ ID NO 36
<211> LENGTH: 27
<212> TYPE: DNA
<213> ORGANISM: Artificial Sequence
<220> FEATURE:
<223> OTHER INFORMATION: Description of Artificial Sequence:Synthetic

<400> SEQUENCE: 36
aaggccgaga atgggaagct tgtcatc                                 27

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 37
ggcaaattca acggcacagt                                         20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 38
gggtctcgct cctggaagat                                         20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 39
ctttggcaaa gaaagtgcat                                         20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 40
cgttctgcgt ttgcctttgg                                         20

<210> SEQ ID NO 41
<211> LENGTH: 20
<212> TYPE: DNA
<213> ORGANISM: Artificial Sequence
```

```
<220> FEATURE:
<223> OTHER INFORMATION: Description of Artificial Sequence:Synthetic

<400> SEQUENCE: 41
tcctcatggc tctgaaacgt                                              20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 42
aagaaaatta cctcattggc                                              20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 43
ttacagcaca ccagcattca                                              20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 44
tcctcagagt ctggagagga                                              20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 45
ggaacaggaa tcctcagagt                                              20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 46
tttaacttac atttttatgt                                              20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 47
tttacttatt catgccatca                                              20
```

```
<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 48
gacacgatgc tctttgggaa                                                   20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 49
cattttaata tgaccaggca                                                   20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 50
ttctaggcaa caaaccacca                                                   20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 51
acagttggtg ctaaatgagg                                                   20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 52
ttcttcagtg cacagttggt                                                   20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 53 accccttgc acagtttgac                                                    20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence:Synthetic
```

```
<400> SEQUENCE: 54
tggccgtcaa tgtatttctt                                              20

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 55
tgtaacttac tttttggccg                                              20

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 56
tccatagaaa taggcacagc                                              20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 57 cacactttt ctgtgaaaaa                                               20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 58
attggtttac tctccgtctt                                              20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 59
ttatccactc ggtgttcatt                                              20

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 60
tccttctcct ccaaaatctt                                              20

<210> SEQ ID NO 61
```

<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 61
tggccctcat tctcactgca                                                 20

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 62
tctggcaaag tgtcagtatg                                                 20

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 63
ttgcctggag gaaaatactt                                                 20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 64
ctttggcaaa gaaagtgcat                                                 20

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 65
cgttctgcgt ttgcctttgg                                                 20

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 66
aagaaaatta cctcattggc                                                 20

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 67
tcctcagagt ctggagagga                                                      20

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 68
tttaacttac atttttatgt                                                      20

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 69
acagttggtg ctaaatgagg                                                      20

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 70
tgtaacttac tttttggccg                                                      20

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 71 cacactttt ctgtgaaaaa                                                       20

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 72
tctggcaaac tgtcagtatg                                                      20

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 73
tctggcatac tctcagtatg                                                      20

<210> SEQ ID NO 74
<211> LENGTH: 20
<212> TYPE: DNA

```
<213> ORGANISM: Artificial Sequence
<220> FEATURE:
<223> OTHER INFORMATION: Description of Artificial Sequence:Synthetic

<400> SEQUENCE: 74
tctgggatac tctgagtatg                                              20

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 75
ttgcctggac gaaaatactt                                              20

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 76
ttgcctgcac gtaaatactt                                              20

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 77
ttgccagcac gtatatactt                                              20

<210> SEQ ID NO 78
<211> LENGTH: 3230
<212> TYPE: DNA
<213> ORGANISM: Homo sapiens

<400> SEQUENCE: 78
atcctaatca agacccagt  gaacagaact  cgaccctgcc  aaggcttggc  atttccattt    60
caatcactgt cttcccacca gtattttcaa tttcttttaa gacagattaa tctagccaca    120
gtcatagtag aacatagccg atcttgaaaa aaaacattcc caatatttat gtattttagc    180
ataaaattct gtttagtggt ctaccttata ctttgttttg cacacatctt ttaagaggaa    240
gttaattttc tgattttaag aaatgcaaat gtggggcaat gatgtattaa cccaaagatt    300
ccttccgtaa tagaaaatgt ttttaaaggg gggaaacagg gattttttatt attaaaagat    360 aaaagtaaat ttatttttta agatataagg cattggaaac atttagtttc acgatatgcc    420
attattaggc attctctatc tgattgttag aaattattca tttcctcaaa gacagacaat    480
aaattgactg gggacgcagt cttgtactat gcactttctt tgccaaaggc aaacgcagaa    540
cgtttcagag ccatgaggat gcttctgcat ttgagtttgc tagctcttgg agctgcctac    600
gtgtatgcca tccccacaga aattcccaca agtgcattgg tgaaagagac cttggcactg    660
ctttctactc atcgaactct gctgatagcc aatgaggtaa ttttctttat gattcctaca    720
gtctgtaaag tgcataggta atcatttgtg atggttcctt tactatatat agagatctgt    780
tataaataat aagattctga gcacattagt acatgggtga taactacatc accagcaaac    840
```

```
attctgttaa aagttatgaa tgctggtgtg ctgtaaaaat gattgtattt cctttcctct    900
ccagactctg aggattcctg ttcctgtaca taaaaatgta agttaaatta tgattcagta    960
aaatgatggc atgaataagt aaatttcctg ttttaagctg taaatcatta gttatcattg   1020
gaactatttta attttctata ttttgttttc atatgggtgg ctgtgaatgt ctgtacttat   1080
aaatatgagg aatgactttt tatcaagtag aatcctttaa acaagtggat taggctcttt   1140
ggtgatgttg ttagtttgcc ttcccaaaga gcatcgtgtc aggattcttt ccagaaggat   1200
tccacactga gtgagaggtg cgtgctagtc tccgtgcagt tctgactctt tctcactcta   1260
acgtgtttct gaaagtatta gcaactcaga attatatttt tagaaccatg atcagtagac   1320
attaaaatat ataacaaatg ccctatatta ataattctgc atacttaaat aattatgact   1380
atatgatggt gtgtatgcat tgaatatgcc tggtcatatt aaaatgtaaa atatatagtt   1440
tattagtcta aatagaataa aactaccagc tagaactgta gaaacacatt gatatgagtt   1500
taatgtataa tgcattacac ttccaaaaca ttttttttcca gttacataat taagttatat   1560
cctttataaa actcctcagt aatcatataa gcttcatcta cttttttgaaa attttatctt   1620
aatatgtggt ggtttgttgc ctagaaaaca acaaaaaaac tctttggaga agggaactca   1680
tgtaaatacc acaaaacaaa gcctaacttt gtggaccaaa attgttttaa taattatttt   1740
ttaattgatg aattaaaaag tatatatatt tattgtgtac aatatgatgt tttgaagtat   1800
gtatacattg cagaatggac aatggaccaa attttttatac cttgtcttga ttatttgcat   1860
tttaaaaatt ttcctcattt agcaccaact gtgcactgaa gaaatctttc agggaatagg   1920
cacactggag agtcaaactg tgcaaggggg tactgtggaa agactattca aaaacttgtc   1980
cttaataaag aaatacattg acggccaaaa agtaagttac acacattcaa tggaagctat   2040
atttgtcctg gctgtgccta tttctatgga attgacagtt tcctgtaata cctattgtca   2100
ttttctttt ttcacagaaa aagtgtggag aagaaagacg gagagtaaac caattcctag   2160
actacctgca agagtttctt ggtgtaatga acaccgagtg gataatagaa agttgagact   2220
aaactggttt gttgcagcca aagattttgg aggagaagga catttttactg cagtgagaat   2280
gagggccaag aaagagtcag gccttaattt tcaatataat ttaacttcag agggaaagta   2340
aatatttcag gcatactgac actttgccag aaagcataaa attcttaaaa tatatttcag   2400
atatcagaat cattgaagta ttttcctcca ggcaaaattg atatactttt ttcttattta   2460
acttaacatt ctgtaaaatg tctgttaact taatagtatt tatgaaatgg ttaagaattt   2520
ggtaaattag tatttattta atgttatgtt gtgttctaat aaaacaaaaa tagacaactg   2580
ttcaatttgc tgctggcctc tgtccttagc aatttgaagt tagcacagtc cattgagtac   2640
atgcccagtt tggaggaagg gtctgagcac atgtggctga gcatccccat ttctctggag   2700
aagtctcaag gttgcaaggc acaccagagg tggaagtgat ctagcaggac ttagtgggga   2760
tgtggggagc agggacacag gcaggaggtg aacctggttt tctctctaca gtatatccag   2820
aacctgggat ggtcgaaggg taatggtag ggaataaatg aatgaatgtc gtttccaaga   2880
tgattgtaga actaaaatga gttgtaagct cccctggaag aagggatgtg gaacctgtaa   2940
ctaggttcct gcccagcctg tgagaagaat ttggcagatc atctcattgc cagtatagag   3000
aggaagccag aaaccctctc tgccaaggcc tgcagggggtt cttaccacct gaccctgcac   3060
cataacaaaa ggacagagag acatggtagg gcagtcccat tagaaagact gagttccgta   3120
ttcccggggc agggcagcac caggccgcac aacatccatt ctgcctgctt atggctatca   3180
```
gtagcatcac tagagattct tctgtttgag aaaacttctc tcaaggatcc          3230

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 79
gacctgtcca gtgagcttct                                            20

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 80
tagccgaata ctggaaaggt                                            20

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 81
aacacaggca ccatggtagc                                            20

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 82
ctcttggtca ggatttgggt                                            20

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 83
tcctcacgct agctgcaaag                                            20

<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 84
atggccttaa gtgggtgtgg                                            20

<210> SEQ ID NO 85
<211> LENGTH: 20
<212> TYPE: DNA
<213> ORGANISM: Artificial Sequence

```
<220> FEATURE:
<223> OTHER INFORMATION: Description of Artificial Sequence:Synthetic

<400> SEQUENCE: 85
gagccattaa tgtgcacagc                                                    20

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 86
tccactcgcc ccaccttcct                                                    20

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 87
aacaagacga agcaggcagc                                                    20

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 88
ccggaaccgg tggaaacaac                                                    20

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 89
ccaacctctt ccacacaatg                                                    20

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 90
tcccatgact tcaaatccaa                                                    20

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 91
gcaaaatgcc atcaaaacgt                                                    20
```

<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 92
cgagctctac caccgcctgg                                           20

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 93
caagctggcc tcgaactcag                                           20

<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 94
ggatgggttg gtgacttgca                                           20

<210> SEQ ID NO 95
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 95
tgaggaaacc aaaggcccat                                           20

<210> SEQ ID NO 96
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 96
tgtctcccac ttgcgtcagg                                           20

<210> SEQ ID NO 97
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 97
ttgaacaggc ctatggaaca                                           20

<210> SEQ ID NO 98
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 98 tcttttcac cccaggcacg                                           20

<210> SEQ ID NO 99
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 99
aattcccatg gatcctcttg                                          20

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 100
atccagcaat cacctccaaa                                          20

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 101
tgttcagccc atcaaaaaga                                          20

<210> SEQ ID NO 102
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 102
atttggctga caggaccccg                                          20

<210> SEQ ID NO 103
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 103
tccagagact gccccaccca                                          20

<210> SEQ ID NO 104
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 104
catctgcttc tgtattgcca                                          20

<210> SEQ ID NO 105

```
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 105
ccttttagct ccttgggtac                                                   20

<210> SEQ ID NO 106
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 106
catttctgag ggttgctggg                                                   20

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 107
catctgattg tgtcttgcca                                                   20

<210> SEQ ID NO 108
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 108
catctgcttg tgtattgcca                                                   20

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 109
cacctgattg tgtcttgtca                                                   20

<210> SEQ ID NO 110
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 110
tgtccctcct tttggtgggg                                                   20

<210> SEQ ID NO 111
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 111
```
ttagctctgt ctctgctgat                    20

<210> SEQ ID NO 112
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 112
aactgctggc cagagttgta                    20

<210> SEQ ID NO 113
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 113
catagttaaa gcaatgatct                    20

<210> SEQ ID NO 114
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 114
gtttctcata ttcagtaacc                    20

<210> SEQ ID NO 115
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 115
ggagtcctgt atgagttcat                    20

<210> SEQ ID NO 116
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 116
tctgtgcatc ccaggtgctg                    20

<210> SEQ ID NO 117
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 117
ctggctgtcc tggaactcac                    20

<210> SEQ ID NO 118
<211> LENGTH: 20
<212> TYPE: DNA

-continued

<213> ORGANISM: Artificial Sequence
<220> FEATURE:
<223> OTHER INFORMATION: Description of Artificial Sequence:Synthetic

<400> SEQUENCE: 118
ttcaaggtaa gtcaagcaac                                                   20

<210> SEQ ID NO 119
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 119
ctgatggcta ccactggcaa                                                   20

<210> SEQ ID NO 120
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 120
cactctcaat gagttctatc                                                   20

<210> SEQ ID NO 121
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 121
tgatgctggt tgatcaatct                                                   20

<210> SEQ ID NO 122
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 122
tcaataggga atggtgtctt                                                   20

<210> SEQ ID NO 123
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 123
ttccagagta cctagaagcc                                                   20

<210> SEQ ID NO 124
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 124
ccaacaggtt gccatgaagg                                                   20

<210> SEQ ID NO 125
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 125
agagattaga attgactaag                                              20

<210> SEQ ID NO 126
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 126
actattgcat atactagcaa                                              20

<210> SEQ ID NO 127
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 127
ccatccaata tacaaccacc                                              20

<210> SEQ ID NO 128
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 128
ctcatggaag gagttacaga                                              20

<210> SEQ ID NO 129
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 129
tgtggatact tcactgcttc                                              20

<210> SEQ ID NO 130
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 130
atccaataga tgactgtgag                                              20

<210> SEQ ID NO 131
<211> LENGTH: 20
<212> TYPE: DNA
<213> ORGANISM: Artificial Sequence
<220> FEATURE:

<223> OTHER INFORMATION: Description of Artificial Sequence:Synthetic

<400> SEQUENCE: 131
gttcatattg ttgttcctgc                                                              20

<210> SEQ ID NO 132
<211> LENGTH: 3571
<212> TYPE: DNA
<213> ORGANISM: Mus musculus
<220> FEATURE:
<223> OTHER INFORMATION: Description of Artificial Sequence:Synthetic

<400> SEQUENCE: 132

| | | | | | |
|---|---|---|---|---|---|
| gaaataattg | gtaaacacag | aaaatgtttc | aatagaaaaa | agaggaaaca | gaacactgtg | 60 |
| tagccctgtt | atcagcagag | acagagctaa | cgctggggat | accaaactag | aagaagctca | 120 |
| ctggacaggt | cccggtatgc | agttctattt | ttgttgatgg | ctctgtatct | aatgtgttca | 180 |
| tttgtaccaa | ggatctaacc | agggtcttcc | agagtctgag | caagcttctc | ccactgagct | 240 |
| acatcacagc | cccctgttta | ttggaagaag | aaatacttac | acctttccag | tattcggcta | 300 |
| ccatggtgcc | tgtgttacta | attcttgtgg | gagctttggc | aacactgcaa | gctgacttac | 360 |
| ttaatcacaa | aaagttttta | cttctaccac | ctgtcaattt | taccattaaa | gccactggat | 420 |
| tagctcaagt | tcttttacac | tgggacccaa | atcctgacca | agagcaaagg | catgttgatc | 480 |
| tagagtatca | cgtgaaaata | aatgccccac | aagaagacga | atatgatacc | agaaagactg | 540 |
| aaagcaaatg | tgtgaccccc | cttcatgaag | gctttgcagc | tagcgtgagg | accattctga | 600 |
| agagcagcca | tacaactctg | gccagcagtt | gggtttctgc | tgaactcaaa | gctccaccag | 660 |
| gatctcctgg | aacctcggtt | acgaatttaa | cttgtaccac | acacactgtt | gtaagtagcc | 720 |
| acacccactt | aaggccatac | caagtgtccc | ttcgttgcac | ctggcttgtt | gggaaggatg | 780 |
| cccctgagga | cacacagtat | ttcctatact | acaggtttgg | tgttttgact | gaaaaatgcc | 840 |
| aagaatacag | cagagatgca | ctgaacagaa | atactgcatg | ctggtttccc | aggacattta | 900 |
| tcaacagcaa | agggtttgaa | cagcttgctg | tgcacattaa | tggctcaagc | aagcgtgctg | 960 |
| caatcaagcc | ctttgatcag | ctgttcagtc | cacttgccat | tgaccaagtg | aatcctccaa | 1020 |
| ggaatgtcac | agtggaaatt | gaaagcaatt | ctctctatat | acagtgggag | aaaccacttt | 1080 |
| ctgcctttcc | agatcattgc | tttaactatg | agctgaaaat | ttacaacaca | aaaaatggtc | 1140 |
| acattcagaa | ggaaaaactg | atcgccaata | agttcatctc | aaaaattgat | gatgtttcta | 1200 |
| catattccat | tcaagtgaga | gcagctgtga | gctcaccttg | cagaatgcca | ggaaggtggg | 1260 |
| gcgagtggag | tcaacctatt | tatgtgggaa | aggaaaggaa | gtccttggta | gaatggcatc | 1320 |
| tcattgtgct | cccaacagct | gcctgcttcg | tcttgttaat | cttctcactc | atctgcagag | 1380 |
| tgtgtcattt | atggaccagg | ttgtttccac | cggttccggc | cccaaagagt | aacatcaaag | 1440 |
| atctccctgt | ggttactgaa | tatgagaaac | cttcgaatga | aaccaaaatt | gaagttgtac | 1500 |
| attgtgtgga | agaggttgga | tttgaagtca | tgggaaattc | cacgttttga | tggcattttg | 1560 |
| ccattctgaa | atgaactcat | acaggactcc | gtgataagag | caaggactgc | tatttcttgg | 1620 |
| caaggaggta | tttcaaatga | acactcagag | ccaggcggtg | gtagagctcg | cctttaatac | 1680 |
| cagcacctgg | gatgcacaga | cgggaggatt | tctgagttcg | aggccagctt | ggtctataaa | 1740 |
| gtgagttcca | ggacagccag | agctacacag | agaaaccctg | tctcgaaaaa | acaaacaaac | 1800 |
| aaacaaacaa | acaaaaatga | acactcaatt | tgaatgcaag | tcaccaaccc | atccagacat | 1860 |
| gagtcaccaa | tgtcccattt | cataaagtgt | gcatgcctca | ctcaaacctc | cttgctcaca | 1920 |

```
gcatagcacc agactcaccc agagcatggg cctttggttt cctacccaga gtaccatgtt   1980
ataccagtgt gtctttgaaa gttgcttgac ttaccttgaa cttttttgcac aggagacagt  2040 tttttttaagc taatgtcaca catgtttact ttgggttaag ttgccagtgg tagcactcag  2100
ctacagtgac aggaggaaag gatagaactc attgagagtg aacccaaatt caagactgtc  2160
tttcctgacg caagtgggag acacaatttc atggtgcttt tccccttttca gttctagaat  2220 agtttccttt ctagaactgt gcctgtgtct taaagcataa ggtaacattg aggcaaaaac  2280
aaagactatg tcccacatgt ccctgtgttc cataggcctg ttcaaggaaa tgtctaagcc  2340
aaagtaagtt taagtcaccg tgcctggggt gaaaagatg gttcagatga cgaagaagca   2400
tgagggcctg agattgatca accagcatca agaaacaaca acaacaacag cagcagcaac  2460
aacaaaacag tgcaagaagc acattcctat aaccccagag ttgggagata agacaagag   2520 gatccatggg aattgtagtt caaccagttt agccaattat gttatctcta ggttcactga  2580
gagaaatggt cttaaaaatt taaggtggag agtgactagg cagatcctct gatactgact  2640
tctgccctaa atatgcatac acatgtacac acacaacaca aagacaccat tccctattga  2700
gagagaagac agaagcttgt tcaaggatta aattcttcaa ggcttctagg tactctggaa  2760
atgacctgag aaagacattg aaaataattc tgctttggag gtgattgctg gatctagaat  2820
gtacttccca aagagatgtt gatgaaagag ccttcatggc aacctgttgg tcaactcatg  2880
cttagtcaat tctaatctct taaattaggg tttcctatac atattacaat tgtataaaaa  2940
tgtattctct aaatatcttc attaatgaag ctgtatctat aggtctttttt gatgggctga  3000 acatagaagc aaacacactt atgtgttggg aagaggaata agtagtgata gagggaccta  3060
gtggtagtta ttttacatag tcctgaagag ctaaagacaa tgaaagaaga aatggtactc  3120
acaagagaga gagctatgtc ggggtcctgt cagccaaatc ttgctagtat atgcaatagt  3180
gtctgggttt ggtggttgta tattggatgg ttccctgggt ggggcagtct ctggatggtc  3240
tttccttcca tcacagctct gaaatttgtc tctgtaactc cttccatgag tattttgttc  3300
cccattctaa gaagcagtga agtatccaca cttttggtctt ccttcttctt gagtttcatg  3360
tgttttgcaa attgtgtgcc tggcaataca gaagcagatg ctcacagtca tctattggat  3420
gaaacacagg gcccctaatg aaggagccag agaaagtacc caaggagcta aaagggtctg  3480
caaccctata gcaggaacaa caatatgaac tacccagcaa ccctcagaaa tgtaaatgaa  3540
gaaaatatct aataaaaaaa aaaaaaaaaa a                                  3571
```

<210> SEQ ID NO 133
<211> LENGTH: 965
<212> TYPE: DNA
<213> ORGANISM: Mus musculus
<220> FEATURE:
<223> OTHER INFORMATION: Description of Artificial Sequence:Synthetic

<400> SEQUENCE: 133

```
gccttggaga ctgtcactgt cagggctgat gacggatgag ctgggtcagg ctagatagac    60
cctagcaatt tattagagcc agactcctag gcaattctct ctctacatgt tcacttaagg   120
gttcagagct tcataacaaa gcagaagtca ggagtctcag aaatgcactt caaaatcagg   180
gtggaggaac ctgcccatgt gtcaggccct gtgacctatc aactcacaag ccttctgttg   240
ggatattgac caaacacagt atctttgctt atatgcaagc acacttgc gtgcaacaca     300 cacacacaca cacacacaca cacacacaca cacacacaca cacacaccag gctaaagctc   360
```

```
gcagagttct cagattgtgg tatatgaagg agcaagcctt tgtcagtgaa cagtatgatc      420
actaagactc tagtgtgggc cctctctaat gggttgctct cttgggaatc ttcttccaaa      480
gagcagttgt gtggtctttc cattgtaaga gaaactgcag gtgtcttctt aaccatgaca      540
gttctgatga tgaaagtgta aagaacccgc cttaaagtca acaccagtg cacccagaaa       600 gtagatgcac agctgcaggc tcagagctcg gcagccactg tacttcttag taaccaggaa     660
tcaaacgttt gactcactgt ggggttggta gggcagataa ataccttttt ctatgactag     720
gctggagaca cgcccaggac ccccaccaaa aggagggaca ggaaaagaga ataattggt      780 aaacacagaa aatgtttcaa tagaaaaaag aggaaacaga acactgtgta gccctgttat     840
cagcagagac agagctaacg ctggggatac caaactagaa gaagctcact ggacaggtcc    900
cggtatgcag ttctattttt gttgatggct ctgtatctaa tgtgttcatt tgtaccaagg    960
tgagt                                                                 965
```

<210> SEQ ID NO 134
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 134
caaggacttc ctttccttc                                                 20

<210> SEQ ID NO 135
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 135
gccattctac caaggacttc                                                20

<210> SEQ ID NO 136
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 136
acaatgagat gccattctac                                                20

<210> SEQ ID NO 137
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 137
tgttgggagc acaatgagat                                                20

<210> SEQ ID NO 138
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 138
agcaggcagc tgttgggagc                                              20

<210> SEQ ID NO 139
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 139
tgagaagatt aacaagacga                                              20

<210> SEQ ID NO 140
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 140
tgcagatgag tgagaagatt                                              20

<210> SEQ ID NO 141
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 141
actctgcaga tgagtgagaa                                              20

<210> SEQ ID NO 142
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 142
gacttccttt cctttcctgg                                              20

<210> SEQ ID NO 143
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 143
aacaagacga agcaggcagc                                              20

<210> SEQ ID NO 144
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 144
ctacactctg cagatgagtg                                              20

<210> SEQ ID NO 145
<211> LENGTH: 20
<212> TYPE: DNA

<213> ORGANISM: Artificial Sequence
<220> FEATURE:
<223> OTHER INFORMATION: Description of Artificial Sequence:Synthetic

<400> SEQUENCE: 145
cgatcagttt ttccttctaa                                    20

<210> SEQ ID NO 146
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 146
tcacccacat aaataggttg                                    20

<210> SEQ ID NO 147
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 147
ggtccataaa tgacacctga                                    20

<210> SEQ ID NO 148
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 148
ttacctcata ttcagtaacc                                    20

<210> SEQ ID NO 149
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 149
gccattctat caaggacttc                                    20

<210> SEQ ID NO 150
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 150
gccatgctat caagcacttc                                    20

<210> SEQ ID NO 151
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 151
gctatcctat caagcacgtc                                    20

<210> SEQ ID NO 152
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 152
gacttcctta cctttcctgg                                           20

<210> SEQ ID NO 153
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 153
gacttcctct tcttccctgg                                           20

<210> SEQ ID NO 154
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 154
gacctctttc cctcttctgg                                           20

<210> SEQ ID NO 155
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 155
gtttttcctt ctgaatgtga                                           20

<210> SEQ ID NO 156
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 156
ctttcctttc ccacataaat                                           20

<210> SEQ ID NO 157
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 157
taaatgacac actctgcaga                                           20

<210> SEQ ID NO 158
<211> LENGTH: 20
<212> TYPE: DNA
<213> ORGANISM: Artificial Sequence
<220> FEATURE:

<223> OTHER INFORMATION: Description of Artificial Sequence:Synthetic

<400> SEQUENCE: 158
taaatgacac ccacataaat        20

<210> SEQ ID NO 159
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 159
tcgaaggttt ccacataaat        20

<210> SEQ ID NO 160
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 160
aaccactctc tcaagggctt        20

<210> SEQ ID NO 161
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 161
tgctggaatt ggtggaaaca        20

<210> SEQ ID NO 162
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 162
gtctcaactc caggcttctc        20

<210> SEQ ID NO 163
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 163
tcaaaacaca gaatcctcca        20

<210> SEQ ID NO 164
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 164
aggatgccaa agtgacagtc        20

-continued

```
<210> SEQ ID NO 165
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 165
atccctgttc ttttcactga                                              20

<210> SEQ ID NO 166
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 166
cgcaggtaaa ttgagtgttg                                              20

<210> SEQ ID NO 167
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 167
tgaggcgatt tggatgaagc                                              20

<210> SEQ ID NO 168
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 168
tggacgttag ccttaaaagc                                              20

<210> SEQ ID NO 169
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 169
agcttaaaca gccaaacggg                                              20

<210> SEQ ID NO 170
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 170
ctccaggctg atgcaaaatg                                              20

<210> SEQ ID NO 171
<211> LENGTH: 20
<212> TYPE: DNA
<213> ORGANISM: Artificial Sequence
<220> FEATURE:
<223> OTHER INFORMATION: Description of Artificial Sequence:Synthetic
```

```
<400> SEQUENCE: 171
gggtgaggaa tttgtggctc                                                    20

<210> SEQ ID NO 172
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 172
ctggatcagg cctctggagc                                                    20

<210> SEQ ID NO 173
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 173
gggtgaggat tttgtggctc                                                    20

<210> SEQ ID NO 174
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 174
gggtgatgat ttggtggctc                                                    20

<210> SEQ ID NO 175
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 175
ggctgatgat ttggtgggtc                                                    20

<210> SEQ ID NO 176
<211> LENGTH: 2006
<212> TYPE: DNA
<213> ORGANISM: Homo sapiens

<400> SEQUENCE: 176
cggtcctcgc catcttctgt tgagtactgg tcggaacaag aggatcgtct gtagacagga        60
tatgatcatc gtggcgcatg tattactcat cctttggggg gccactgaga tactgcaagc      120
tgacttactt cctgatgaaa agatttcact tctcccacct gtcaatttca ccattaaagt      180
tactggtttg gctcaagttc ttttacaatg gaaaccaaat cctgatcaag agcaaaggaa      240
tgttaatcta gaatatcaag tgaaaataaa cgctccaaaa gaagatgact atgaaaccag      300
aatcactgaa agcaaatgtg taaccatcct ccacaaaggc ttttcagcaa gtgtgcggac      360
catcctgcag aacgaccact cactactggc cagcagctgg gcttctgctg aacttcatgc      420
cccaccaggg tctcctggaa cctcagttgt gaatttaact tgcaccacaa acactacaga      480
agacaattat tcacgtttaa ggtcatacca agtttccctt cactgcacct ggcttgttgg      540
cacagatgcc cctgaggaca cgcagtattt tctctactat aggtatggct cttggactga      600
```

-continued

```
agaatgccaa gaatacagca aagacacact ggggagaaat atcgcatgct ggtttcccag      660 gactttatc ctcagcaaag ggcgtgactg gcttgcggtg cttgttaacg gctccagcaa       720
gcactctgct atcaggccct ttgatcagct gtttgccctc cacgccattg atcaaataaa      780
tcctccactg aatgtcacag cagagattga aggaactcgt ctctctatcc aatgggagaa      840
accagtgtct gcttttccaa tccattgctt tgattatgaa gtaaaaatac acaatacaag      900
gaatggatat ttgcagatag aaaaattgat gaccaatgca ttcatctcaa taattgatga      960
tctttctaag tacgatgttc aagtgagagc agcagtgagc tccatgtgca gagaggcagg     1020
gctctggagt gagtggagcc aacctattta tgtgggaaat gatgaacaca agcccttgag     1080
agagtggttt gtcattgtga ttatggcaac catctgcttc atcttgttaa ttctctcgct     1140
tatctgtaaa atatgtcatt tatggatcaa gttgtttcca ccaattccag caccaaaaag     1200
taatatcaaa gatctctttg taaccactaa ctatgagaaa gctgggtcca gtgagacgga     1260
aattgaagtc atctgttata tagagaagcc tggagttgag accctggagg attctgtgtt     1320
ttgactgtca ctttggcatc ctctgatgaa ctcacacatg cctcagtgcc tcagtgaaaa     1380
gaacagggat gctggctctt ggctaagagg tgttcagaat ttaggcaaca ctcaatttac     1440
ctgcgaagca atacacccag acacaccagt cttgtatctc ttaaaagtat ggatgcttca     1500
tccaaatcgc ctcacctaca gcagggaagt tgactcatcc aagcattttg ccatgttttt     1560
tctccccatg ccgtacaggg tagcacctcc tcacctgcca atctttgcaa tttgcttgac     1620
tcacctcaga cttttcattc acaacagaca gcttttaagg ctaacgtcca gctgtattta     1680
cttctggctg tgcccgtttg gctgtttaag ctgccaattg tagcactcag ctaccatctg     1740
aggaagaaag cattttgcat cagcctggag tgaatcatga acttggattc aagactgtct     1800
tttctatagc aagtgagagc cacaaattcc tcaccccct acattctaga atgatctttt      1860
tctaggtaga ttgtgtatgt gtgtgtatga gagagagaga gagagagaga gagagagaga     1920
gagaaattat ctcaagctcc agaggcctga tccaggatac atcatttgaa accaactaat     1980
ttaaaagcat aatagagcta atatat                                          2006
```

<210> SEQ ID NO 177
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 177

```
cctgagaaat gcggtggcca                                                    20
```

<210> SEQ ID NO 178
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 178

```
gtgtctatgc tcgtggctgc                                                    20
```

<210> SEQ ID NO 179
<211> LENGTH: 20
<212> TYPE: DNA
<213> ORGANISM: Artificial Sequence
<220> FEATURE:

<223> OTHER INFORMATION: Description of Artificial Sequence:Synthetic

<400> SEQUENCE: 179
cgatcctctt gttccgacca                      20

<210> SEQ ID NO 180
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 180
atgcgccacg atgatcatat                      20

<210> SEQ ID NO 181
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 181
gcagtatctc agtggccccc                      20

<210> SEQ ID NO 182
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 182
tgctcttgat caggatttgg                      20

<210> SEQ ID NO 183
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 183
caggatggtc cgcacacttg                      20

<210> SEQ ID NO 184
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 184
gggcatgaag ttcagcagaa                      20

<210> SEQ ID NO 185
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 185
gccaggtgca gtgaagggaa                      20

<210> SEQ ID NO 186
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 186
ctccccagtg tgtctttgct                                            20

<210> SEQ ID NO 187
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 187
aagccagtca cgcccttttgc                                           20

<210> SEQ ID NO 188
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 188
aaacagctga tcaaagggcc                                            20

<210> SEQ ID NO 189
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 189
atggattgga aaagcagaca                                            20

<210> SEQ ID NO 190
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 190
tctgcacatg gagctcactg                                            20

<210> SEQ ID NO 191
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 191
aggttggctc cactcactcc                                            20

<210> SEQ ID NO 192
<211> LENGTH: 20
<212> TYPE: DNA
<213> ORGANISM: Artificial Sequence
<220> FEATURE:
<223> OTHER INFORMATION: Description of Artificial Sequence:Synthetic

```
<400> SEQUENCE: 192
tctgcacatg tagctcactg                                                 20

<210> SEQ ID NO 193
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 193
tctgcacgtg taactcactg                                                 20

<210> SEQ ID NO 194
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 194
tatgcacgtg taactccctg                                                 20

<210> SEQ ID NO 195
<211> LENGTH: 1998
<212> TYPE: DNA
<213> ORGANISM: Homo sapiens

<400> SEQUENCE: 195
ccgctgcttc tcatcgcatg gccaccgcat ttctcaggcc aggcacattg agcattggtc     60
ctgtgcctga cgctatgcta gatgctgggg ttgcagccac gagcatagac acgacagaca    120
cggtcctcgc catcttctgt tgagtactgg tcggaacaag aggatcgtct gtagacaggc    180
tacagattgt tttagattga agtttcctgt catgttcact catctttaaa tcctcatagt    240
aaaaaggata tgatcatcgt ggcgcatgta ttactcatcc ttttgggggc cactgagata    300
ctgcaagctg acttacttcc tgatgaaaag atttcacttc tcccacctgt caatttcacc    360
attaaagtta ctggtttggc tcaagttctt ttacaatgga accaaatcc tgatcaagag     420
caaggaatg ttaatctaga atatcaagtg aaaataaacg ctccaaaaga agatgactat     480
gaaaccagaa tcactgaaag caaatgtgta accatcctcc acaaaggctt ttcagcaagt    540
gtgcggacca tcctgcagaa cgaccactca ctactggcca gcagctgggc ttctgctgaa    600
cttcatgccc caccagggtc tcctggaacc tcaattgtga atttaacttg caccacaaac    660
actacagaag acaattattc acgtttaagg tcataccaag tttcccttca ctgcacctgg    720
cttgttggca cagatgcccc tgaggacacg cagtattttc tctactatag gtatggctct    780
tggactgaag aatgccaaga atacagcaaa gacacactgg ggagaaatat cgcatgctgg    840
tttcccagga cttttatcct cagcaaaggg cgtgactggc tttcggtgct tgttaacggc    900
tccagcaagc actctgctat caggcccttt gatcagctgt tgcccttca cgccattgat     960
caaataaatc ctccactgaa tgtcacagca gagattgaag gaactcgtct ctctatccaa   1020
tgggagaaac cagtgtctgc ttttccaatc cattgctttg attatgaagt aaaaatacac   1080
aatacaagga atggatattt gcagatagaa aaattgatga ccaatgcatt catctcaata   1140
attgatgatc tttctaagta cgatgttcaa gtgagagcag cagtgagctc catgtgcaga   1200
gaggcagggc tctggagtga gtggagccaa cctatttatg tgggaaatga tgaacacaag   1260
cccttgagag agtggttgt cattgtgatt atggcaacca tctgcttcat cttgttaatt   1320
```

-continued

```
ctctcgctta tctgtaaaat atgtcattta tggatcaagt tgtttccacc aattccagca    1380
ccaaaaagta atatcaaaga tctctttgta accactaact atgagaaagc tgggtccagt    1440
gagacggaaa ttgaagtcat ctgttatata gagaagcctg gagttgagac cctggaggat    1500
tctgtgtttt gactgtcact ttggcatcct ctgatgaact cacacatgcc tcagtgcctc    1560
agtgaaaaga acagggatgc tggctcttgg ctaagaggtg ttcagaattt aggcaacact    1620
caatttacct gcgaagcaat acacccagac acaccagtct tgtatctctt aaaagtatgg    1680
atgcttcatc caaatcgcct cacctacagc agggaagttg actcatccaa gcattttgcc    1740
atgttttttc tccccatgcc gtacagggta gcacctcctc acctgccaat ctttgcaatt    1800
tgcttgactc acctcagact ttcattcaca acagacagct tttaaggcta acgtccagct    1860
gtatttactt ctggctgtgc cgtttggctg tttaagctgc caattgtagc actcagctac    1920
catctgagga agaaagcatt ttgcatcagc ctggagtgaa ccatgaactt ggattcaaga    1980
ctgtcttttc tatagcaa                                                   1998
```

<210> SEQ ID NO 196
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 196
acccagcttt ctgcaaaaca                                                 20

<210> SEQ ID NO 197
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 197
tcaacattac ctcatagtta                                                 20

<210> SEQ ID NO 198
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 198
taaatgacat ctgaaaacag                                                 20

<210> SEQ ID NO 199
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 199
gaacacttac attttacaga                                                 20

<210> SEQ ID NO 200
<211> LENGTH: 20
<212> TYPE: DNA
<213> ORGANISM: Artificial Sequence
<220> FEATURE:

<223> OTHER INFORMATION: Description of Artificial Sequence:Synthetic

<400> SEQUENCE: 200
tcatcatttc ctggtggaaa                    20

<210> SEQ ID NO 201
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 201
tcatcattta ctggtggaaa                    20

<210> SEQ ID NO 202
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 202
tcagcattta ctggtgtaaa                    20

<210> SEQ ID NO 203
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 203
tcagcagtta cttgtgtaaa                    20

<210> SEQ ID NO 204
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 204
agcggcagag cattgagaac                    20

<210> SEQ ID NO 205
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 205
agcggcagag cattgagaac                    20

<210> SEQ ID NO 206
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 206
gaagcagcgg cagagcattg                    20

-continued

```
<210> SEQ ID NO 207
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 207
gaagcagcgg cagagcattg                                                    20

<210> SEQ ID NO 208
<211> LENGTH: 612
<212> TYPE: DNA
<213> ORGANISM: Homo sapiens

<400> SEQUENCE: 208
ggtaccagac ctgctcacaa agcagagaag agctaaggcg gttctctaag ggcagagaat        60
tgctgctatt gcctagtgag tggggagagg gtactcctca ggccttactt cctatcaaat       120
catgtgtcag tgttgcctag gagacagagg cacagtaact actgtagcca aacaaggcac       180
ataaacaaaa cagaaatgca acgctttaga gtacccacgg aaaacttgtt taccttgtca       240
ccatgagtaa aagttaattc ccactcctga agagagcaaa ccaactctga aagagagtga       300
aaatgcagac aagacagtta tcagataatg gctatctgga cgagagattc tttcgtttga       360
cagcagtttg gttgttggga gttccagttc agctcctgca cagttgctct gtacaaatcc       420
tcctccatat ttgcttagag aaaacgtgtt gccatcccat catgaaggaa gctgcctgag       480
agtttttaac cattacagcc gtgatgatga aagagtgaag aaccgcctct aagttaaaaa       540
gtgcacccag agataaggtt cgttctcaat gctctgccgc tgcttctcat cgcatggcca       600
ccgcatttct ca                                                          612
```

ANTISENSE MODULATION OF INTERLEUKIN-5 SIGNAL TRANSDUCTION

FIELD OF THE INVENTION

The present invention provides compositions and methods for modulating interleukin-5 (IL-5) signaling through antisense modulation of IL-5 and/or IL-5 receptor α (IL-5α) expression. In particular, this invention relates to antisense compounds, particularly oligonucleotides, specifically hybridizable with nucleic acids encoding IL-5 or IL-5Rα. Such oligonucleotides have been shown to modulate the expression of IL-5 and IL-5Rα, respectively.

BACKGROUND OF THE INVENTION

Cytokines are relatively low molecular weight, pharmacologically active proteins that are secreted by cells for the purpose of altering either their own functions or those of adjacent cells. Cytokines are important regulators of hematopoiesis. They exert their actions by binding to specific receptors on the cell surface. Among the cytokines are a large number of interleukins as well as growth and colony-stimulating factors. Interleukin-5 (IL-5) is a critical cytokine for regulation of growth, activation, maturation, and survival of eosinophils, a type of leukocyte, and their release from the bone marrow. Eosinophils have been implicated in the pathogenesis of certain diseases ("eosinophilic syndromes") characterized by long-term chronic inflammation of tissues, such as the lungs in the case of asthma or the muscles in the case of eosinophilia myalgia. Other eosinophilic syndromes in addition to these include allergic rhinitis and atopic dermatitis. Eosinophils have also been noted as a component of cellular infiltrates of malignant tumors. Eosinophils are attracted to sites of wounding or inflammation, where they undergo a process of activation. Because eosinophils play a seminal role in the pathogenesis of asthma, particularly the late-phase reaction of asthma, and other inflammatory and/or allergic conditions, IL-5 signal transduction is of clinical importance.

In humans, IL-5 is selective in specifically promoting eosinophil and basophilic differentiation and maturation. Blood and tissue eosinophilia is a characteristic abnormality in allergy and asthma and convincing evidence implicates IL-5 as the key cytokine regulating this selective eosinophilic inflammation. Thus, inhibition of IL-5 production or effector function will abolish the eosinophilic component in asthma and other eosinophilic diseases, likely preventing further tissue damage caused by release of eosinophil-specific inflammatory mediators and potentially providing clinical benefit. Indeed, it has been demonstrated neutralizing IL-5 with a monoclonal antibody can completely inhibit bronchoalveolar eosinophilia caused by allergen challenge in guinea pigs, mice, and monkeys. A correlation exists between pulmonary eosinophilia and asthma in man and it is clear that selective inhibition of IL-5 can block airway hyperresponsiveness in animal models.

Asthma is characterized by episodic airways obstruction, increased bronchial hyperresponsiveness, and airway inflammation. An association has been shown between the number of activated T cells and eosinophils in the airways and abnormalities in forced expiratory volume in one second (FEV1), a measure of pulmonary function, increased bronchial responsiveness, and clinical severity in asthma. It has been documented that both interleukin-5 (IL-5) mRNA and protein levels are increased in bronchial biopsies from both atopic and intrinsic asthmatics.

IL-5 interacts with cells via the IL-5 receptor (IL-5R) on the cell surface. The IL-5 receptor is a heterodimer of α- and β-subunits. The IL-5 receptorα-subunit is specific to IL-5R, whereas the β-subunit is common to IL-3, IL-5, and granulocyte/macrophage colony-stimulating factor (GM-CSF) receptors. The human IL-5 receptor (IL-5R) is expressed in vitro on eosinophils, basophils, and B lymphocytes, although its role on B cells remains in question. Besides a membrane anchored form, two forms of soluble human IL-5Rα are produced. Only the membrane form of the α chain is complexed with the β chain, which is required for signaling.

The link between T cell derived IL-5 and lung eosinophilia is further strengthened by the observation that increased levels of IL-5 receptorα mRNA are also found in bronchial biopsies from asthmatics and that the eosinophil is the predominant site of this increased IL-5Rα expression. Further, the subset of eosinophils that express the membrane bound form of the IL-5 receptor inversely correlates with FEV1 while the subset expressing the soluble form of the receptor directly correlates with FEV1. These observations suggest that IL-5 receptorα isoform expression is of central importance in determining clinical prognosis. The soluble form of the receptor may be serving a beneficial role in asthmatic patients. It is therefore presently believed that an effective therapeutic approach to preventing eosinophilia in asthma and other eosinophilic syndromes would entail selective inhibition of membrane but not soluble IL-5 receptor expression. In addition, there are several animal and lung explant models of allergen-induced eosinophilia, late phase airway responses, and bronchial hyperresponsiveness which collectively support a link between IL-5 and airway eosinophilia and decreased pulmonary function.

Several approaches to inhibition of IL-5 function have been tried. Chimeric, humanized and other interleukin-5 (IL-5) monoclonal antibodies (mAbs), and pharmaceutical compositions and therapeutic methods are disclosed in WO 96/21000. Ribozymes for cleaving IL-5 mRNA are disclosed in WO 95/23225. A 16mer phosphodiester oligo deoxynucleotide with two phosphorothioate linkages, targeted to IL-5 mRNA, was used to inhibit IL-5 secretion by human peripheral blood mononuclear cells. Weltman and Karim, *Allergy Asthma Proc.*, 1998, 19, 257–261; September–October 1998. Methods of treating airway disease by administering essentially adenosine-free antisense oligonucleotides to the airway epithelium are disclosed in WO 96/40162. IL-5 and IL-5 receptor are among the antisense targets disclosed.

Thus there remains a long felt need for compositions and methods for modulating IL-5 signal transduction, particularly in the treatment and prevention of asthma and other reactive airway disease.

SUMMARY OF THE INVENTION

The present invention is directed to antisense compounds, particularly oligonucleotides, which are targeted to a nucleic acid encoding IL-5 or IL-5Rα, and which modulate the expression of these gene targets. Pharmaceutical and other compositions comprising the antisense compounds of the invention are also provided. Further provided are methods of modulating the expression of IL-5 and/or IL-5Rα in cells or tissues comprising contacting said cells or tissues with one or more of the antisense compounds or compositions of the invention. Further provided are methods of modulating IL-5 signaling in cells or tissues comprising contacting said cells or tissues with one or more of the antisense compounds or compositions of the invention. Further provided are methods of treating an animal, particularly a human, suspected of having or being prone to a disease or condition associated with IL-5 signaling or with expression of IL-5 or IL-5Rα by administering a therapeutically or prophylactically effective amount of one or more of the antisense compounds or compositions of the invention.

DETAILED DESCRIPTION OF THE INVENTION

The present invention comprehends antisense compounds capable of modulating IL-5 signal transduction, preferably by modulating expression of IL-5 or IL-5 receptorα. These compounds are useful for both research and therapeutic, including prophylactic, uses.

The human IL-5 receptorα gene contains 14 exons. A membrane-anchored form of the receptor and two soluble forms have been identified. The mRNA transcript encoding the membrane-anchored form of the human IL-5 receptorα contain exons 1–10 and 12–14. Exon 11 is spliced out by an alternative splicing event. The major soluble isoform (soluble form 1) is generated as a result of a normal splicing event and an in-frame stop codon in exon 11. The other soluble form (soluble form 2) is generated by the absence of splicing and therefore is generated by reading into intron 11. Tuypens et al. *Eur. Cytokine Netw.*, 1992, 3, 451–459.

The mRNA encoding the membrane form of the mouse IL-5 receptorα contains 11 exons. The transmembrane domain of the receptor is encoded in exon 9. Two mRNAs encoding soluble (secreted) forms of the receptor result from differential splicing events. The mRNA encoding soluble form 1 of the receptor is missing exon 9 (exon 8 is spliced to exon 10) and the mRNA encoding soluble form 2 is missing exons 9 and 10 (exon 8 is spliced to exon 11). Imamura et al., *DNA and Cell Biol.*, 1994, 13, 283–292.

In both mouse and humans, there are both soluble forms and a membrane-bound form of IL-5 receptorα. In mouse, the soluble form is expressed, though experiments are usually done by addition of exogenous recombinant soluble receptor. Recombinant murine soluble IL-5 receptorα binds IL-5, and does not inhibit proliferation of the IL-5-responsive Y16B cell line. In vivo, recombinant soluble murine IL-5 receptorα suppresses antigen-induced airway eosinophilia. In humans, recombinant human soluble IL-5 receptorα binds human IL-5 and inhibits its biological activity in vitro, i.e., prevents TF-1 proliferation and survival. In other words, in the human system, the soluble IL-5 receptorα acts as a sponge to bind the IL-5 cytokine and block its effects. Only the membrane-bound form of IL-5 receptorα is able to transduce the IL-5 signal. Soluble human IL-5 receptorα is not normally detected in human biological fluids; however, a direct correlation has been observed between the expression of soluble human IL-5 receptorα and pulmonary function in asthmatic subjects.

The present invention employs oligomeric antisense compounds, particularly oligonucleotides, for use in modulating IL-5 signal transduction. In preferred embodiments this is done by modulating the function of nucleic acid molecules encoding IL-5 or IL-5Rα, ultimately modulating the amount of IL-5 or IL-5Rα produced. Antisense compounds are provided which specifically hybridize with one or more nucleic acids encoding IL-5 or IL-5Rα. In preferred embodiments used herein, the term "nucleic acid encoding IL-5" encompasses DNA encoding IL-5, RNA (including pre-mRNA and mRNA) transcribed from such DNA, and also cDNA derived from such RNA. Similarly the term "nucleic acid encoding IL-5Rα" encompasses DNA encoding IL-5Rα, RNA (including pre-mRNA and mRNA) transcribed from such DNA, and also cDNA derived from such RNA. In the context of the present invention, the term "nucleic acid target" encompasses nucleic acids encoding either IL-5 or IL-5Rα, according to which of these the antisense compound is complementary. The specific hybridization of an oligomeric compound with its target nucleic acid interferes with the normal function of the nucleic acid. This modulation of function of a target nucleic acid by compounds which specifically hybridize to it is generally referred to as "antisense". The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of IL-5 or IL-5Rα. In the context of the present invention, "modulation" means either an increase (stimulation) or a decrease (inhibition) in the expression of a gene. In the context of the present invention, inhibition is the preferred form of modulation of gene expression and mRNA is a preferred target.

It is preferred to target specific nucleic acids for antisense. "Targeting" an antisense compound to a particular nucleic acid, in the context of this invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding IL-5 or IL-5Rα. The targeting process also includes determination of a site or sites within this gene for the antisense interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding IL-5 or IL-5Rα, regardless of the sequence(s) of such codons.

It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which is known in the art to refer to the region between the translation initiation codon and the translation termination codon, is also a region which may be targeted effectively. Other target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene, and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA splice sites, i.e., intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for antisense compounds targeted, for example, to DNA or pre-mRNA.

Once one or more target sites have been identified, oligonucleotides are chosen which are sufficiently complementary to the target, i.e., hybridize sufficiently well and with sufficient specificity, to give the desired effect.

In the context of this invention, "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, and, in the case of in vitro assays, under conditions in which the assays are performed.

Antisense compounds are commonly used as research reagents and diagnostics. For example, antisense oligonucleotides, which are able to inhibit gene expression with exquisite specificity, are often used by those of ordinary skill to elucidate the function of particular genes. Antisense compounds are also used, for example, to distinguish between functions of various members of a biological pathway. Antisense modulation has, therefore, been harnessed for research use.

The specificity and sensitivity of antisense is also harnessed by those of skill in the art for therapeutic uses. Antisense oligonucleotides have been employed as therapeutic moieties in the treatment of disease states in animals and man. Antisense oligonucleotides have been safely and effectively administered to humans and numerous clinical trials are presently underway. It is thus established that oligonucleotides can be useful therapeutic modalities that can be configured to be useful in treatment regimes of cells, tissues and animals, especially humans. In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 8 to about 30 nucleobases. Particularly preferred are antisense oligonucleotides comprising from about 8 to about 30 nucleotides). As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2'-, 3'- or 5'-hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure. However, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative United States patents that teach the preparation of the above phosphorus-containing linkages include, but are not limited to, U.S. Pat. Nos.: 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos.: 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethyiglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos.: 5,539,082; 5,714,331; and 5,719,262, each of which is herein incorporated by reference. Further teaching of PNA compounds can be found in Nielsen et al., *Science*, 1991, 254, 1497–1500.

Most preferred embodiments of the invention are oligonucleotides with phosphorothioate backbones and oligonucleosides with heteroatom backbones, and in particular $-CH_2-NH-O-CH_2-$, $-CH_2-N(CH_3)-O-CH_2-$ [known as a methylene (methylimino) or MMI backbone], $-CH_2-O-N(CH_3)-CH_2-$, $-CH_2-N(CH_3)-N(CH_3)-CH_2-$ and $-O-N(CH_3)-CH_2-CH_2-$ [wherein the native phosphodiester backbone is represented as $-O-P-O-CH_2-$] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to about 10. Other preferred oligonucleotides comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes an alkoxyalkoxy group, 2'-methoxyethoxy (2'-O—$CH_2CH_2OCH_3$, also known as 2'-O-(2-methoxyethyl) or 2'-MOE) (Martin et al., *Helv. Chim. Acta*, 1995, 78, 486–504). Further preferred modifications include 2'-dimethylaminooxyethoxy, i.e., a 2'-O($CH_2)_2ON(CH_3)_2$ group, also known as 2'-DMAOE and 2'-dimethylaminoethoxyethoxy, i.e., 2'-O—$CH_2$—O—$CH_2$—$N(CH_3)_2$.

Other preferred modifications include 2'-methoxy (2'-O—$CH_3$), 2'-aminopropoxy (2'-O$CH_2CH_2CH_2NH_2$) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos.: 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,0531 5,639,873; 5,646,265; 5,658,873; 5,670,633; and 5,700,920, each of which is herein incorporated by reference.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in Kroschwitz, J. I., *The Concise Encyclopedia Of Polymer Science And Engineering*, ed. John Wiley & Sons, 1990, pages 858–859, those disclosed by Englisch et al., *Angewandte Chemie*, International Edition, 1991, 30, 613, and those disclosed by Sanghvi, Y. S., Crooke, S. T., and Lebleu, B. eds., *Antisense Research and Applications*, CRC Press, Boca Raton, 1993, pp. 289–302. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Sanghvi, Y. S., Crooke, S. T. and Lebleu, B., eds., *Antisense Research and Applications*, CRC Press, Boca Raton, 1993, pp. 276–278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos.: 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,681,941; and 5,750,692, each of which is herein incorporated by reference.

Another modification of the oligonucleotides of the invention involves chemically linking to the oligonucleotide one or more moieties or conjugates which enhance the activity, cellular distribution or cellular uptake of the oligonucleotide. Such moieties include but are not limited to lipid moieties such as a cholesterol moiety (Letsinger et al., *Proc. Natl. Acad. Sci. USA*, 1989, 86, 6553–6556), cholic acid (Manoharan et al., *Bioorg. Med. Chem. Let.*, 1994, 4, 1053–1060), a thioether, e.g., hexyl-S-tritylthiol (Manoharan et al.,*Ann. N.Y. Acad. Sci.*, 1992, 660, 306–309; Manoharan et al., *Bioorg. Med. Chem. Let.*, 1993, 3, 2765–2770), a thiocholesterol (Oberhauser et al., *Nucl. Acids Res.*, 1992, 20, 533–538), an aliphatic chain, e.g., dodecandiol or undecyl residues (Saison-Behmoaras et al., *EMBO J.*, 1991, 10, 1111–1118; Kabanov et al., *FEBS Lett.*, 1990, 259, 327–330; Svinarchuk et al., *Biochimie*, 1993, 75, 49–54), a phospholipid, e.g., di-hexadecyl-rac-glycerol or triethylammonium 1,2-di-O-hexadecyl-rac-glycero-3-H-phosphonate (Manoharan et al., *Tetrahedron Lett.*, 1995, 36, 3651–3654; Shea et al., *Nucl. Acids Res.*, 1990, 18, 3777–3783), a polyamine or a polyethylene glycol chain (Manoharan et al., *Nucleosides & Nucleotides*, 1995, 14, 969–973), or adamantane acetic acid (Manoharan et al., *Tetrahedron Lett.*, 1995, 36, 3651–3654), a palmityl moiety (Mishra et al., *Biochim. Biophys. Acta*, 1995, 1264, 229–237), or an octadecylamine or hexylaminocarbonyl-oxycholesterol moiety (Crooke et al., *J. Pharmacol. Exp. Ther.*, 1996, 277, 923–937.

Representative United States patents that teach the preparation of such oligonucleotide conjugates include, but are not limited to, U.S. Pat. Nos.: 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

It is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos.: 5,013,830; 5,149,797;

5,220,007; 5,256,775; 5,366,878; 5,403,711; 5,491,133; 5,565,350; 5,623,065; 5,652,355; 5,652,356; and 5,700,922, each of which is herein incorporated by reference.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

The antisense compounds of the invention are synthesized in vitro and do not include antisense compositions of biological origin, or genetic vector constructs designed to direct the in vivo synthesis of antisense molecules.

The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos.: 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense compounds of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl)phosphate] derivatives according to the methods disclosed in WO 93/24510 or in WO 94/26764.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., "Pharmaceutical Salts," *J. of Pharma Sci.*, 1977, 66, 1–19). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Preferred addition salts are acid salts such as the hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embolic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfoic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalene-disulfonic acid, polygalacturonic acid, and the like; and (d) salts formed from elemental anions such as chlorine, bromine, and iodine.

The antisense compounds of the present invention can be utilized for diagnostics, therapeutics, prophylaxis and as research reagents and kits. For therapeutics, an animal, preferably a human, suspected of having a disease or disorder which can be treated by modulating IL-5 signaling is treated by administering one or more antisense compounds in accordance with this invention. The compounds of the invention can be utilized in pharmaceutical compositions by adding an effective amount of an antisense compound to a suitable pharmaceutically acceptable diluent or carrier. Use of the antisense compounds and methods of the invention may also be useful prophylactically, e.g., to prevent or delay infection, inflammation or tumor formation, for example.

The antisense compounds of the invention are useful for research and diagnostics, because these compounds hybridize to nucleic acids encoding IL-5 or IL-5Rα, enabling sandwich and other assays to easily be constructed to exploit this fact. Hybridization of the antisense oligonucleotides of the invention with a nucleic acid encoding IL-5 or IL-5Rα can be detected by means known in the art. Such means may include conjugation of an enzyme to the oligonucleotide, radiolabelling of the oligonucleotide or any other suitable detection means. Kits using such detection means for detecting the level of IL-5 or IL-5Rα in a sample may also be prepared.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions and/or formulations comprising the oligonucleotides of the present invention may also include penetration enhancers in order to enhance the alimentary delivery of the oligonucleotides. Penetration enhancers may be classified as belonging to one of five broad categories, i.e., fatty acids, bile salts, chelating agents, surfactants and non-surfactants (Lee et al., *Critical Reviews in Therapeutic Drug Carrier Systems*, 1991, 8, 91–192; Muranishi, *Critical Reviews in Therapeutic Drug Carrier Systems*, 1990, 7, 1–33). One or more penetration enhancers from one or more of these broad categories may be included.

Various fatty acids and their derivatives which act as penetration enhancers include, for example, oleic acid, lauric acid, capric acid, myristic acid, palmitic acid, stearic acid, linoleic acid, linolenic acid, dicaprate, tricaprate, recinleate, monoolein (a.k.a. 1-monooleoyl-rac-glycerol), dilaurin, caprylic acid, arichidonic acid, glyceryl 1-monocaprate, 1-dodecylazacycloheptan-2-one, acylcarnitines, acylcholines, mono- and di-glycerides and physiologically acceptable salts thereof (i.e., oleate, laurate, caprate, myristate, palmitate, stearate, linoleate, etc.) (Lee et al., *Critical Reviews in Therapeutic Drug Carrier Systems*, 1991, 8:2, 91–192; Muranishi, *Critical Reviews in Therapeutic Drug Carrier Systems*, 1990, 7:1, 1–33; El-Hariri et al., *J. Pharm. Pharmacol.*, 1992, 44, 651–654). Examples of some presently preferred fatty acids are sodium caprate and sodium laurate, used singly or in combination at concentrations of 0.5 to 5%.

The physiological roles of bile include the facilitation of dispersion and absorption of lipids and fat-soluble vitamins (Brunton, Chapter 38 In: *Goodman & Gilman's The Pharmacological Basis of Therapeutics*, 9th Ed., Hardman et al., eds., McGraw-Hill, New York, N.Y., 1996, pages 934–935). Various natural bile salts, and their synthetic derivatives, act as penetration enhancers. Thus, the term "bile salt" includes any of the naturally occurring components of bile as well as any of their synthetic derivatives. A presently preferred bile salt is chenodeoxycholic acid (CDCA) (Sigma Chemical Company, St. Louis, Mo.), generally used at concentrations of 0.5 to 2%.

Complex formulations comprising one or more penetration enhancers may be used. For example, bile salts may be used in combination with fatty acids to make complex formulations. Preferred combinations include CDCA combined with sodium caprate or sodium laurate (generally 0.5 to 5%).

Chelating agents include, but are not limited to, disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines) (Lee et al., *Critical Reviews in Therapeutic Drug Carrier Systems*, 1991, 8:2, 92–192; Muranishi, *Critical Reviews in Therapeutic Drug Carrier Systems*, 1990, 7:1, 1–33; Buur et al., *J. Control Rel.*, 1990, 14, 43–51). Chelating agents have the added advantage of also serving as DNase inhibitors.

Surfactants include, for example, sodium lauryl sulfate, polyoxyethylene-9-lauryl ether and polyoxyethylene-20-cetyl ether (Lee et al., *Critical Reviews in Therapeutic Drug Carrier Systems*, 1991, 8:2, 92–191); and perfluorochemical emulsions, such as FC-43 (Takahashi et al., *J. Pharm. Pharmacol.*, 1988, 40, 252–257).

Non-surfactants include, for example, unsaturated cyclic ureas, 1-alkyl- and 1-alkenylazacyclo-alkanone derivatives (Lee et al., *Critical Reviews in Therapeutic Drug Carrier Systems*, 1991, 8:2, 92–191); and non-steroidal anti-inflammatory agents such as diclofenac sodium, indomethacin and phenylbutazone (Yamashita et al., *J. Pharm. Pharmacol.*, 1987, 39, 621–626).

As used herein, "carrier compound" refers to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioated oligonucleotide in hepatic tissue is reduced when it is coadministered with polyinosinic acid, dextran sulfate, polycytidic acid or 4-acetamido-4'-isothiocyano-stilbene-2,2'-disulfonic acid (Miyao et al., *Antisense Res. Dev.*, 1995, 5, 115–121; Takakura et al., *Antisense & Nucl. Acid Drug Dev.*, 1996, 6, 177–183).

In contrast to a carrier compound, a "pharmaceutically acceptable carrier" (excipient) is a pharmaceutically acceptable solvent, suspending agent or any other pharmacologically inert vehicle for delivering one or more nucleic acids to an animal. The pharmaceutically acceptable carrier may be liquid or solid and is selected with the planned manner of administration in mind so as to provide for the desired bulk, consistency, etc., when combined with a nucleic acid and the other components of a given pharmaceutical composition. Typical pharmaceutically acceptable carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrates (e.g., starch, sodium starch glycolate, etc.); or wetting agents (e.g., sodium lauryl sulphate, etc.). Sustained release oral delivery systems and/or enteric coatings for orally administered dosage forms are described in U.S. Pat. Nos. 4,704,295; 4,556,552; 4,309,406; and 4,309,404.

The compositions of the present invention may additionally contain other adjunct components conventionally found in pharmaceutical compositions, at their art-established usage levels. Thus, for example, the compositions may contain additional compatible pharmaceutically-active materials such as, e.g., antipruritics, astringents, local anesthetics or anti-inflammatory agents, or may contain additional materials useful in physically formulating various dosage forms of the composition of present invention, such as dyes, flavoring agents, preservatives, antioxidants, opacifiers, thickening agents and stabilizers. However, such materials, when added, should not unduly interfere with the biological activities of the components of the compositions of the invention.

In certain embodiments of this invention, the antisense compounds of the invention may be administered in combination with a conventional anti-asthma medication. Typically, two types of medication are used in attempts to control asthma: quick-relief medications (short-acting bronchodilators) that work fast to stop attacks or relieve symptoms and long-term preventive medications (especially anti-inflammatory agents) that keep symptoms and attacks from starting. Examples of the short-acting bronchodilators are short-acting β2-agonists, for example, albuterol, bitolterol, fenoterol isoetharine, metaproterenol, pirbuterol, salbutamol and terbutaline; anticholinergics, for example ipratropium bromide and oxitropium bromide; short-acting theophyllines, for example, aminophylline; and epinephrine/adrenaline. Examples of long-term preventive medications are inhaled or oral corticosteroids, for example, beclomethasone, budesonide, fluticasone triamcinolone, prednisolone, prednisone and methylprednisolone; sodium cromoglycate or cromolyn sodium; nedocromil; oral or inhaled long-acting β2-agonists, for example salmeterol, formoterol, terbutaline, salbutamol; sustained-release theophyllines, for example, aminophylline, methylxanthine and xanthine; and ketotifen. Antisense compounds of the present inventions may be administered in combination or conjunction with these or any of the asthma medications known in the art.

The compounds of the invention may also be administered in combination with another inhibitor of IL-5 signal transduction, preferably an antibody directed to IL-5. Such antibodies are known in the art.

Regardless of the method by which the antisense compounds of the invention are introduced into a patient, colloidal dispersion systems may be used as delivery vehicles to enhance the in vivo stability of the compounds and/or to target the compounds to a particular organ, tissue or cell type. Colloidal dispersion systems include, but are not limited to, macromolecule complexes, nanocapsules, microspheres, beads and lipid-based systems including oil-in-water emulsions, micelles, mixed micelles, liposomes and lipid:oligonucleotide complexes of uncharacterized structure. A preferred colloidal dispersion system is a plurality of liposomes. Liposomes are microscopic spheres having an aqueous core surrounded by one or more outer layer(s) made up of lipids arranged in a bilayer configuration (see, generally, Chonn et al., *Current Op. Biotech.*, 1995, 6, 698–708).

Certain embodiments of the invention provide for liposomes and other compositions containing (a) one or more antisense compounds and (b) one or more other chemotherapeutic agents which function by a non-antisense mechanism. Examples of such chemotherapeutic agents include, but are not limited to, anticancer drugs such as daunorubicin, dactinomycin, doxorubicin, bleomycin, mitomycin, nitrogen mustard, chlorambucil, melphalan, cyclophosphamide, 6-mercaptopurine, 6-thioguanine, cytarabine (CA), 5-fluorouracil (5-FU), floxuridine (5-FUdR), methotrexate (MTX), colchicine, vincristine, vinblastine, etoposide, teniposide, cisplatin and diethylstilbestrol (DES). See, generally, *The Merck Manual of Diagnosis and Therapy*, 15th Ed., Berkow et al., eds., 1987, Rahway, N.J., pp. 1206–1228. Anti-inflammatory drugs, including but not limited to nonsteroidal anti-inflammatory drugs and corticosteroids, and antiviral drugs, including but not limited to ribovirin, vidarabine, acyclovir and ganciclovir, may also be combined in compositions of the invention. See, generally, *The Merck Manual of Diagnosis and Therapy*, 15th Ed., Berkow et al., eds., 1987, Rahway, N.J., pp. 2499–2506 and 46–49, respectively. Other non-antisense chemotherapeutic agents are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Two or more combined compounds may be used together or sequentially.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in viva animal models. In general, dosage is from 0.01 μg to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 μg to 100 g per kg of body weight, once or more daily, to once every 20 years.

While the present invention has been described with specificity in accordance with certain of its preferred embodiments, the following examples serve only to illustrate the invention and are not intended to limit the same.

EXAMPLES

Example 1

Nucleoside Phosphoramidites for Oligonucleotide Synthesis

Deoxy and 2'-alkoxy Amidites

2'-Deoxy and 2'-methoxy β-cyanoethyldiisopropyl phosphoramidites were purchased from commercial sources (e.g. Chemgenes, Needham Mass. or Glen Research, Inc. Sterling Va.). Other 2'-O-alkoxy substituted nucleoside amidites are prepared as described in U.S. Pat. No. 5,506,351, herein incorporated by reference. For oligonucleotides synthesized using 2'-alkoxy amidites, the standard cycle for unmodified oligonucleotides was utilized, except the wait step after pulse delivery of tetrazole and base was increased to 360 seconds.

Oligonucleotides containing 5-methyl-2'-deoxycytidine (5-Me-C) nucleotides were synthesized according to published methods (Sanghvi, et. al., *Nucleic Acids Research*, 1993, 21, 3197–3203] using commercially available phosphoramidites (Glen Research, Sterling Va. or ChemGenes, Needham Mass.).

2'-Fluoro Amidites

2'-Fluorodeoxyadenosine Amidites

2'-fluoro oligonucleotides are synthesized as described previously by Kawasaki, et. al., *J. Med. Chem.*, 1993, 36, 831–841 and U.S. Pat. No. 5,670,633, herein incorporated by reference. Briefly, the protected nucleoside N6-benzoyl-2'-deoxy-2'-fluoroadenosine is synthesized utilizing commercially available 9-beta-D-arabinofuranosyladenine as starting material and by modifying literature procedures whereby the 2'-alpha-fluoro atom is introduced by a $S_N2$-displacement of a 2'-beta-trityl group. Thus N6-benzoyl-9-beta-D-arabinofuranosyladenine was selectively protected in moderate yield as the 3',5'-ditetrahydropyranyl (THP) intermediate. Deprotection of the THP and N6-benzoyl groups is accomplished using standard methodologies and standard methods are used to obtain the 5'-dimethoxytrityl-(DMT) and 5'-DMT-3'-phosphoramidite intermediates.

2'-Fluorodeoxyguanosine

The synthesis of 2'-deoxy-2'-fluoroguanosine is accomplished using tetraisopropyldisiloxanyl (TPDS) protected 9-beta-D-arabinofuranosylguanine as starting material, and conversion to the intermediate diisobutyryl-arabinofuranosylguanosine. Deprotection of the TPDS group is followed by protection of the hydroxyl group with THP to give diisobutyryl di-THP protected arabinofuranosylguanine. Selective O-deacylation and triflation is followed by treatment of the crude product with fluoride, then deprotection of the THP groups. Standard methodologies are used to obtain the 5'-DMT- and 5'-DMT-3'-phosphoramidites.

2'-Fluorouridine

Synthesis of 2'-deoxy-2'-fluorouridine is accomplished by the modification of a literature procedure in which 2,2'-anhydro-1-beta-D-arabinofuranosyluracil is treated with 70% hydrogen fluoride-pyridine. Standard procedures were used to obtain the 5'-DMT and 5'-DMT-3'phosphoramidites.

2'-Fluorodeoxycytidine

2'-deoxy-2'-fluorocytidine is synthesized via amination of 2'-deoxy-2'-fluorouridine, followed by selective protection to give N4-benzoyl-2'-deoxy-2'-fluorocytidine. Standard procedures are used to obtain the 5'-DMT and 5'-DMT-3'phosphoramidites.

2'-O-(2-Methoxyethyl) Modified Amidites

2'-O-Methoxyethyl-substituted nucleoside amidites were prepared as follows, or alternatively, as per the methods of Martin, P., *Helvetica Chimica Acta*, 1995, 78, 486–504.

2,2'-Anhydro[1-(beta-D-arabinofuranosyl)-5-methyluridine]

5-Methyluridine (ribosylthymine, commercially available through Yamasa, Choshi, Japan) (72.0 g, 0.279 M), diphenylcarbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 hours) to give a solid that was crushed to a light tan powder (57 g, 85% crude yield). The NMR spectrum was consistent with the structure, contaminated with phenol as its sodium salt (ca. 5%). The material was used as is for further reactions or purified further by column chromatography using a gradient of methanol in ethyl acetate (10–25%) to give a white solid, mp 222–4° C.

2'-O-Methoxyethyl-5-methyluridine 2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155–160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in $CH_3CN$ (600 mL) and evaporated. A silica gel column (3 kg) was packed in $CH_2Cl_2$/Acetone/MeOH (20:5:3) containing 0.5% $Et_3NH$. The residue was dissolved in $CH_2Cl_2$ (250 mL) and adsorbed onto silica (150 g) prior to loading onto the column. The product was eluted with the packing solvent to give 160 g (63%) of product. Additional material was obtained by reworking impure fractions.

2'-O-Methoxyethyl-5'-O-dimethoxytrityl-5-methyluridine

2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278M) was added and the reaction stirred for an additional one hour. Methanol (170 mL) was then added to stop the reaction. HPLC showed the presence of approximately 70% product. The solvent was evaporated and triturated with $CH_3CN$ (200 mL). The residue was dissolved in $CHCl_3$ (1.5 L) and extracted with 2×500 mL of saturated $NaHCO_3$ and 2×500 mL of saturated NaCl. The organic phase was dried over $Na_2SO_4$, filtered and evaporated. 275 g of residue was obtained. The residue was purified on a 3.5 kg silica gel column, packed and eluted with EtOAc/Hexane/Acetone (5:5:1) containing 0.5% $Et_3NH$. The pure fractions were evaporated to give 164 g of product. Approximately 20 g additional was obtained from the impure fractions to give a total yield of 183 g (57%).

3'-O-Acetyl-2'-O-methoxyethyl-5'-O-dimethoxytrityl-5-methyluridine

2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by tlc by first quenching the tlc sample with the addition of MeOH. Upon completion of the reaction, as judged by tlc, MeOH (50 mL) was added and the mixture evaporated at 35° C. The residue was dissolved in $CHCl_3$ (800 mL) and extracted with 2×200 mL of saturated sodium bicarbonate and 2×200 mL of saturated NaCl. The water layers were back extracted with 200 mL of $CHCl_3$. The combined organics were dried with sodium sulfate and evaporated to give 122 g of residue (approx. 90% product). The residue was purified on a 3.5 kg silica gel column and eluted using EtOAc/Hexane(4:1). Pure product fractions were evaporated to yield 96 g (84%). An additional 1.5 g was recovered from later fractions.

3'-O-Acetyl-2'-O-methoxyethyl-5'-O-dimethoxytrityl-5-methyl-4-triazoleuridine

A first solution was prepared by dissolving 3'-O-acetyl-2'-O-methoxyethyl-5'-O-dimethoxytrityl-5-methyluridine (96 g, 0.144 M) in $CH_3CN$ (700 mL) and set aside. Triethylamine (189 mL, 1.44 M) was added to a solution of triazole (90 g, 1.3 M) in $CH_3CN$ (1 L), cooled to −5° C. and stirred for 0.5 hours using an overhead stirrer. $POCl_3$ was added dropwise, over a 30 minute period, to the stirred solution maintained at 0–10° C., and the resulting mixture stirred for an additional 2 hours. The first solution was added dropwise, over a 45 minute period, to the latter solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of $NaHCO_3$ and 2×300 mL of saturated NaCl, dried over sodium sulfate and evaporated. The residue was triturated with EtOAc to give the title compound.

2'-O-Methoxyethyl-5'-O-dimethoxytrityl-5-methylcytidine

A solution of 3'-O-acetyl-2'-O-methoxyethyl-5'-O-dimethoxytrityl-5-methyl-4-triazoleuridine (103 g, 0.141 M) in dioxane (500 mL) and $NH_4OH$ (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with $NH_3$ gas was added and the vessel heated to 100° C. for 2 hours (tlc showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

N4-Benzoyl-2'-O-methoxyethyl-5'-O-dimethoxytrityl-5-methylcytidine

2'-O-Methoxyethyl-5'-O-dimethoxytrityl-5-methylcytidine (85 g, 0.134 M) was dissolved in DMF (800 mL) and benzoic anhydride (37.2 g, 0.165 M) was added with stirring. After stirring for 3 hours, tlc showed the reaction to be approximately 95% complete. The solvent was evaporated and the residue azeotroped with MeOH (200 mL). The residue was dissolved in $CHCl_3$ (700 mL) and extracted with saturated $NaHCO_3$ (2×300 mL) and saturated NaCl (2×300 mL), dried over $MgSO_4$ and evaporated to give a residue (96 g). The residue was chromatographed on a 1.5 kg silica column using EtOAc/Hexane (1:1) containing 0.5% $Et_3NH$ as the eluting solvent. The pure product fractions were evaporated to give 90 g (90%) of the title compound.

N4-Benzoyl-2'-O-methoxyethyl-5'-O-dimethoxytrityl-5-methylcytidine-3'-amidite

N4-Benzoyl-2'-O-methoxyethyl-5'-O-dimethoxytrityl-5-methylcytidine (74 g, 0.10 M) was dissolved in $CH_2Cl_2$ (1 L). Tetrazole diisopropylamine (7.1 g) and 2-cyanoethoxy-tetra-(isopropyl)phosphite (40.5 mL, 0.123 M) were added with stirring, under a nitrogen atmosphere. The resulting mixture was stirred for 20 hours at room temperature (tlc showed the reaction to be 95% complete). The reaction mixture was extracted with saturated $NaHCO_3$ (1×300 mL) and saturated NaCl (3×300 mL). The aqueous washes were back-extracted with $CH_2Cl_2$ (300 mL), and the extracts were combined, dried over $MgSO_4$ and concentrated. The residue obtained was chromatographed on a 1.5 kg silica column using EtOAc/Hexane (3:1) as the eluting solvent. The pure fractions were combined to give 90.6 g (87%) of the title compound.

Example 2

Oligonucleotide Synthesis

Unsubstituted and substituted phosphodiester (P=O) oligonucleotides are synthesized on an automated DNA synthesizer (Applied Biosystems model 380B) using standard phosphoramidite chemistry with oxidation by iodine.

Phosphorothioates (P=S) are synthesized as per the phosphodiester oligonucleotides except the standard oxidation bottle was replaced by 0.2 M solution of 3H-1,2-benzodithiole-3-one 1,1-dioxide in acetonitrile for the stepwise thiation of the phosphite linkages. The thiation wait step was increased to 68 seconds and was followed by the capping step. After cleavage from the CPG column and deblocking in concentrated ammonium hydroxide at 55° C. (18 hr), the oligonucleotides were purified by precipitating twice with 2.5 volumes of ethanol from a 0.5 M NaCl solution.

Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. No. 5,610,289 or U.S. Pat. No. 5,625,050, herein incorporated by reference.

Phosphoramidite oligonucleotides are prepared as described in U.S. Pat. No. 5,256,775 or U.S. Pat. No. 5,366,878, herein incorporated by reference.

Alkylphosphonothioate oligonucleotides are prepared as described in published PCT applications PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Example 3
Oligonucleoside Synthesis

Methylenemethylimino linked oligonucleosides, also identified as MMI linked oligonucleosides, methylenedimethylhydrazo linked oligonucleosides, also identified as MDH linked oligonucleosides, methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P=O or P=S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 4
PNA Synthesis

Peptide nucleic acids (PNAs) are prepared in accordance with any of the various procedures referred to in Peptide Nucleic Acids (PNA): Synthesis, Properties and Potential Applications, *Bioorganic & Medicinal Chemistry*, 1996, 4, 5–23. They may also be prepared in accordance with U.S. Pat. Nos. 5,539,082, 5,700,922, and 5,719,262, herein incorporated by reference.

Example 5
Synthesis of Chimeric Oligonucleotides

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

[2'-O-Me]—[2'-deoxy]—[2'-O-Me] Chimeric Phosphorothioate Oligonucleotides

Chimeric oligonucleotides having 2'-O-alkyl phosphorothioate and 2'-deoxy phosphorothioate oligonucleotide segments are synthesized using an Applied Biosystems automated DNA synthesizer Model 380B, as above. Oligonucleotides are synthesized using the automated synthesizer and 2'-deoxy-5'-dimethoxytrityl-3'-O-phosphoramidite for the DNA portion and 5'-dimethoxytrityl-2'-O-methyl-3'-O-phosphoramidite for 5' and 3' wings. The standard synthesis cycle is modified by increasing the wait step after the delivery of tetrazole and base to 600 s repeated four times for RNA and twice for 2'-O-methyl. The fully protected oligonucleotide is cleaved from the support and the phosphate group is deprotected in 3:1 Ammonia/Ethanol at room temperature overnight then lyophilized to dryness. Treatment in methanolic ammonia for 24 hours at room temperature is then done to deprotect all bases and sample was again lyophilized to dryness. The pellet is resuspended in IM TBAF in THF for 24 hours at room temperature to deprotect the 2' positions. The reaction is then quenched with 1 M TEAA and the sample is then reduced to ½ volume by rotovac before being desalted on a G25 size exclusion column. The oligo recovered is then analyzed spectrophotometrically for yield and for purity by capillary electrophoresis and by mass spectrometry.

[2'-O-(2-Methoxyethyl)]—[2'-deoxy]—[2'-O-(2-Methoxyethyl)] Chimeric Phosphorothioate Oligonucleotides

[2'-O-(2-methoxyethyl)]—[2'-deoxy]—[-2'-O-(methoxyethyl)] chimeric phosphorothioate oligonucleotides were prepared as per the procedure above for the 2'-O-methyl chimeric oligonucleotide, with the substitution of 2'-O-(methoxyethyl) amidites for the 2'-O-methyl amidites.

[2'-O-(2-Methoxyethyl)Phosphodiester]—[2'-deoxy Phosphorothioate]—[2'-O-(2-Methoxyethyl) Phosphodiester] Chimeric Oligonucleotides

[2'-O-(2-methoxyethyl phosphodiester]—[2'-deoxy phosphorothioate]—[2'-O-(methoxyethyl)phosphodiester] chimeric oligonucleotides are prepared as per the above procedure for the 2'-O-methyl chimeric oligonucleotide with the substitution of 2'-O-(methoxyethyl) amidites for the 2'-O-methyl amidites, oxidization with iodine to generate the phosphodiester internucleotide linkages within the wing portions of the chimeric structures and sulfurization utilizing 3, H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 6
Oligonucleotide Isolation

After cleavage from the controlled pore glass column (Applied Biosystems) and deblocking in concentrated ammonium hydroxide at 55° C. for 18 hours, the oligonucleotides or oligonucleosides were purified by precipitation twice out of 0.5 M NaCl with 2.5 volumes ethanol. Synthesized oligonucleotides were analyzed by polyacrylamide gel electrophoresis on denaturing gels and judged to be at least 85% full length material. The relative amounts of phosphorothioate and phosphodiester linkages obtained in synthesis were periodically checked by $^{31}$P nuclear magnetic resonance spectroscopy, and for some studies oligonucleotides were purified by HPLC, as described by Chiang et al., *J. Biol. Chem.* 1991, 266, 18162–18171. Results obtained with HPLC-purified material were similar to those obtained with non-HPLC purified material.

Example 7
Analysis of Oligonucleotide Inhibition of IL-5 or IL-5Rα Expression

Antisense modulation of IL-5 or IL-5Rα expression can be assayed in a variety of ways known in the art. For example, IL-5 or IL-5Rα mRNA levels can be quantitated by Northern blot analysis, RNAse protection assay (RPA), competitive polymerase chain reaction (PCR), or real-time PCR (RT-PCR). RNA analysis can be performed on total cellular RNA or poly(A)+ mRNA. Methods of RNA isolation are taught in, for example, Ausubel, et al., *Current Protocols in Molecular Biology*, Volume 1, John Wiley & Sons, Inc., 1993, pp. 4.1.1–4.2.9 and 4.5.1–4.5.3. Northern blot analysis is routine in the art and is taught in, for example, Ausubel, et al., *Current Protocols in Molecular Biology*, Volume 1, John Wiley & Sons, Inc., 1996, pp. 4.2.1–4.2.9. Real-time quantitative (PCR) can be conveniently accomplished using the commercially available ABI PRISMT™ 7700 Sequence Detection System, available from PE-Applied Biosystems, Foster City, Calif. and used according to manufacturer's instructions. Other methods of PCR are also known in the art.

IL-5 or IL-5Rα protein levels can be quantitated in a variety of ways well known in the art, such as immunoprecipitation, Western blot analysis (immunoblotting), ELISA, flow cytometry or fluorescence-activated cell sorting (FACS). Antibodies directed to IL-5 or IL-5Rα can be identified and obtained from a variety of sources, such as PharMingen Inc., San Diego Calif., or can be prepared via conventional antibody generation methods. Methods for preparation of polyclonal antisera are taught in, for example, Ausubel, et al., *Current Protocols in Molecular Biology*, Volume 2, John Wiley & Sons, Inc., 1997, pp. 11.12.1–11.12.9. Preparation of monoclonal antibodies is taught in, for example, Ausubel, et al., *Current Protocols in Molecular Biology*, Volume 2, John Wiley & Sons, Inc., 1997, pp. 11.4.1–11.11.5.

Immunoprecipitation methods are standard in the art and can be found at, for example, Ausubel, et al., *Current Protocols in Molecular Biology*, Volume 2, John Wiley & Sons, Inc., 1998, pp. 10.16.1–10.16.11. Western blot (immunoblot) analysis is standard in the art and can be found at, for example, Ausubel, et al., *Current Protocols in Molecular Biology*, Volume 2, John Wiley & Sons, Inc., 1997, pp. 10.8.1–10.8.21. Enzyme-linked immunosorbent assays (ELISA) are standard in the art and can be found at, for example, Ausubel, et al., *Current Protocols in Molecular Biology*, Volume 2, John Wiley & Sons, Inc., 1991, pp. 11.2.1–11.2.22.

Example 8

Poly(A)+ mRNA Isolation

Poly(A)+ mRNA is isolated according to Miura et al., *Clin. Chem.*, 1996, 42, 1758–1764. Other methods for poly(A)+ mRNA isolation are taught in, for example, Ausubel, et al., *Current Protocols in Molecular Biology*, Volume 1, John Wiley & Sons, Inc., 1993, pp. 4.5.1–4.5.3. Briefly, for cells grown on 96-well plates, growth medium is removed from the cells and each well is washed with 200 μL cold PBS. 60 μL lysis buffer (10 mM Tris-HCl, pH 7.6, 1 mM EDTA, 0.5 M NaCl, 0.5% NP-40, 20 mM vanadyl-ribonucleoside complex) is added to each well, the plate is gently agitated and then incubated at room temperature for five minutes. 55 μL of lysate is transferred to Oligo d(T) coated 96-well plates (AGCT Inc., Irvine Calif.). Plates are incubated for 60 minutes at room temperature, washed 3 times with 200 μL of wash buffer (10 mM Tris-HCl pH 7.6, 1 mM EDTA, 0.3 M NaCl). After the final wash, the plate is blotted on paper towels to remove excess wash buffer and then air-dried for 5 minutes. 60 μL of elution buffer (5 mM Tris-HCl pH 7.6), preheated to 70° C. is added to each well, the plate is incubated on a 90° C. hot plate for 5 minutes, and the eluate is then transferred to a fresh 96-well plate.

Cells grown on 100 mm or other standard plates may be treated similarly, using appropriate volumes of all solutions.

Example 9

Total RNA Isolation

Total mRNA is isolated using an RNEASY 96™ kit and buffers purchased from Qiagen Inc. (Valencia Calif.) following the manufacturer's recommended procedures. The kit can be used with cells grown on a variety of sizes of plate or bottle, including 96-well plates. Briefly, for cells grown on 96-well plates, growth medium is removed from the cells and each well is washed with 200 μL cold PBS. 100 μL Buffer RLT is added to each well and the plate vigorously agitated for 20 seconds. 100 μL of 70% ethanol is then added to each well and the contents mixed by pipetting three times up and down. The samples are then transferred to the RNEASY 96™ well plate attached to a QIAVAC™ manifold fitted with a waste collection tray and attached to a vacuum source. Vacuum is applied for 15 seconds. 1 mL of Buffer RW1 is added to each well of the RNEASY 96™ plate and the vacuum again applied for 15 seconds. 1 mL of Buffer RPE is then added to each well of the RNEASY 96™ plate and the vacuum applied for a period of 15 seconds. The Buffer RPE wash is then repeated and the vacuum is applied for an additional 10 minutes. The plate is then removed from the QIAVAC™ manifold and blotted dry on paper towels. The plate is then re-attached to the QIAVAC™ manifold fitted with a collection tube rack containing 1.2 mL collection tubes. RNA is then eluted by pipetting 60 μL water into each well, incubating 1 minute, and then applying the vacuum for 30 seconds. The elution step is repeated with an additional 60 μL water.

MOUSE IL-5

Example 10

Antisense Inhibition of Murine IL-5 Expression

In accordance with the present invention, a series of antisense oligonucleotides were designed to target different regions of murine IL-5 RNA, using published sequences (Genbank Accession No. X06271 incorporated herein as SEQ ID NO: 1). The oligonucleotides are shown in Table 1. Target sites are indicated by nucleotide numbers, as given in the sequence source reference (Genbank Accession No. X06271) to which the oligonucleotide binds. All compounds in Table 1 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings (shown in bold) are composed of 2'-O-methoxyethyl (2'-MOE) nucleotides. The internucleoside (backbone) linkages are phosphorothioate (P=S) throughout the oligonucleotide. Cytidine residues in the 2'-MOE regions are 5-methylcytidines but cytidines in the 2'-deoxy regions are unmodified unless otherwise indicated.

TABLE 1

Murine IL-5 Antisense Oligonucleotides

| ISIS NO. | NUCLEOTIDE SEQUENCE[1] (5' -> 3') | SEQ ID NO: | TARGET SITE[2] | TARGET REGION |
|---|---|---|---|---|
| 16975 | CCCAAGCAATTTATTCTCTC | 2 | 510–529 | 5'-UTR |
| 16976 | TCAGCAAAGGAAGAGCGCAG | 3 | 544–563 | Coding |
| 16977 | CACTGTGCTCATGGGAATCT | 4 | 654–673 | Coding |
| 16978 | ACTTTACCTCATTGCTTGTC | 5 | 718–737 | Coding |
| 16979 | TCAGAGCGGTATAGCAAGGT | 6 | 774–793 | Coding |
| 16980 | CTCATCGTCTGCAAAGGAAA | 7 | 1548–1567 | Coding |
| 16981 | TATGAGTAGGGACAGGAAGC | 8 | 1568–1587 | Coding |
| 16982 | ATTTTTATGAGTAGGGACAG | 9 | 1573–1592 | Coding |
| 16983 | AGCACGGCAGTAAAGAATAA | 10 | 1598–1617 | Coding |
| 16984 | ACAAGGAAAACAAAGAGAGG | 11 | 2380–2399 | Coding |
| 16985 | CTGGTGCTGAAAGAAGATTA | 12 | 3454–3473 | Coding |
| 16986 | CCACGGACAGTTTGATCCTT | 13 | 3513–3532 | Coding |
| 16987 | AATGACAGGTTTTGGAATAG | 14 | 3549–3568 | Coding |
| 16988 | GCGGTCAATGTATTCTTTA | 15 | 3571–3590 | Coding |
| 16989 | GGAACTTACTTTTTGGCGGT | 16 | 3586–3605 | Coding |
| 16990 | CAGACTGTCAGGTTGGCTCC | 17 | 3644–3663 | Coding |
| 16991 | TCCTCGCCACACTTCTCCTG | 18 | 3673–3692 | Coding |
| 16992 | AACTGCCTCGTCCTCCGTCT | 19 | 3694–3713 | Coding |
| 16993 | TACTCATCACACCAAGGAAC | 20 | 3732–3751 | Coding |
| 16994 | CTCAGCCTCAGCCTTCCATT | 21 | 3762–3781 | Stop |
| 16995 | TTAAATTGTGAAGTCCTGTC | 22 | 3794–3813 | 3'-UTR |
| 16996 | AAATATAAATGGAAACAGCA | 23 | 3874–3893 | 3'-UTR |
| 16997 | CTACAGGACATAAATATAAA | 24 | 3885–3904 | 3'-UTR |
| 16998 | TATACAAAAAGGTTAAACAC | 25 | 3938–3957 | 3'-UTR |
| 16999 | GGTTATCCTTCGCTACATTA | 26 | 4001–4020 | 3'-UTR |

[1]All linkages are phosphorothioate linkages. Residues shown in bold are 2'-methoxyethoxy, remaining residues are 2'-deoxy. All 2'-methoxyethoxy C residues are also 5-methyl C.
[2]Nucleotide numbers from Genbank Accession No. X06271, SEQ ID NO. 1 to which the oligonucleotide is targeted.

Oligonucleotides were tested in EL-4 T cells (ATCC TIB-39, American Type Culture Collection, Manassas Va.) by Northern blot analysis as described in previous examples using a commercially available murine IL-5 probe. These cells are PHA responsive and PMA plus cAMP elevating agents induce a several hundredfold increase in IL-5 synthesis by these cells. Cells were maintained and stimulated to express IL-5 according to published methods and transfected with oligonucleotide via electroporation.

Oligonucleotides were tested at a concentration of 10 μM. The results are shown in Table 2:

TABLE 2

Effect of Antisense Oligonucleotides on Murine IL-5 mRNA Levels

| ISIS NO. | SEQ ID NO: | TARGET REGION | % CONTROL | % INHIB |
|---|---|---|---|---|
| 16975 | 2 | 5' UTR | 89.4 | 10.6 |
| 16976 | 3 | Coding | 93.2 | 6.8 |
| 16977 | 4 | Coding | 107.8 | — |
| 16978 | 5 | Coding | 95 | 5 |
| 16979 | 6 | Coding | 96.9 | 3.1 |
| 16980 | 7 | Coding | 91 | 9 |
| 16981 | 8 | Coding | 55.8 | 44.2 |
| 16982 | 9 | Coding | 60 | 40 |
| 16983 | 10 | Coding | 67.6 | 32.4 |
| 16984 | 11 | Coding | 73.2 | 26.8 |
| 16985 | 12 | Coding | 71.6 | 28.4 |
| 16986 | 13 | Coding | 74.2 | 25.8 |
| 16987 | 14 | Coding | 104 | — |
| 16988 | 15 | Coding | 98.8 | 1.2 |
| 16989 | 16 | Coding | 107 | — |
| 16990 | 17 | Coding | 148 | — |
| 16991 | 18 | Coding | 107 | — |
| 16992 | 19 | Coding | 70 | 30 |
| 16993 | 20 | Coding | 78.1 | 21.9 |
| 16994 | 21 | Stop | 79.4 | 20.6 |
| 16995 | 22 | 3'-UTR | 95.7 | 4.3 |
| 16996 | 23 | 3'-UTR | 113 | — |
| 16997 | 24 | 3'-UTR | 122 | — |
| 16998 | 25 | 3'-UTR | 110 | — |
| 16999 | 26 | 3'-UTR | 68.1 | 31.9 |

SEQ ID NO 8, 9, 10, 19 and 26 (ISIS 16981, 16982, 16983, 16992 and 16999, respectively) showed at least 30% inhibition of IL-5 expression in this assay and are therefore preferred.

Example 11

Dose Response Comparison of ISIS 16992 and 16999 for Reduction of Murine IL-5 mRNA Levels ISIS 16992 and 16999 (SEQ ID NO: 19 and 26, respectively) were screened at concentrations of 5 to 25 μM in EL-4 T cells for the ability to decrease IL-5 mRNA levels. Oligonucleotides were introduced to cells by electroporation and mRNA levels were measured by Northern blot analysis. An IC50 (oligonucleotide concentration at which mRNA was decreased by 50% compared to control) of approximately 15 μM was obtained for ISIS 16992 and approximately 18 μM for ISIS 16999.

ISIS 16999 was compared to 1, 3, and 5-mismatch control sequences (ISIS Nos 17983, 17984 and 17985; SEQ ID Nos: 30, 31 and 32, respectively) in dose-response measurements of IL-5 mRNA levels after oligonucleotide treatment. In this experiment ISIS 16999 had an IC50 of approximately 9 μM and ISIS 17983, the 1-base mismatch control, had an IC50 of approximately 13 μM. IC50s were not obtainable for the 3- and 5-base mismatch controls which reduced IL-5 mRNA levels only by 8% and 17%, respectively.

Example 12
Dose Response Comparison of ISIS 16992 and 16999 for Reduction of Murine IL-5 Protein Levels ISIS 16992 and 16999 (SEQ ID NO: 19 and 26, respectively) were screened at concentrations of 5 to 25 μM in EL-4 T cells for the ability to decrease IL-5 protein levels. Oligonucleotides were introduced to cells by electroporation and protein levels were measured by ELISA assay using a murine IL-5 ELISA kit (Endogen, Woburn Mass.). Starting IL-5 concentrations in the absence of oligonucleotide were approximately 2300 pg/ml and this was decreased to approximately 200 pg/ml at 25 μM ISIS 16992 and 400 pg/ml at 25 μM ISIS 16999. An IC50 of approximately 13 μM was obtained for ISIS 16992 and approximately 15 μM for ISIS 16999.

Example 13
Effect of ISIS 16999 on IL-5 Secretion by EL-4 Cells

EL-4 cells were treated with ISIS 16999 at doses from 5 to 20 μM as described in previous examples. Secreted IL-5 in the medium was detected by ELISA assay as in previous examples.

Secreted IL-5 levels were reduced by 13.5-fold as oligonucleotide concentration was increased from zero to 10 μM. ISIS 16989, which did not reduce IL-5 mRNA levels (see Table 2 above), showed much lesser reduction (approximately 2.5-fold) in secreted IL-5 levels. IL-5 levels stayed low for at least 72 hours after treatment with ISIS 16999.

Example 14
Optimization of Antisense Inhibition of Murine IL-5 Expression

An additional series of oligonucleotides targeted to murine IL-5 was synthesized. The oligonucleotide sequences are those previously tested but with modified gap placement. Sequences are shown in Table 3. Target sites in this table refer back to the ISIS number of the parent compound of the same sequence shown in previous tables.

TABLE 3

Optimization of Antisense Modulation of Murine IL-5 Expression

| ISIS NO. | NUCLEOTIDE SEQUENCE[1] (5' -> 3') | SEQ ID NO: | TARGET SITE[2] | CHEMISTRY |
|---|---|---|---|---|
| 17858 | TATGAGTAGGGACAGGAAGC | 8 | ISIS 16981 | P = S; 2'-MOE |
| 17859 | TATGAGTAGGGACAGGAAGC | 8 | ISIS 16981 | P = S; 2'-MOE/ 2'-deoxy |
| 17860 | TATGAGTAGGGACAGGAAGC | 8 | ISIS 16981 | P = S; 2'-MOE/ 2'-deoxy |
| 17861 | TATGAGTAGGGACAGGAAGC | 8 | ISIS 16981 | P = S; 2'-MOE/ 2'-deoxy |
| 17862 | TATGAGTAGGGACAGGAAGC | 8 | ISIS 16981 | P = S; 2'-MOE/ 2'-deoxy |
| 17863 | AACTGCCTCGTCCTCCGTCT | 19 | ISIS 16992 | P = S; 2'-MOE |
| 17864 | AACTGCCTCGTCCTCCGTCT | 19 | ISIS 16992 | P = S; 2'-MOE/ 2'-deoxy |
| 17865 | AACTGCCTCGTCCTCCGTCT | 19 | ISIS 16992 | P = S; 2'-MOE/ 2'-deoxy |
| 17866 | AACTCCCTCGTCCTCCGTCT | 19 | ISIS 16992 | P = S; 2'-MOE/ 2'-deoxy |
| 17867 | AACTGCCTCGTCCTCCGTCT | 19 | ISIS 16992 | P = S; 2'-MOE/ 2'-deoxy |
| 17868 | GGTTATCCTTGGCTACATTA | 26 | ISIS 16999 | P = S; 2'-MOE |
| 17869 | GGTTATCCTTGGCTACATTA | 26 | ISIS 16999 | P = S; 2'-MOE/ 2'-deoxy |
| 17870 | CGTTATCCTTGGCTACATTA | 26 | ISIS 16999 | P = S; 2'-MOE/ 2'-deoxy |
| 17871 | GGTTATCCTTGGCTACATTA | 26 | ISIS 16999 | P = S; 2'-MOE/ 2'-deoxy |
| 17872 | GGTTATCCTTGGCTACATTA | 26 | ISIS 16999 | P = S; 2'MOE/ 2'-deoxy |
| 17980 | AACTGCCTCCTCCTCCGTCT | 27 | ISIS 16992 1mismatch | P = S; 2'-MOE/ 2'-deoxy; |
| 17981 | AACTGCCACCTGCTCCGTCT | 28 | ISIS 16992 3mismatch | P = S; 2'-MOE/ 2'-deoxy; |
| 17982 | AACTGGCACCTGCACCGTCT | 29 | ISIS 16992 5mismatch | P = S; 2'-MOE/ 2'-deoxy; |
| 17983 | GGTTATCCTAGGCTACATTA | 30 | ISIS 16999 1mismatch | P = S; 2'-MOE/ 2'-deoxy; |
| 17984 | GGTTATCGTAGCCTACATTA | 31 | ISIS 16999 3mismatch | P = S; 2'-MOE/ 2'-deoxy; |
| 17985 | GGTTAACGTAGCCAACATTA | 32 | ISIS 16999 5mismatch | P = S; 2'-MOE/ 2'-deoxy; |
| 17994 | AACTGCCTCCTCCTCCGTCT | 19 | ISIS 16992 | P = S; 2'-deoxy |
| 17995 | GGTTATCGTAGCCTACATTA | 26 | ISIS 16999 | P = S; 2'-deoxy |
| 18242 | GGTTATCCTTGGCTACATTA | 26 | ISIS 16999 | PS; 2'-MOE/ 2'-deoxy; |

TABLE 3-continued

Optimization of Antisense Modulation of Murine IL-5 Expression

| ISIS NO. | NUCLEOTIDE SEQUENCE[1] (5' -> 3') | SEQ ID NO: | TARGET SITE[2] | CHEMISTRY |
|---|---|---|---|---|
| 18243 | GGTTATCCTTGGCTACATTA | 26 | ISIS 16999 | All C = 5meC PS; 2'-MOE/2'-deoxy; |
| 18244 | AACTGCCTCGTCCTCCGTCT | 19 | ISIS 16992 | All C = 5meC PS; 2'-MOE/2'-deoxy; |
| 18245 | AACTGCCTCGTCCTCCGTCT | 19 | ISIS 16992 | All C = 5meC PS; 2'-MOE/2'-deoxy; |
| 18246 | TATGAGTAGGGACAGGAAGC | 8 | ISIS 16981 | All C = 5meC PS; 2'-MOE/2'-deoxy; |
| 18247 | TATGAGTAGGGACAGGAAGC | 8 | ISIS 16981 | All C = 5meC PS; 2'-MOE 2'-deoxy; |
| 20391 | GGTTATCCTTGGCTACATTA | 26 | ISIS 16999 | All C = 5meC PS; 2'-MOE/2'-deoxy; |
| 20392 | GGTTATCCTTGGCTACATTA | 26 | ISIS 16999 | All C = 5meC 2'-MOE/ P = O/2'-deoxy/P = S; |
| 20393 | GGTTAACGTAGCCAACATTA | 32 | ISIS 16999 5mismatch | All C = 5meC PS; 2'-MOE/2'-deoxy; |
| 20394 | GGTTAACGTAGCCAACATTA | 32 | ISIS 16999 5mismatch | All C = 5meC; 2'-MOE, P = O/2'-deoxy/P = S; |
| 20564 | GGTTATCCTTGGCTACATTA | 26 | ISIS 16999 | All C = 5meC; P = O; 2'-MOE/2'-deoxy; |
| 21437 | GGTTATCCTTGGCTACATTA | 26 | ISIS 16999 | All C = 5meC; P = S; 2'-MOE/2'-deoxy; 5'FITC |
| 21882 | GGTTATCCTTGGCTACATTA | 26 | ISIS 16999 | P = O; 2'-MOE/2'-deoxy; |
| 21966 | AACTGCCTCGTTCCTCCGTCT | 19 | ISIS 16992 | All C = 5meC; 2'-MOE P = O/2'-deoxy/P = S; |
| 21967 | AACTGCCTCGTCCTCCGTCT | 19 | ISIS 16992 | All C = 5meC; PS; 2'-MOE 2'-deoxy; |
| 21968 | AACTGCCTCGTCCTCCGTCT | 19 | ISIS 16992 | All C = 5meC P = O; 2'-MOE/2'-deoxy; |
| 21970 | GGTTAACGTAGCCAACATTA | 32 | ISIS 16999 5mismatch | All C = 5meC P = O; 2'-MOE/2'-deoxy; |
| 22087 | AACTGGCACCTGCACCGTCT | 29 | ISIS 16992 5mismatch | All C = 5meC; 2'-MOE, P = O/2'-deoxy/P = S; |
| 22088 | AACTGGCACCTGCACCGTCT | 29 | ISIS 16992 5mismatch | All C = 5meC; P = O; 2'-MOE/2'-deoxy; |
| 24232 | AACTGGCACCTGCACCGTCT | 29 | ISIS 16992 5mismatch | All C = 5meC; PS; 2'-MOE/2'-deoxy; All C = 5meC; |

[1]Emboldened residues, 2'-methoxyethoxy- residues (others are 2'-deoxy-). Unless otherwise indicated, 2'-MOE C residues are 5'-methyl-C (5meC) and 2'-deoxy C residues are unmodified.
[2]Target sites in this table refer back to the ISIS number of the compound of the same sequence shown in previous tables.

ISIS 17868, 17869, 17860, 18242 and 18243, all gap variants of ISIS 16999 (SEQ ID NO: 26), were tested and compared to the parent oligonucleotide, ISIS 16999 for ability to reduce IL-5 mRNA levels in EL-4 cells. In a screen at 15 $\mu$M oligonucleotide concentration (the IC50 for ISIS 16999), ISIS 18243 gave comparable activity to ISIS 16999.

ISIS 17870 and 18242 were slightly less active, ISIS 17869 showed modest activity and ISIS 17868 was virtually inactive. In a subsequent dose-response assay, ISIS 17870 and 18243 showed activity comparable to or slightly better than that of ISIS 16999.

ISIS 17858, 17859, 17860, 18246 and 18247, all gap variants of ISIS 16981 (SEQ ID NO: 8), were tested and compared to the parent oligonucleotide, ISIS 16981, for ability to reduce IL-5 mRNA levels in EL-4 cells. In a screen at 15 μM oligonucleotide concentration, ISIS 17859 and 18246 showed activity comparable to the parent, ISIS 16981, with ISIS 18247 only slightly less active. ISIS 17858 and 17860 were more active than the parent compound. All of the ISIS 16981 gap variants tested are therefore preferred.

ISIS 17863, 17864, 17865, 18244 and 18245, all gap variants of ISIS 16992 (SEQ ID NO: 19), were tested and compared to the parent oligonucleotide, ISIS 16992. In a screen at 15 μM oligonucleotide concentration, ISIS 18245 showed activity only slightly (approx 20%) less than the parent compound. ISIS 17863 and 18244 were modestly active and ISIS 17864 and 17865 were nearly inactive. Thus ISIS 18245 is also preferred.

ISIS 16999 was also compared to ISIS 20391, a compound of the same sequence, backbone and gap placement but with 5-methyl cytosines in place of every cytosine (in both the deoxy gap and the 2'-methoxyethoxy regions), and to ISIS 20392, which was identical to ISIS 20391 except the backbone was phosphodiester (P=O) in the 2' methoxyethoxy regions and phosphorothioate (P=S) in the deoxy gap. Oligos were compared at doses of 5, 15 and 25 μM for ability to reduce IL-5 mRNA levels in EL-4 cells. Both ISIS 20391 and 20392 showed roughly comparable activity to ISIS 16999, with 20392 slightly more active than the parent. Both of these compounds are therefore preferred. 5-base mismatches of both ISIS 20391 and 20392 were inactive at all concentrations. ISIS 20564, a full phosphodiester compound, was virtually inactive at these concentrations in a separate experiment.

Example 15

Effect of IL-5 Antisense Oligonucleotide ISIS 20391 on in Vivo T Cell IL-5 mRNA Expression IL-5 mRNA expression was measured in EL-4 T cells by real-time quantitative PCR using the TaqMan system on a Perkin-Elmer ABI PRISM 7700. Relative IL-5 levels were normalized to GAPDH levels. The primer and probe sequences were as follows:

Murine IL5:
Probe: 5'-6-FAM DYE-AG TGT TCT GAC TCT CAG CTG TGT CTG GGC-TAMRA DYE-3'(SEQ ID NO: 33)
Sense: 5'-TTC AGA GTC ATG AGA AGG ATG CTT-3' (SEQ ID NO: 34)
Antisense: 5' ACC ACT GTG CTC ATG GGA ATC T-3' (SEQ ID NO: 35)
GAPDH:
Probe: 5'-6-FAM DYE-AAG GCC GAG AAT GGG AAG CTT GTC ATC-TAMRA DYE-3'(SEQ ID NO: 36)
Sense: 5'-GGC AAA TTC AAC GGC ACA GT-3'(SEQ ID NO: 37)
Antisense: 5'-GGG TCT CGC TCC TGG AAG AT-3'(SEQ ID NO: 38).

ISIS 20391 reduced IL-5 mRNA levels by 75% compared to ovalbumin-induced IL-5 levels, whereas the mismatch oligonucleotide ISIS 20393 reduced IL-5 mRNA by only 40%.

Example 16

Effect of ISIS 20391 (targeted to murine IL-5) on Ovalbumin-induced Peritonitis in Balb/c Mice.

An eosinophil peroxidase (EPO) colorimetric assay was used to measure the effect of oligonucleotides on eosinophilia in peritoneal lavage fluid after ovalbumin immunization and challenge. The method used is a modification of Strath et al., J. Immunol. Meth., 1985, 83, 209–215. Briefly, the substrate solution consists of 0.05 M o-phenylenediamine dihydrochloride (OPD, Sigma Chem. Co., St. Louis, Mo.) in 0.05 M Tris buffer containing 1 mM hydrogen peroxide and 0.1% Triton X-100. Reaction mixture is added to cells, incubated in the dark for 30 minutes and the reaction was stopped by addition of ¼ volume of 4 M sulfuric acid. The EPO was measured as the absorbance at 492 nm, blanked against substrate solution. Using this assay, EPO levels are proportional to number of eosinophils present. Mice were dosed chronically with oligonucleotides. Ovalbumin challenge increased EPO levels in peritoneal lavage fluid over sixteenfold. ISIS 20391 dosed chronically at 5 mg/kg reduced EPO levels after ovalbumin induction by 47%. The mismatch control reduced EPO by approximately 12.6%.

A dose-dependent reduction of EPO by ISIS 20391 was obtained, with approximately 75% reduction at 10 mg/kg oligonucleotide dose compared to 29% reduction by the mismatch control. The IL-5 oligonucleotide correspondingly reduced eosinophil infiltration into the peritoneal cavity by 86% compared to the ovalbumin challenge control, while the mismatch only reduced infiltration by 26%. Using chronic subcutaneous administration (5 mg/kg/day for 15 days using implanted minipumps) a slight but reproducible inhibitory effect of the IL-5 oligonucleotide on eosinophilia in an ovalbumin lung challenge model has also been obtained.

Example 17

Reduction of IL-5 Protein in Peritoneal Lavage Fluid by ISIS 20391 Following 7 Day Dosing Schedule Mice were dosed daily with ISIS 20391 at 5 or 20 mg/kg for 7 days. Following peritoneal lavage, IL-5 protein levels were measured using an ELISA assay. IL-5 levels in ovalbumin-treated mice were approximately 160 pg/ml. Treatment with ISIS 20391 at 5 and 20 mg/kg reduced IL-5 concentrations in peritoneal fluid to 110 and 80 pg/ml, respectively. A control oligonucleotide at 5 and 20 mg/kg reduced IL-5 levels to 160 and 130 pg/ml.

Example 18

Effect of IL-5 Antisense Oligonucleotide on Ovalbumin-induced Murine Lung Asthma Model.

Airway inflammation is observed in patients with allergic asthma. A murine model of allergic asthma has been developed, (Hessel et al. J. Immunol. 1998, 160, 2998–3005). Sensitization of BALB/c mice with ovalbumin induces a high level of ovalbumin-specific IgE in serum. Inhalation of ovalbumin in sensitized mice causes an immediate bronchoconstrictive response. Repeated inhalation of ovalbumin in sensitized animals induces nonspecific airway hyperresponsiveness in vivo, and infiltration of leukocytes in airway tissue.

Pathogen-free male BALB/c ByJ mice were obtained from Jackson Laboratories. Active sensitization is performed by IP injection of 20 ug of ovalbumin (Sigma Chemical Co, St. Louis, Mo., grade II) in aluminum hydroxide adjuvant on days 2 and 9 of 16 days of daily oligonucleotide treatment. This produces high titers of total IgE in mouse serum of which 80% is ovalbumin-specific IgE (Hessel et al., J. Immunol., 1998, 160, 2998–3005). On day 16 of treatment, mice are exposed either 2% ovalbumin aerosol for 1 minute. The aerosol is generated with a nebulizer such as Medix 8001 (Sussex, UK). Oligonucleotides were dissolved in saline and injected daily i.v. in the tail vein by bolus infusion at the indicated doses from 2 days before antigen sensitization through challenge.

Bronchoalveolar lavage (BAL) is used to measure the leukocyte infiltration of airway tissue. 24 hours after the ovalbumin aerosol, mice were euthanized, tracheal cannulation was performed and saline washes collected. Percent eosinophils in BAL were determined.

Unsensitized mice had 1.6% eosinophils in BAL fluid; after ovalbumin sensitization this increased to 37.6%. ISIS 20391 at 5, 10 and 20 mg/kg reduced eosinophilia in BAL to 11.8%, 5.5% and 3.8%, respectively. The latter two are statistically significant reductions. Mismatch control oligonucleotide ISIS 20393 at 10 and 20 mg/kg yielded BAL eosinophil counts of 33.6% and 28.4%, respectively. The positive control, dexamethasone, reduced eosinophil counts to 5.8%.

Airway responsiveness to methacholine is measured in vivo 24 hours after the last aerosol exposure. Baseline nebulized methacholine dose response curves were constructed at day 0 before antigen sensitization for all groups of animals. Pulmonary function was monitored using a Buxco BioSystem Plethysmograph (Buxco, Troy N.Y.) and expressed as enhanced pause (Penh) which correlates to measured airway resistance (Hamelmann et al., *Am. J.Respir. Crit. Care Med.*, 1997, 156, 766–775). Following challenge with aerosolized albumin, pulmonary function recordings were performed for 30 minutes to examine the early phase allergic response. For the late phase reaction, recordings were performed every hour from 2 hours to 9 hours after ovalbumin challenge. Airway responsiveness was measured at 24 hours after antigen challenge by measuring the airway response to methacholine for 3 minutes at each dose. Post-challenge recordings were compared to baseline recordings for each group to generate a Penh stimulation index. As a positive control, dexamethasone was administered i.p., 25 mg/kg, 1 day before the sensitization, 2 hours before the challenge, and 18 hours after the challenge.

Plethysmography results showed that ISIS 20391 at 10 or 20 mg/kg inhibited the methacholine-induced allergic airway hyperresponsiveness, reducing the peak Penh index from approximately 2.0 (no oligo) to approximately 1.25 after oligonucleotide treatment in several experiments. Dexamethasone, the positive control, reduced the Penh to approximately 1.0.

Data from one experiment was expressed another way, in terms of PC100, (provocation challenge$_{100}$) the concentration of methacholine needed to give a twofold increase in airway hyperreactivity. Unsensitized mice had a PC100 of 40.1 mg/ml methacholine. After ovalbumin sensitization, the PC100 was 9.84, indicating that much lower doses of methacholine caused the same increase in airway reactivity. This effect was reversible in part by ISIS 20391. At 5 mg/kg ISIS 20391 the PC100 was 10.6, but at 10 and 20 mg/kg the PC100 was increased to 30.7 and 41.6 mg/kg showing a reverse in airway hyperreactivity. Dexamethasone had a PC100 of 29.8 mg/kg methacholine.

Example 19

Early and Late Phase Allergic Airway Response in Mouse Whole Body Plethysmography Model Ovalbumin challenge produces a two-phased response with separate and distinct peaks in airway hyperreactivity at approximately 2 minutes and approximately 2 hours after ovalbumin challenge. The first peak is about a twofold increase in Penh and the second peak is larger, a three- to four-fold increase in Penh. The late phase response was mitigated by ISIS 20391 at doses of 10 and 20 mg/kg. In particular, the late response, in which Penh reaches approximately 0.7 two hours after ovalbumin challenge (compared to 0.25 for unsensitized mice) was reduced by ISIS 20391 at 10 mg/kg to a Penh of approximately 0.4, which was a statistically significant reduction. Dexamethasone reduced the Penh to approximately 0.3. The mismatch control, ISIS 20393 at 10 mg/kg showed a statistically insignificant reduction of late phase Penh to approximately 0.5. In a higher-dose experiment, ISIS 20391 at 20 mg/kg reduced the Penh 2 hours after ovalbumin challenge from 0.7 to 0.425, which was statistically significant. Mismatch control ISIS 20393 at 20 mg/kg reduced Penh to approximately 0.6 which was not significant, and dexamethasone (positive control) reduced the response to approximately 0.25.

HUMAN IL-5

Example 20

Human IL-5 Antisense Oligonucleotides

A series of antisense compounds were designed to target mRNA coding human IL-5. These compounds are shown in Table 4.

TABLE 4

Nucleotide Sequences of Human IL-5 Oligonucleotides

| ISIS NO: | NUCLEOTIDE SEQUENCE (5' -> 3') | SEQ ID NO: | TARGET SITE[2] | TARGET REGION |
|---|---|---|---|---|
| 16071 | CTTTGGCAAAGAAAGTGCAT | 39 | 0509–0528 | 5'-UTR |
| 16072 | CGTTCTGCGTTTGCCTTTGG | 40 | 0523–0542 | 5'-UTR |
| 16073 | TCCTCATGGCTCTGAAACGT | 41 | 0540–0559 | AUG |
| 16074 | AAGAAAATTACCTCATTGGC | 42 | 0688–0707 | Coding |
| 16075 | TTACAGCACACCAGCATTCA | 43 | 0857–0876 | Coding |
| 16076 | TCCTCAGAGTCTGGAGAGGA | 44 | 0895–0914 | Coding |
| 16077 | GGAACAGGAATCCTCAGAGT | 45 | 0905–0924 | Coding |
| 16078 | TTTAACTTACATTTTTATGT | 46 | 0928–0947 | Coding |
| 16079 | TTTACTTATTCATGCCATCA | 47 | 0964–0983 | Coding |
| 16080 | GACACGATGCTCTTTGGGAA | 48 | 1161–1180 | Coding |
| 16081 | CATTTTAATATGACCAGGCA | 49 | 1407–1426 | Coding |
| 16082 | TTCTAGGCAACAAACCACCA | 50 | 1627–1646 | Coding |
| 16083 | ACAGTTGGTGCTAAATGAGG | 51 | 1873–1892 | Coding |
| 16084 | TTCTTCAGTGCACAGTTGGT | 52 | 1884–1903 | Coding |

TABLE 4-continued

Nucleotide Sequences of Human IL-5 Oligonucleotides

| ISIS NO: | NUCLEOTIDE SEQUENCE (5' -> 3') | SEQ ID NO: | TARGET SITE[2] | TARGET REGION |
|---|---|---|---|---|
| 16085 | ACCCCCTTGCACAGTTTGAC | 53 | 1932–1951 | Coding |
| 16086 | TGGCCGTCAATGTATTTCTT | 54 | 1988–2007 | Coding |
| 16087 | TGTAACTTACTTTTTGGCCG | 55 | 2002–2021 | Coding |
| 16088 | TCCATAGAAATAGGCACAGC | 56 | 2051–2070 | Coding |
| 16089 | CACACTTTTTCTGTGAAAAA | 57 | 2108–2127 | Coding |
| 16090 | ATTGGTTTACTCTCCGTCTT | 58 | 2135–2154 | Coding |
| 16091 | TTATCCACTCGGTGTTCATT | 59 | 2186–2205 | Coding |
| 16092 | TCCTTCTCCTCCAAAATCTT | 60 | 2241–2260 | 3'-UTR |
| 16093 | TGGCCCTCATTCTCACTGCA | 61 | 2269–2288 | 3'-UTR |
| 16094 | TCTGGCAAAGTGTCAGTATG | 62 | 2352–2371 | 3-'UTR |
| 16095 | TTGCCTGGAGGAAAATACTT | 63 | 2416–2435 | 3'-UTR |
| 16096 | CTTTGGCAAAGAAAGTGCAT | 64 | 0509–0528 | 5'-UTR |
| 16097 | CGTTCTGCGTTTGCCTTTGG | 65 | 0523–0542 | 5'-UTR |
| 16098 | AAGAAAATTACCTCATTGGC | 66 | 0688–0707 | Coding |
| 16099 | TCCTCAGAGTCTGGAGAGGA | 67 | 0895–0914 | Coding |
| 16100 | TTTAACTTACATTTTTATGT | 68 | 0928–0947 | Coding |
| 16101 | ACAGTTGGTGCTAAATGAGG | 69 | 1873–1892 | Coding |
| 16102 | TGTAACTTACTTTTTGGCGG | 70 | 2002–2021 | Coding |
| 16103 | CACACTTTTTCTGTGAAAAA | 71 | 2108–2127 | Coding |
| 17986 | TCTGGCAAACTGTCAGTATG | 72 | mismatch | 16094 |
| 17987 | TCTGGCATACTCTCAGTATG | 73 | mismatch | 16094 |
| 17988 | TCTGGGATACTCTGAGTATG | 74 | mismatch | 16094 |
| 17989 | TTGCCTGGACGAAAATACTT | 75 | mismatch | 16095 |
| 17990 | TTGCCTGCACGTAAATACTT | 76 | mismatch | 16095 |
| 17991 | TTGCCAGCACGTATATACTT | 77 | mismatch | 16095 |

[1]Emboldened residues, 2'-methoxyethoxy- residues (others are 2'-deoxy-) including "C" residues, 5-methyl-cytosines; all linkages are phosphorothioate linkages.
[2]Nucleotide numbers from Genbank Accession No. X12706, locus name "HSBCDIFFI", SEQ ID NO. 78 to which the oligonucleotide is targeted.

These oligonucleotides were electroporated into human HSB-2 cells and tested for effect on IL-5 mRNA by Northern blot analysis as described in previous examples. The HSB-2 T-cell line was obtained from the American Type Culture Collection and cells are cultured according to ATCC recommendations. They produce IL-5 upon induction with PMA+ionomycin. Oligonucleotides were tested by Northern blot analysis at a concentration of 10 μM for their ability to block IL-5 mRNA expression. The results are shown in Table 5.

TABLE 5

Activity of Antisense Oligonucleotides Targeted to Human IL-5

| ISIS NO. | SEQ ID NO: | TARGET REGION | % CONTROL | % INHIB |
|---|---|---|---|---|
| 16071 | 39 | 5'-UTR | 124 | — |
| 16072 | 40 | 5'-UTR | 93.1 | — |
| 16073 | 41 | AUG | 101 | — |
| 16074 | 42 | Coding | 146 | — |
| 16075 | 43 | Coding | 144 | — |
| 16076 | 44 | Coding | 296 | — |
| 16077 | 45 | Coding | 157 | — |
| 16078 | 46 | Coding | 166 | — |
| 16079 | 47 | Coding | 75 | 25 |
| 16080 | 48 | Coding | 224 | — |
| 16081 | 49 | Coding | 215 | — |
| 16082 | 50 | Coding | 94.3 | 5.7 |
| 16083 | 51 | Coding | 110 | — |
| 16084 | 52 | Coding | 22.2 | 77.8 |
| 16085 | 53 | Coding | 45.4 | 54.6 |
| 16086 | 54 | Coding | 158 | — |
| 16087 | 55 | Coding | 98.7 | 1.3 |
| 16088 | 56 | Coding | 88.4 | 11.6 |
| 16089 | 57 | Coding | 139 | — |
| 16090 | 58 | Coding | 72 | 28 |
| 16091 | 59 | Coding | 125 | — |
| 16092 | 60 | 3'-UTR | nd | nd |
| 16093 | 61 | 3'-UTR | 78.5 | 21.5 |
| 16094 | 62 | 3-'UTR | 58.1 | 41.9 |
| 16095 | 63 | 3'-UTR | 157 | — |
| 16096 | 64 | 5'-UTR | 164 | — |
| 16097 | 65 | 5'-UTR | 286 | — |
| 16098 | 66 | Coding | 117 | — |
| 16099 | 67 | Coding | 157 | — |
| 16100 | 68 | Coding | 163 | — |
| 16101 | 69 | Coding | 94.4 | 5.6 |
| 16102 | 70 | Coding | 109 | — |
| 16103 | 71 | Coding | 172 | — |

ISIS 16084, 16085 and 16094 inhibited IL-5 mRNA expression by at least 40%.

A dose-response curve was generated for inhibition of human IL-5 protein expression in HSB-2 cells by ISIS 16085. Cells untreated with oligonucleotide were found to express approximately 47 pg/ml IL-5. After treatment with ISIS 16085 at 5, 15 and 25 μM doses, IL-5 levels dropped to 21, 0 and 0 pg/ml, respectively. Treatment with a 1-mismatch control oligonucleotide at 5, 15 and 25 μM doses gave IL-5 levels of 26, 25 and 20 pg/ml, respectively. Treatment with a 3-mismatch control oligonucleotide at 5, 15 and 25 μM doses gave IL-5 levels of 52, 48 and 46 pg/ml, respectively. A 5-mismatch oligonucleotide did not inhibit, and at some doses stimulated, IL-5 protein expression.

Example 21
Inhibition of IL-5 Expression by ISIS 16085 in Human CEM T Cells Using an RNAse protection assay (Riboquant™ hCK4, Pharmingen, La Jolla Calif.), it was determined that ISIS 16085 inhibited IL-5 expression in a second T cell line, CEM (obtained from American Type Culture Collection) with an IC50 estimated at approximately 25 µM. IL-5 expression is induced in these cells by treatment with PMA plus ionomycin in the presence of IL-2, anti-CD28 crosslinking antibody, and dibutyryl cAMP. Dose response analysis of ISIS 16085 vs. its 5-mismatch control in stimulated CEM cells showed a dose-dependent decrease in IL-5 mRNA of about 50% at 25 µM oligonucleotide, compared with about 22% reduction with the mismatch control. No decreases were seen in other cytokine gene products measured in this assay panel.

Example 22
Optimization of Oligonucleotides Targeted to Human IL-5

Additional 2'-methoxyethoxy gapmer oligonucleotides were designed to optimize placement and size of 2' deoxy regions. These are shown in Table 6.

TABLE 6

Nucleotide Analogues of Human IL-5 Oligonucleotides

| ISIS NO. | NUCLEOTIDE SEQUENCE (5' -> 3') | SEQ ID NO: | TARGET SITE[2] | TARGET REGION |
|---|---|---|---|---|
| 16090 | ATTGGTTTACTCTCCGTCTT | 58 | 2135–2154 | Coding |
| 17873 | ATTGGTTTACTCTCCGTCTT | " | " | " |
| 17874 | ATTGGTTTACTCTCCGTCTT | " | " | " |
| 17875 | ATTGGTTTACTCTCCGTCTT | " | " | " |
| 17876 | ATTGGTTTACTCTCCGTCTT | " | " | " |
| 17877 | ATTGGTTTACTCTCCGTCTT | " | " | " |
| 16094 | TCTGGCAAAGTGTCAGTATG | 62 | 2352–2371 | 3'-UTR |
| 17878 | TCTGGCAAAGTGTCAGTATG | 62 | " | " |
| 17879 | TCTGGCAAAGTGTCAGTATG | " | " | " |
| 17880 | TCTGGCAAAGTGTCAGTATG | " | " | " |
| 17881 | TCTGGCAAAGTGTCAGTATG | " | " | " |
| 17882 | TCTGGCAAAGTGTCAGTATG | " | " | " |
| 17992 | TCTGGCAAAGTGTCAGTATG | " | " | " |
| 16095 | TTGCCTGGAGGAAAATACTT | 63 | 2416–2435 | 3'-UTR |
| 17883 | TTGCCTGGAGGAAAATACTT | " | " | " |
| 17884 | TTGCCTGGAGGAAAATACTT | " | " | " |
| 17885 | TTGCCTGGAGGAAAATACTT | " | " | " |
| 17886 | TTGCCTGGAGGAAAATACTT | " | " | " |
| 17887 | TTGCCTGGAGGAAAATACTT | " | " | " |
| 17993 | TTGCCTGGAGGAAAATACTT | " | " | " |
| 18248 | TTGCCTGGAGGAAAATACTT | " | " | " |
| 18249 | TTGCCTGGAGGAAAATACTT | " | " | " |
| 18250 | TCTGGCAAAGTGTCAGTATG | 62 | 2352–2371 | 3'-UTR |
| 18251 | TCTGGCAAAGTGTCAGTATG | " | " | " |
| 18252 | ATTGGTTTACTCTCCGTCTT | 58 | 2135–2154 | Coding |
| 18253 | ATTGGTTTACTCTCCGTCTT | " | " | " |

[1]Emboldened residues, 2'-methoxyethoxy- residues (others are 2'-deoxy-) including "C" residues, 5-methyl-cytosines; all linkages are phosphorothioate linkages.
[2]Nucleotide numbers from Genbank Accession No. X12706, locus name "HSBCDIFFI", SEQ ID NO. 78 to which the oligonucleotide is targeted.

TABLE 7

Nucleotide Analogues of Human IL-5 Oligonucleotides

Mixed backbone [phosphorothioate (P=S) and phosphodiester (P=O)] or all-phosphodiester (P=O) backbone analogs of ISIS 16095 and its mismatch control were also designed. These are shown in Table 7.

TABLE 7

| ISIS NO. | NUCLEOTIDE SEQUENCE[1] (5' -> 3') | SEQ ID NO: | TARGET REGION |
|---|---|---|---|
| 21883 | TTGCCTGGAGGAAAATACTT | 64 | mixed backbone; P = O in 2' MOE regions and P = S in 2'deoxy gap |
| 22103 | TTGCCAGCACGTATATACTT | 77 | mixed backbone; P = O in 2' MOE regions and P = S in 2'deoxy gap; 21883 mismatch |
| 23114 | TTGCCTGGAGGAAAATACTT | 63 | P = O throughout |
| 23115 | TTGCCAGCACGTATATACTT | 77 | P = O throughout; 23114 mismatch |

[1]Emboldened residues, 2'-methoxyethoxy-residues (others are 2'-deoxy-); all "C" and "C" residues, 5-methyl-cytosines; linkages in 2'-deoxy gaps are phosphorothioate linkages, linkages in 2'-MOE regions are phosphodiester linkages.

MOUSE IL-5 RECEPTOR
Example 23
Mouse IL-5 Receptorα Oligos

The mRNA encoding the membrane form of the mouse IL-receptorα contains 11 exons. The transmembrane domain of the receptor is encoded in exon 9. Two mRNAs encoding soluble (secreted) forms of the receptor result from differential splicing events. The mRNA encoding soluble form 1 of the receptor is missing exon 9 (exon 8 is spliced to exon 10) and the mRNA encoding soluble form 2 is missing exons 9 and 10 (exon 8 is spliced to exon 11). Imamura et al., *DNA and Cell Biology*, 13, 283–292.

Murine BCL$_1$ cells were chosen for screening antisense oligonucleotides targeted to murine IL-5 receptorα. These are B-cell leukemia cells derived from a spontaneously arising tumor of BALB/c origin, and proliferate in response to murine or human IL-5. This is a CD5+ line which resembles a subset of human chronic lymphocytic leukemia tumors and secretes IgM upon lipopolysaccharide stimulation. Cells were obtained from the American Type Culture Collection and cultured in RPMI 1640 medium supplemented with 10% heat-inactivated fetal bovine serum (Sigma Chemical Co., St. Louis, Mo.), 10 mM Hepes, pH 7.2, 50 μM 2-ME, 2 mM L-glutamine, 100 U/ml penicillin and 100 μg/ml streptomycin (Gibco, Grand Island, N.Y.)

A series of antisense oligonucleotides were designed to target the murine IL-5 receptor. All are chimeric "gapmers" with 2'-methoxyethoxy flanks and central 10-base deoxy "gaps" and a phosphorothioate backbone throughout. Cells ($1 \times 10^7$ cells in PBS) were transfected with oligonucleotides by electroporation at 200V, 1000 μF using a BTX Electro Cell Manipulator 600 (Genetronics, San Diego Calif.). Antisense oligonucleotide sequences are shown in Table 8.

TABLE 8

Nucleotide sequences of mouse IL-5 receptorα oligonucleotides

| ISIS NO. | NUCLEOTIDE SEQUENCE (5' -> 3') | NO: | TARGET SITE | TARGET REGION |
|---|---|---|---|---|
| 16924 | GACCTGTCCAGTGAGCTTCT | 79 | 0112–0131[2] | 5'-UTR |
| 16925 | TAGCCGAATACTGGAAAGGT | 80 | 0281–0300 | 5'-UTR |
| 16926 | AACACAGGCACCATGGTAGC | 81 | 0297–0316 | AUG |
| 16927 | CTCTTGGTCAGGATTTGGGT | 82 | 0445–0464 | Coding |
| 16928 | TCCTCACGCTAGCTGCAAAG | 83 | 0572–0591 | Coding |
| 16929 | ATGGCCTTAAGTGGGTGTGG | 84 | 0719–0738 | Coding |
| 16930 | GAGCCATTAATGTGCACAGC | 85 | 0927–0946 | Coding |
| 16931 | TCCACTCGCCCCACCTTCCT | 86 | 1250–1269 | Coding |
| 16932 | AACAAGACGAAGCAGGCAGC | 87 | 1338–1357 | Coding |
| 16933 | CCGGAACCGGTGGAAACAAC | 88 | 1400–1419 | Coding |
| 16934 | CCAACCTCTTCCACACAATG | 89 | 1500–1519 | Coding |
| 16935 | TCCCATGACTTCAAATCCAA | 90 | 1516–1535 | Coding |
| 16936 | GCAAAATGCCATCAAAACGT | 91 | 1542–1561 | STOP |
| 16937 | CGAGCTCTACCACCGCCTGG | 92 | 1651–1670 | 3'-UTR |
| 16938 | CAAGCTGGCCTCGAACTCAG | 93 | 1712–1731 | 3'-UTR |
| 16939 | GGATGGGTTGGTGACTTGCA | 94 | 1835–1854 | 3'-UTR |
| 16940 | TGAGGAAACCAAAGGCCCAT | 95 | 1946–1965 | 3'-UTR |
| 16941 | TGTCTCCCACTTGCGTCAGG | 96 | 2164–2183 | 3'-UTR |
| 16942 | TTGAACAGGCCTATGGAACA | 97 | 2306–2325 | 3'-UTR |
| 16943 | TCTTTTTCACCCCAGGCACG | 98 | 2359–2378 | 3'-UTR |
| 16944 | AATTCCCATGGATCCTCTTG | 99 | 2515–2534 | 3'-UTR |
| 16945 | ATCCAGCAATCACCTCCAAA | 100 | 2794–2813 | 3'-UTR |
| 16946 | TGTTCAGCCCATCAAAAAGA | 101 | 2984–3003 | 3'-UTR |
| 16947 | ATTTGGCTGACAGGACCCCG | 102 | 3140–3159 | 3'-UTR |
| 16948 | TCCAGAGACTGCCCCACCCA | 103 | 3216–3235 | 3'-UTR |
| 16949 | CATCTGCTTCTGTATTGCCA | 104 | 3381–3400 | 3'-UTR |
| 16950 | CCTTTTAGCTCCTTGGGTAC | 105 | 3456–3475 | 3'-UTR |
| 16951 | CATTTCTGAGGGTTGCTGGG | 106 | 3513–3532 | 3'-UTR |
| 18278 | CATCTGATTGTGTCTTGCCA | 107 | mismatch | 16949 |
| 18279 | CATCTGCTTGTGTATTGCCA | 108 | " | " |
| 18280 | CACCTGATTGTGTCTTGTCA | 109 | " | " |
| 17652 | TGTCCCTCCTTTTGGTGGGG | 110 | 0741–0760[3] | Coding |
| 17653 | TTAGCTCTGTGTCTGCTGAT | 111 | 0071–0090 | Coding |
| 17654 | AACTGCTGGCCAGAGTTGTA | 112 | 0611–0630 | Coding |
| 17655 | CATAGTTAAAGCAATGATCT | 113 | 1091–1110 | Coding |
| 17656 | GTTTCTCATATTCAGTAACC | 114 | 1451–1470 | Coding |
| 17657 | GGAGTCCTGTATGAGTTCAT | 115 | 1571–1590 | 3'-UTR |
| 17658 | TCTGTGCATCCCAGGTGCTG | 116 | 1681–1700 | 3'-UTR |
| 17659 | CTGGCTGTCCTGGAACTCAC | 117 | 1741–1760 | 3'-UTR |
| 17660 | TTCAAGGTAAGTCAAGCAAC | 118 | 2001–2020 | 3'-UTR |
| 17661 | CTGATGGCTACCACTGGCAA | 119 | 2081–2100 | 3'-UTR |
| 17662 | CACTCTCAATGAGTTCTATC | 120 | 2121–2140 | 3'-UTR |
| 17663 | TGATGCTGGTTGATCAATCT | 121 | 2411–2430 | 3'-UTR |
| 17664 | TCAATAGGGAATGGTGTCTT | 122 | 2681–2700 | 3'-UTR |
| 17665 | TTCCAGAGTACCTAGAAGCC | 123 | 2741–2760 | 3'-UTR |
| 17666 | CCAACAGGTTGCCATGAAGG | 124 | 2851–2870 | 3'-UTR |
| 17667 | AGAGATTAGAATTGACTAAG | 125 | 2881–2900 | 3'-UTR |
| 17668 | ACTATTGCATATACTAGCAA | 126 | 3161–3180 | 3'-UTR |
| 17669 | CCATCCAATATACAACCACC | 127 | 3191–3210 | 3'-UTR |
| 17670 | CTCATGGAAGGAGTTACAGA | 128 | 3271–3290 | 3'-UTR |
| 17671 | TGTGGATACTTCACTGCTTC | 129 | 3311–3330 | 3'-UTR |
| 17672 | ATCCAATAGATGACTGTGAG | 130 | 3401–3420 | 3'-UTR |
| 17673 | GTTCATATTGTTGTTCCTGC | 131 | 3491–3510 | 3'-UTR |

[1]Emboldened residues, 2'-methoxyethoxy- residues (others are 2'-deoxy-) including "C" residues, 5-methyl-cytosines; all linkages are phosphorothioate linkages.
[2]Nucleotide numbers from Genbank Accession No. D90205, locus name "MUSIL5R", SEQ ID NO. 132 to which the oligonucleotide is targeted.

TABLE 8-continued

Nucleotide sequences of mouse IL-5 receptorα oligonucleotides

| ISIS NO. | NUCLEOTIDE SEQUENCE (5' -> 3') | TARGET NO: | TARGET SITE | TARGET REGION |
|---|---|---|---|---|

[3]Nucleotide numbers from Genbank Accession No. S69702, locus name "S69702", SEQ ID NO. 133 to which the oligonucleotide is targeted.

Total cellular RNA was isolated using the RNeasy™ kit (Qiagen, Santa Clara Calif.). mRNA was analyzed by RNAse protection assay (RPA) using the Riboquant Kit and a customized riboprobe spanning exon 9 of the IL-5 receptorα (PharMingen, La Jolla Calif.). The cDNA probes were generated from oligonucleotides matching the exon sequences of either exons 2, 8,9 or 10. Signals were quantitated using a Molecular Dynamics PhosphorImager. Results are shown in Table 9.

TABLE 9

Antisense inhibition of mouse IL-5 receptorα mRNA expression

| ISIS NO. | SEQ ID NO: | TARGET REGION | % CONTROL | % INHIB |
|---|---|---|---|---|
| 16924 | 79 | 5'-UTR | 98 | 2 |
| 16925 | 80 | 5'-UTR | 86 | 14 |
| 16926 | 81 | AUG | 75 | 25 |
| 16927 | 82 | Coding | 74 | 26 |
| 16928 | 83 | Coding | 91 | 9 |
| 16929 | 84 | Coding | 87 | 13 |
| 16930 | 85 | Coding | 90 | 10 |
| 16931 | 86 | Coding | 108 | — |
| 16932 | 87 | Coding | 93 | 7 |
| 16933 | 88 | Coding | 102 | — |
| 16934 | 89 | Coding | 55 | 45 |
| 16935 | 90 | Coding | 108 | — |
| 16936 | 91 | STOP | 76 | 24 |
| 16937 | 92 | 3'-UTR | 91 | 9 |
| 16938 | 93 | 3'-UTR | 80 | 20 |
| 16939 | 94 | 3'-UTR | 83 | 17 |
| 16940 | 95 | 3'-UTR | 81 | 19 |
| 16941 | 96 | 3'-UTR | 98 | 2 |
| 16942 | 97 | 3'-UTR | 91 | 9 |
| 16943 | 98 | 3'-UTR | 81 | 19 |
| 16944 | 99 | 3'-UTR | 88 | 12 |
| 16945 | 100 | 3'-UTR | 65 | 35 |
| 16946 | 101 | 3'-UTR | 82 | 18 |
| 16947 | 102 | 3'-UTR | 75 | 25 |
| 16948 | 103 | 3'-UTR | 89 | 11 |
| 16949 | 104 | 3'-UTR | 52 | 48 |
| 16950 | 105 | 3'-UTR | 87 | 13 |
| 16951 | 106 | 3'-UTR | 99 | 1 |

In this assay, ISIS 16926, 16927, 16934, 16936, 16945, 16947 and 16949 gave at least approximately 25% inhibition of IL-5Rα mRNA expression and are preferred. Of these, ISIS 16934, 16945 and 16949 gave at least 35% inhibition and are more preferred.

ISIS 16934, 16945 and 16949 were chosen for further study. These demonstrated IC50s for inhibition of murine IL-5 receptorα mRNA in BCL$_1$ cells of approximately 2.5 μM, 1.5 μM and 1 μM, respectively. ISIS 16949 was tested for effects on IL-5 receptorα protein expression and showed nearly complete inhibition.

Example 24
Antisense Oligonucleotides Targeted to Exon 9 of Mouse IL-5 Receptor α

A series of antisense oligonucleotides were designed to "walk" the entire exon 9 of the coding region of murine IL-5 receptorα mRNA. Oligonucleotides were targeted to regions starting approximately every 10 nucleobases along the exon 9 sequence, which extends from nucleotides 1288 to 1381 on the sequence given as Genbank accession no. D90205. Oligonucleotides are shown in Table 10.

TABLE 10

Nucleotide Sequences of Mouse IL-5R Oligonucleotides-2' MOE gapmers

| ISIS NO. | NUCLEOTIDE SEQUENCE (5' -> 3') | SEQ ID NO: | TARGET SITE[2] | TARGET REGION |
|---|---|---|---|---|
| 18001 | CAAGGACTTCCTTTCCTTTC | 134 | 1288–1307 | Coding /exon 9 |
| 18002 | GCCATTCTACCAAGGACTTC | 135 | 1298–1317 | Coding /exon 9 |
| 18003 | ACAATGAGATGCCATTCTAC | 136 | 1308–1327 | Coding /exon 9 |
| 18004 | TGTTGGGAGCACAATGAGAT | 137 | 1318–1337 | Coding /exon 9 |
| 18005 | AGCAGGCAGCTCTTGGGAGC | 138 | 1328–1347 | Coding /exon 9 |
| 18006 | TGAGAACATTAACAAGACGA | 139 | 1348–1367 | Coding /exon 9 |
| 18007 | TGCAGATGAGTCAGAAGATT | 140 | 1358–1377 | Coding /exon 9 |
| 18008 | ACTCTGCAGATGAGTGAGAA | 141 | 1362–1381 | Coding /exon 9 |

[1]Emboldened residues, 2'-methoxyethoxy-residues (others are 2'-deoxy-) including "C" residues, 5-methyl-cytosines; all linkages are phosphorothioate linkages.
[2]Nucleotide numbers from Genbank Accession No. D90205, locus name "MUSIL5R," to which the oligonucleotide is targeted.

Effect of these compounds on both membrane and soluble forms of murine IL-5 receptorα were measured and are shown in Table 11. Oligonucleotides were screened in BCL$_1$ cells at a dose of 10 μM and IL-5 receptorα mRNA was measured by RPA. Percent inhibition is compared to untreated (no oligonucleotide) control.

TABLE 11

Effect of 2'-MOE gapmers targeted to murine IL-5 receptorα mRNA exon 9 on membrane and soluble IL-5 receptorα mRNA expression

| ISIS NO. | % inhibition of membrane IL-5 Rα | % inhibition of soluble[1] IL-5 Rα | SEQ ID NO: |
|---|---|---|---|
| 18001 | 35 | 39 | 134 |
| 18002 | 5 | 8 | 135 |

TABLE 11-continued

Effect of 2'-MOE gapmers targeted to murine IL-5 receptorα mRNA exon 9 on membrane and soluble IL-5 receptorα mRNA expression

| ISIS NO. | % inhibition of membrane IL-5 Rα | % inhibition of soluble[1] IL-5 Rα | SEQ ID NO: |
|---|---|---|---|
| 18003 | 15 | 20 | 136 |
| 18004 | 10 | 20 | 137 |
| 18005 | 55 | 59 | 138 |
| 18006 | 59 | 65 | 139 |
| 18007 | 65 | 65 | 140 |
| 18008 | 75 | 75 | 141 |

[1]Only one soluble form is detectable by RPA; the RPA probe does not distinguish between the two soluble forms. These gapmers were able to reduce both membrane and soluble forms and each oligonucleotide reduced the two forms approximately equally.

Example 25
Effect of Fully 2'-MOE Oligonucleotides Targeted to Murine IL-5 Receptorα mRNA Exon 9 on Membrane and Soluble IL-5 Receptorα mRNA Expression Additional oligonucleotides were designed to target exon 9 and intron/exon boundaries; these were uniformly 2'-methoxyethoxy modified with phosphorothioate backbones throughout. These are shown in Table 12 below.

TABLE 12

Nucleotide Sequences of Mouse IL-5R Oligonucleotides-uniform 2' MOE

| ISIS NO. | NUCLEOTIDE SEQUENCE (5' -> 3') | SEQ ID NO: | TARGET SITE | TARGET REGION |
|---|---|---|---|---|
| 21750 | GACTTCCTTTCCTTTCCTGG | 142 | 1284–1303[2] | I8/E9 |
| 21751 | CAAGGACTTCCTTTCCTTTC | 134 | 1288–1307 | 18001 |
| 21752 | GCCATTCTACCAAGGACTTC | 135 | 1298–1317 | 18002 |
| 21753 | ACAATGAGATGCCATTCTAC | 136 | 1308–1327 | 18003 |
| 21754 | TGTTGGGAGCACAATGAGAT | 137 | 1318–1337 | 18004 |
| 21755 | AGCAGGCAGCTGTTGGGAGC | 138 | 1328–1347 | 18005 |
| 21756 | AACAAGACGAAGCAGGCAGC | 143 | 1338–1357 | Exon 9 |
| 21757 | TGAGAAGATTAACAAGACGA | 139 | 1348–1367 | 18006 |
| 21758 | TGCAGATGAGTGAGAAGATT | 140 | 1358–1377 | 18007 |
| 21759 | ACTCTGCAGATGAGTGAGAA | 141 | 1362–1381 | 18008 |
| 21760 | CTACACTCTGCAGATGAGTG | 144 | 1366–1383 | E9/E10 |
| 21761 | CGATCAGTTTTTCCTTCTAA | 145 | 1145–1164[3] | E7/E8 |
| 21762 | TCACCCACATAAATAGGTTG | 146 | 1272–1288 | E8/E9 |
| 21763 | GGTCCATAAATGACACCTGA | 147 | 1382–1397 | E9/E10 |
| 21764 | TTACCTCATATTCAGTAACC | 148 | 1451–1466 | E10/E11 |
| 23235 | GCCATTCTATCAAGGACTTC | 149 | mismatch | 21752 |
| 23236 | GCCATGCTATCAAGCACTTC | 150 | " | " |
| 23237 | GCTATCCTATCAAGCACGTC | 151 | " | " |
| 23238 | GACTTCCTTACCTTTCCTGG | 152 | mismatch | 21750 |
| 23239 | GACTTCCTCTTCTTCCCTGG | 153 | " | " |
| 23240 | GACCTCTTTCCCTCTTCTGG | 154 | " | " |

[1]Emboldened residues, 2'-methoxyethoxy-residues (others are 2'-deoxy-) including "C" residues, 5-methyl-cytosines; all linkages are phosphorothioate linkages.
[2]Co-ordinates from Genbank Accession No. D90205, locus name "MUSIL5R", SEQ ID NO. 132.
[3]ISIS 21761–21764 were designed to hybridize to intron-exon border sequences provided in Table 1 of Imamura, F., et al., DNA Cell Biol., 1994, 13, 283–292

BCL$_1$ cells were treated with 10 μM of the full-2'-methoxyethoxy, full phosphorothioate oligonucleotides for 24 hours and total RNA was extracted and analyzed by RPA. Results are shown in Table 13.

TABLE 13

Effect of 2' MOE uniformly modified oligonucleotides targeted to murine IL-5 receptorα mRNA exon on IL-5 mRNA

| ISIS NO. | % control membrane IL-5 Rα | % inhib'n membrane IL-5 Rα | % control soluble IL-5 Rα | % inhib'n soluble IL-5 Rα | SEQ ID NO: |
|---|---|---|---|---|---|
| 21750 | 8 | 92 | 197 | — | 142 |
| 21751 | 9 | 91 | 191 | — | 134 |
| 21752 | 6 | 94 | 194 | — | 135 |
| 21753 | 6 | 94 | 175 | — | 136 |
| 21754 | 8 | 92 | 184 | — | 137 |
| 21755 | 16 | 84 | 181 | — | 138 |
| 21756 | 6 | 94 | 166 | — | 143 |
| 21757 | 19 | 81 | 144 | — | 139 |
| 21758 | 31 | 69 | 116 | — | 140 |
| 21759 | 34 | 66 | 134 | — | 141 |
| 21760 | 55 | 45 | 116 | — | 144 |

[1]Emboldened residues, 2'-methoxyethoxy-residues (others are 2'-deoxy-) including "C" residues, 5-methyl-cytosines; all linkages are phosphorothioate linkages.

All of the fully modified 2'-methoxyethoxy oligonucleotides targeted to murine IL-5 receptorα mRNA exon reduced expression of the membrane form of IL-5 receptorα and increased expression of the soluble form of the receptor. The potencies of these concurrent effects were coordinately diminished as the antisense target site moved toward the 3' end of the exon. The overall amount of IL-5 receptorα transcription is unaffected. This demonstrates that fully 2'-methoxyethoxy-modified oligonucleotides targeted to exon 9 just distal to the intronic 3' splice acceptor site blocked inclusion of exon 9 in the splice product and redirect the splicing machinery to the next downstream splice acceptor site (in intron 9). Reduction of the membrane form of IL-5 receptorα, particularly with no decrease or more particularly with an increase in the soluble form, is believed to have therapeutic utility in diseases associated with IL-5 signal transduction, especially asthma. These results show that splicing has been redirected by use of uniformly 2'-methoxyethoxy oligonucleotides targeted to exon 9 to cause exclusion (skipping) of exon 9 from the spliced mRNA products, resulting in controlled alteration of the ratio of soluble/membrane IL-5 receptor produced.

It was also shown that conversion of an RNAse H-dependent compound (the 2' MOE gapmer ISIS 18002) to an RNAse H-independent compound (the fully-2' MOE compound 21752) converted this oligonucleotide sequence from an inhibitor of both forms of IL-5 receptorα to one which selectively inhibits of the membrane form via splice redirection.

ISIS 21752 was chosen for further study. In dose response experiments, an IC50 of approximately 4 μM was obtained for inhibition of the membrane form of IL-5 receptorα mRNA. A 1-base mismatch (ISIS 23235) gave an IC50 of approximately 10.5 μM and 3- and 5-base mismatches did not inhibit membrane IL-5 receptor mRNA at any concentration.

Example 26
Oligonucleotides Targeted to Exon-exon Boundaries of Various Forms of Mouse IL-5 Receptorα mRNA.

Oligonucleotides, either 2' MOE gapmers or uniform 2' MOE, were designed to target exon-exon boundaries of the mature IL-5 receptorα mRNA. The mRNA encoding the membrane form of the mouse IL-5 receptorα contains 11 exons. The transmembrane domain of the receptor is encoded in exon 9. Two mRNAs encoding soluble (secreted) forms of the receptor result from differential splicing events. The mRNA encoding soluble form 1 of the receptor is missing exon 9 (exon 8 is spliced to exon 10) and the mRNA encoding soluble form 2 is missing exons 9 and 10 (exon 8 is spliced to exon 11). In Table 14, the target region designated "E7–E8" indicates that the oligonucleotide is targeted to the exon 7–8 boundary, and so forth.

TABLE 14

Nucleotide Sequences of Mouse IL-5R Oligonucleotides

| ISIS NO. | NUCLEOTIDE SEQUENCE (5' -> 3") | SEQ ID NO: | TARGET SITE[2] | TARGET REGION |
|---|---|---|---|---|
| 21847 | GTTTTTCCTTCTGAATGTGA | 155 | 1139–1158 | E7–E8 |
| 21848 | GTTTTTCCTTCTGAATGTGA | " | | 21847 |
| 21849 | CTTTCCTTTCCCACATAAAT | 156 | 1278–1297 | E8–E9 |
| 21850 | CTTTCCTTTCCCACATAAAT | " | | 21849 |
| 21851 | TAAATGACACACTCTGCAGA | 157 | 1372–1391 | E9–E10 |
| 21852 | TAAATGACACACTCTGCAGA | " | | 21851 |
| 21853 | TAAATGACACCCACATAAAT | 158 | | E8–E10 (soluble form 1) |
| 21854 | TAAATGACACCCACATAAAT | " | | 21853 |
| 21855 | TCGAAGGTTTCCACATAAAT | 159 | | E8–E11 (soluble form 2) |
| 21856 | TCGAAGGTTTCCACATAAAT | " | | 21855 |
| 21969 | CACCTGATTGTGTCTTGTCA | 109 | mismatch | 16949 |
| 21972 | CATCTGCTTCTGTATTGCCA | 104 | | 16949 |
| 22089 | TTACCTCATATTCAGTAACC | 148 | | 21764 |
| 22090 | GGTCCATAAATGACACCTGA | 147 | | 21763 |
| 22091 | TCACCCACATAAATAGGTTG | 146 | | 21762 |
| 22092 | CGATCAGTTTTTCCTTCTAA | 145 | | 21761 |
| 22093 | CTACACTCTGCAGATGAGTG | 144 | | 21760 |
| 22094 | GACTTCCTTTCCTTTCCTGG | 142 | | 21750 |
| 23232 | GCCATTCTATCAAGGACTTA | 149 | mismatch | 21752 |
| 23233 | GCCATGCTATCAAGCACTTC | 150 | " | " |
| 23234 | GCTATCCTATCAAGCACGTC | 151 | " | " |

[1]Emboldened residues, 2'-methoxyethoxy-residues (others are 2'-deoxy-), all "C" and "C" residues, 5-methyl-cytosines; all linkages are phosphorothioate linkages.
[2]Nucleotide number from Genbank Accession No. D90205, locus name "MUSIL5R" SEQ ID NO. 132.

These compounds were tested at 10 μM dose for ability to reduce membrane or soluble IL-5 receptorα mRNA by RPA. Results for compounds tested are shown in Table 15.

TABLE 15

Activity of Mouse IL-5R Oligonucleotides against Soluble and Membrane IL-5 receptorα mRNA

| ISIS NO. | SEQ ID NO: | CHEM-ISTRY | % INHIB'N MEMBRANE IL-5 RECEPTOR | % INHIB'N SOLUBLE IL-5 RECEPTOR | TARGET REGION |
|---|---|---|---|---|---|
| 21847 | 155 | uniform 2'-MOE | 23 | 20 | E7–E8 (common) |
| 21848 | 155 | 2' MOE/ deoxy gapmer | 89 | 86 | 21847 |
| 21849 | 156 | uniform 2'-MOE | 70 | 5 | E8–E9 (membrane) |
| 21850 | 156 | 2' MOE/ deoxy gapmer | 39 | 25 | 21849 |
| 21851 | 157 | uniform 2'-MOE | 61 | 0 | E9–E10 (membrane) |
| 21852 | 157 | 2' MOE/ deoxy gapmer | 20 | 14 | 21851 |
| 21853 | 158 | uniform 2'-MOE | 14 | 45 | E8–E10 (soluble |

TABLE 15-continued

Activity of Mouse IL-5R Oligonucleotides against Soluble and Membrane IL-5 receptorα mRNA

| ISIS NO. | SEQ ID NO: | CHEM- ISTRY | % INHIB'N MEM- BRANE IL-5 RECEPTOR | % INHIB'N SOLUBLE IL-5 RECEPTOR | TARGET REGION |
|---|---|---|---|---|---|
| 21854 | 158 | 2' MOE/ deoxy gapmer | 11 | 14 | form 1) 21853 |
| 21855 | 159 | uniform 2'-MOE | 14 | 25 | E8–E11 (soluble form 2) |

As shown in Table 15, selective reduction of expression of the soluble form of IL-5 receptorα could be achieved with antisense oligonucleotides targeted to the exon 8-exon 10 boundary, or, to a lesser extent to the exon 8-exon 11 boundary, both of which junctions are only found in the soluble receptor mRNA. Selective reduction of expression of the membrane form of IL-5 receptorα could be achieved with antisense oligonucleotides targeted to the exon 8-exon 9 boundary or exon 9-exon 10 boundary, both of which are only present in the mRNA targeting the membrane form of IL-5 receptorα. Placement of the fully-2' MOE oligonucleotides across the intron/exon boundaries of exon 9 resulted in similar effects as were obtained with fully-modified oligonucleotides positioned inside exon 9.

Example 27
Effect of Antisense Oligonucleotides on Expression of Membrane Form of IL-5 receptorα Protein in Murine $BCL_1$ Cells $BCL_1$ cells were treated with antisense oligonucleotide for 48 hours. Oligonucleotides used were ISIS 16949 ("common" oligonucleotide targeted to both soluble and membrane forms of IL-5 receptor), ISIS 21752, targeted only to the membrane form and ISIS 21853 and 21855, targeted only to the soluble forms of IL-5 receptorα. Oligonucleotides were introduced by electroporation as described in previous examples. Effect on levels of the membrane form of the receptor was examined by Western blot analysis. Membrane-enriched fractions were prepared as Triton X-100 insoluble material and separated by SDS-PAGE using 8% gels. Antibody to mouse IL-5 receptorα was purchased from Santa Cruz Biotechnology (Santa Cruz, Calif.) and used at 1:1000 dilution.

Compared to control (no oligonucleotide), ISIS 21752 nearly completely ablated the membrane IL-5 receptor. ISIS 21853 and 21855 together had little to no effect; both target the soluble receptor isoforms specifically. The common sequence oligonucleotide, ISIS 16949, reduced the soluble receptor by 75%.

Transfection with a fully 2'-MOE oligonucleotide targeted to the 5' intron splice site for either exon 8, 9 or 10 resulted in specific exclusion of that particular downstream exon but not others adjacent or upstream. Thus targeting the 5' intron splice sites with high-affinity antisense compounds such as fully 2'-MOE oligonucleotides allows selective deletion of individual exons of the mRNA transcript.

Example 28
Reduction of Eosinophils in Blood and Peritoneal Lavage Fluid of Mice Treated with IL-5 Receptorα Antisense Oligonucleotide Mice received daily injections of recombinant mouse IL-5 for 5 days, with or without ISIS 21972 or its mismatch control, ISIS 21969. Percent eosinophils in blood and peritoneal lavage fluid were measured. In control mice (no IL-5, no oligonucleotide) eosinophil levels were 4% in peritoneal lavage fluid and 2% in blood. After IL-5 treatment, eosinophils increased to 13.5% in lavage fluid and 9.5% in blood. Treatment with mismatch oligonucleotide did not change this significantly (13.5% in lavage fluid, 10.5% in blood) but treatment with IL-5 receptorα antisense oligonucleotide reduced eosinophil levels to 8.5% in peritoneal lavage fluid and 7% in blood.

HUMAN IL-5 RECEPTOR

Example 29
Antisense Oligonucleotides Targeted to Human IL-5 receptorα

The human IL-5 receptorα gene contains 14 exons. A membrane-anchored form of the receptor and two soluble forms have been identified. The membrane form is active in signal transduction and the soluble forms can act antagonistically. The mRNA transcript encoding the membrane-anchored form of the human IL-5 receptorα contain exons 1–10 and 12–14. Exon 11 is spliced out by an alternative splicing event. The major soluble isoform (soluble form 1) is generated as a result of a normal splicing event and an in-frame stop codon in exon 11. The other soluble form (soluble form 2) is generated by the absence of splicing and therefore is generated by reading into intron 11.

mRNA transcripts encoding the membrane form of the human IL-5 receptorα contain exons 1–10 and 12–14. Exon 11 is spliced out. It is, therefore, possible to target sequences in exons 1–10 which are common to both soluble and membrane forms of the receptor, or to selectively target sequences only present in the membrane form (exons 12–14). A series of antisense oligonucleotides were designed to be specific to only the membrane form of human IL-5 receptorα (IL-5Rα). These oligonucleotides target regions downstream of exon 11 (i.e., exons 12–14 and intervening introns, stop codon and 3' untranslated region). Tavernier et al., *Proc. Natl. Acad. Sci.*, 1992, 89, 7041–7045.

These are shown in Table 16.

TABLE 16

Nucleotide Sequences of Human IL-5 receptorα (membrane-specific antisense oligonucleotides

| ISIS NO. | NUCLEOTIDE SEQUENCE (5' -> 3') | SEQ ID NO: | TARGET SITE[2] | TARGET REGION |
|---|---|---|---|---|
| 16767 | AACCACTCTCTCAAGGGCTT | 160 | 1070–1089 | Coding |
| 16768 | TGCTGGAATTGGTGGAAACA | 161 | 1173–1192 | Coding |
| 17769 | GTCTCAACTCCAGGCTTCTC | 162 | 1283–1302 | Coding |
| 16770 | TCAAAACACAGAATCCTCCA | 163 | 1305–1324 | STOP |
| 16771 | AGGATGCCAAAGTGACAGTC | 164 | 1323–1342 | STOP |
| 16772 | ATCCCTGTTCTTTTCACTGA | 165 | 1371–1390 | 3'-UTR |
| 16773 | CGCAGGTAAATTGAGTGTTG | 166 | 1426–1445 | 3'-UTR |
| 16774 | TGAGGCGATTTGGATGAAGC | 167 | 1495–1514 | 3'-UTR |
| 16775 | TGGACGTTAGCCTTAAAAGC | 168 | 1651–1670 | 3'-UTR |
| 16776 | AGCTTAAACAGCCAAACGGG | 169 | 1693–1712 | 3'-UTR |
| 16777 | CTCCAGGCTGATGCAAAATG | 170 | 1751–1770 | 3'-UTR |
| 16778 | GGGTGAGGAATTTGTGGCTC | 171 | 1817–1836 | 3'-UTR |
| 16779 | CTGGATCAGGCCTCTGGAGC | 172 | 1936–1955 | 3'-UTR |
| 18012 | GGGTGAGGATTTTGTGGCTC | 173 | mismatch | 16778 |
| 18013 | GGGTGATGATTTGGTGGCTC | 174 | " | " |
| 18014 | GGCTGATGATTTGGTGGGTC | 175 | " | " |

[1]Emboldened residues, 2'-methoxyethoxy-residues (others are 2'-deoxy-) including "C" residues, 5-methyl-cytosines; all linkages are phosphorothioate linkages.
[2]Nucleotide numbers from Genbank Accession No. X61176, locus name "HSIL5RG", SEQ ID NO. 176, to which oligonucleotides are targeted.

These cells were tested in an IL-5 receptor-expressing subclone of TF-1 cells (provided by Dr. Christoph Walker, Novartis Research Centre, Horsham, UK. Cells were cultured in RPMI 1640 medium supplemented with 10% heat-inactivated fetal bovine serum (Sigma Chemical Company, St.Louis, Mo.), 10 mM Hepes, pH 7.2, 50 μM 2-ME, 2 mM L-glutamine, 100 U/ml penicillin, 100 μg/ml streptomycin (Gibco, Grand Island, N.Y.) and 10 ng/ml recombinant human IL-5 (R & D Systems, Minneapolis, Minn.) added every 48–72 hours. TF-1 cells (1×10[7] cells in PBS) were transfected with oligonucleotides by electroporation at 250V, 1000 μF using a BTX ElectroCell Manipulator 600 (Genetronics, San Diego Calif.).

Total cellular RNA was isolated using the RNeasy™ kit (Qiagen, Santa Clarita Calif.). Northern blotting was performed using standard methods using a full-length cDNA probe or a cDNA probe corresponding to the membrane isoform-specific exon sequences prepared from HL-60 cell RNA by standard RT-PCR followed by a nested primer reaction. Signals were quantitated using a Molecular Dynamics PhosphorImager. Results are shown in Table 17.

TABLE 17

Activity of Human IL-5 receptorα membrane-specific antisense oligonucleotides on IL-5 receptor mRNA expression

| ISIS NO. | % control membrane IL-5 Rα | % inhib membrane IL-5 Rα | % control soluble IL-5 Rα | % inhib soluble IL-5 Rα | SEQ ID NO: |
|---|---|---|---|---|---|
| 16767 | 86 | 14 | 95 | 5 | 160 |
| 16768 | 72 | 28 | 97 | 3 | 161 |
| 16769 | 48 | 52 | 100 | 0 | 162 |
| 16770 | 69 | 31 | 84 | 16 | 163 |
| 16771 | 66 | 34 | 78 | 22 | 164 |
| 16772 | 66 | 34 | 92 | 8 | 165 |
| 16773 | 48 | 52 | 84 | 16 | 166 |
| 16774 | 55 | 45 | 103 | — | 167 |
| 16775 | 100 | 0 | 95 | 5 | 168 |
| 16776 | 59 | 41 | 81 | 19 | 169 |
| 16777 | 31 | 69 | 84 | 16 | 170 |
| 16778 | 41 | 59 | 92 | 8 | 171 |
| 16779 | 55 | 45 | 95 | 5 | 172 |

ISIS 16769, 16773, 16774, 16776, 16777, 16778 and 16779 inhibited the membrane form of IL-5 receptorα by at least 40% and are preferred. Of these, ISIS 16769, 16774, 16778 and 16779 are more preferred because of their minimal effect on the soluble form of IL-5Rα.

The effect of ISIS 16778 on expression of human IL-5 receptorα protein on the surface of TF-1 cells was measured by flow cytometry. Following electroporation with oligonucleotide, TF-1 cells were incubated for 24 hours or as indicated, collected by centrifugation and washed with cold PBS. Cells were transferred to 12×75 mm polystyrene tubes and washed in 2% bovine serum albumin, 0.2% sodium azide in PBS at 4° C. Cells were centrifuged at 200×g and the supernatant was decanted. Specific antibody was then added at 1:100 for human IL-5 receptorα-phycoerythrin and the isotype control antibody in 0.1 mL of the above buffer. Antibodies were incubated with the cells for 30 minutes at 4° C. in the dark with gentle agitation. Cells were then washed as above and resuspended in 0.3 mL of FacsFlow buffer (Becton Dickinson, Franklin Lakes, N.J.) with 0.5% formaldehyde. Cells were analyzed on a Becton-Dickinson FACScan. Results are expressed as the percentage of control expression based on mean fluorescence intensity, subtracting basal expression.

In dose-response experiments to determine the effect of this oligonucleotide on human IL-5 receptorα cell surface protein expression in TF-1 cells, ISIS 16778 demonstrated an IC50 of approximately 5 μM. A 1-mismatch control had an IC50 of 7.5 μM and 3- and 5-mismatch controls did not inhibit IL-5 receptorα below 75% of control.

An additional set of oligonucleotides was designed to target both membrane and soluble forms of human IL-5 receptor. These oligonucleotides, targeted to exons 1–10 and intervening introns, are sometimes referred to as "common" IL-5 receptor oligonucleotides. Sequences are shown in Table 18.

have an IC50 of approximately 2 μM for reduction of IL-5 receptorα cell surface protein in TF-1 cells. A 1-mismatch control had an IC50 of approximately 3 μM and 3- and 5-mismatch controls did not inhibit IL-5 receptorα expression below 75% of control.

TABLE 18

Human IL-5R "Common" Antisense Oligonucleotides

| ISIS NO. | NUCLEOTIDE SEQUENCE (5' -> 3') | SEQ ID NO: | TARGET SITE[2] | TARGET REGION |
|---|---|---|---|---|
| 16780 | CCTGAGAAATGCGGTGGCCA | 177 | 0019–0038 | 5'-UTR |
| 16781 | GTGTCTATGCTCGTGGCTGC | 178 | 0093–0112 | 5'-UTR |
| 16782 | CGATCCTCTTGTTCCGACCA | 179 | 0148–0167 | 5'-UTR |
| 16783 | ATGCGCCACGATGATCATAT | 180 | 0248–0267 | AUG |
| 16784 | GCAGTATCTCAGTGGCCCCC | 181 | 0285–0304 | Coding |
| 16785 | TGCTCTTGATCAGGATTTGG | 182 | 0403–0422 | Coding |
| 16786 | CAGGATGGTCCGCACACTTG | 183 | 0536–0555 | Coding |
| 16787 | GGGCATGAAGTTCAGCAGAA | 184 | 0591–0610 | Coding |
| 16788 | GCCAGGTGCAGTGAAGGGAA | 185 | 0702–0721 | Coding |
| 16789 | CTCCCCAGTGTGTCTTTGCT | 186 | 0805–0824 | Coding |
| 16790 | AAGCCAGTCACGCCCTTTGC | 187 | 0863–0882 | Coding |
| 16791 | AAACAGCTGATCAAAGGGCC | 188 | 0923–0942 | Coding |
| 16792 | ATGGATTGGAAAAGCAGACA | 189 | 1034–1053 | Coding |
| 16793 | TCTGCACATGGAGCTCACTG | 190 | 1181–1200 | Coding |
| 16794 | AGGTTGGCTCCACTCACTCC | 191 | 1214–1233 | Coding |
| 18015 | TCTGCACATGTAGCTCACTG | 192 | mismatch | 16793 |
| 18016 | TCTGCACGTGTAACTCACTG | 193 | " | " |
| 18017 | TATGCACGTGTAACTCCCTG | 194 | " | " |

[1]Emboldened residues, 2'-methoxyethoxy-residues (others are 2'-deoxy-) including "C" residues, 5-methyl-cytosines; all linkages are phosphorothioate linkages.
[1]Nucleotide numbers from Genbank Accession No. M96652, locus name "HUMIL5RB", SEQ ID NO. 195, to which oligonucleotides are targeted. Note: these sequences are also common to GenBank accession nos. M96651 and X61176.

TABLE 19

Activity of Human IL-5 receptorα "Common" antisense oligonucleotides on IL-5 receptor mRNA expression

| ISIS NO. | % control membrane IL-5 Rα | % inhib'n membrane IL-5 Rα | % control soluble IL-5 Rα | % inhib'n soluble IL-5 Rα | SEQ ID NO: |
|---|---|---|---|---|---|
| 16780 | 86 | 14 | 84 | 16 | 177 |
| 16781 | 42 | 58 | 39 | 61 | 178 |
| 16782 | 41 | 59 | 39 | 61 | 179 |
| 16783 | 49 | 51 | 47 | 53 | 180 |
| 16784 | 92 | 8 | 89 | 11 | 181 |
| 16785 | 19 | 81 | 32 | 68 | 182 |
| 16786 | 14 | 86 | 13 | 87 | 183 |
| 16787 | 49 | 51 | 47 | 53 | 184 |
| 16788 | 22 | 78 | 21 | 79 | 185 |
| 16789 | 14 | 86 | 12 | 88 | 186 |
| 16790 | 22 | 78 | 21 | 79 | 187 |
| 16791 | 46 | 54 | 45 | 55 | 188 |
| 16792 | 35 | 65 | 34 | 66 | 189 |
| 16793 | 14 | 86 | 13 | 87 | 190 |
| 16794 | 38 | 62 | 37 | 63 | 191 |

In this assay, ISIS 16781, 16782, 16783, 16785, 16786, 16787, 16788, 16789, 16790, 16791, 16792, 16793 and 16794 inhibited both membrane and soluble IL-5 receptorα isoforms by greater than 50% and are preferred. Of these, ISIS 16786, 16788, 16789, 16790 and 16793 inhibited both isoforms by greater than 75%.

ISIS 16793 was chosen for further study. It totally inhibited expression of both soluble and membrane forms of human IL-5 receptorα mRNA. This compound was found to Example 30

Antisense Oligonucleotides Targeted to Splice Sites in the Human IL-5 Receptorα mRNA The human IL-5 receptorα gene contains 14 exons. A membrane-anchored form of the receptor and two soluble forms have been identified. As with the mouse receptor, the membrane form is active in signal transduction and the soluble forms are not, and can act antagonistically. The mRNA transcript encoding the membrane-anchored form of the human IL-5 receptorα contain exons 1–10 and 12–14. Exon 11 is spliced out by an alternative splicing event. The major soluble isoform (soluble form 1) is generated as a result of a normal splicing event and an in-frame stop codon in exon 11. The other soluble form (soluble form 2) is generated by the absence of splicing and therefore is generated by reading into intron 11.

Transcripts encoding soluble forms of human IL-5 receptorα do not contain exons 12, 13 or 14. It is, therefore, possible to target sequences in exons 1–10 which are common to both soluble and membrane forms of the receptor, or to selectively target sequences only present in the membrane form (exons 12–14). Oligonucleotides were also designed to target various intron/exon boundaries downstream of exon 11, with the intention of preventing successful splicing downstream of exon 11 and thus redirecting splice products away from the membrane form and in favor of the soluble form of IL-5 receptorα. A series of oligonucleotides were designed to target various splice sites or (intron-exon boundaries) in the IL-5 receptor mRNA. These are shown in Table 20 and their effect on IL-5 receptor mRNA and cell surface protein levels is shown in Tables 21 and 22.

TABLE 20

Nucleotide Sequences of Human IL-5R Oligonucleotides

| ISIS NO. | NUCLEOTIDE SEQUENCE (5' -> 3') | SEQ ID NO: | TARGET REGION[2] |
|---|---|---|---|
| 16746 | ACCCAGCTTTCTGCAAAACA | 196 | I13/E14 |
| 16747 | ACCCAGCTTTCTGCAAAACA | " | |
| 16748 | ACCCAGCTTTCTGCAAAACA | " | |
| 16749 | TCAACATTACCTCATAGTTA | 197 | E13/I13 |
| 16750 | TCAACATTACCTCATAGTTA | " | |
| 16751 | TCAACATTACCTCATAGTTA | " | |
| 16752 | TAAATGACATCTGAAAACAG | 198 | I12/E13 |
| 16753 | TAAATGACATCTGAAAACAG | " | |
| 16754 | TAAATGACATCTGAAAACAG | " | |
| 16755 | GAACACTTACATTTTACAGA | 199 | E12/I12 |
| 16756 | GAACACTTACATTTTACAGA | " | |
| 16757 | GAACACTTACATTTTACAGA | " | |
| 16758 | TCATCATTTCCTGGTGGAAA | 200 | I11/E12 |
| 16759 | TCATCATTTCCTGGTGGAAA | " | |
| 16760 | TCATCATTTCCTGGTGGAAA | " | |
| 18009 | TCATCATTTACTGGTGGAAA | 201 | mismatch |
| 18010 | TCAGCATTTACTGGTGTAAA | 202 | mismatch |
| 18011 | TCAGCAGTTACTTGTGTAAA | 203 | mismatch |

[1]Emboldened residues, 2'-methoxyethoxy- residues (others are 2'-deoxy-) including "C" residues, 5-methyl-cytosines; all linkages are phosphorothioate linkages.
[2]Target regions refer to intron/exon junctions (splice sites) to which oligonucleotides are targeted. I13/E14 indicates the junction between the 3' end of intron 13 and the 5' end of exon 14. E13/I13 indicates the junction between the 3' end of exon 13 and the 5' end of intron 13. I12/E13 indicates the junction between the 3' end of intron 12 and the 5' end of exon 13. E12/I12 indicates the junction between the 3' end of exon 12 and the 5' end of intron 12.
I11/E12 indicates the junction between the 3' end of intron 11 and the 5' end of exon 12.
Target sequences are from FIG. 2 of Tuypens, T., et al., Eur. Cytokine Netw., 1992), 3, 451–459.

TABLE 21

Modulation of Human IL-5 receptorα membrane form mRNA expression by Splice Site Oligonucleotides (18 hr)

| IRIS NO. | SEQ ID NO: | TARGET REGION | % of CONTROL | % INHIB'N |
|---|---|---|---|---|
| 16746 | 196 | I13/E14 | 36% | 64% |
| 16747 | " | | 66 | 34 |
| 16748 | " | | 25 | 75 |
| 16749 | 197 | E13/I13 | 101 | — |
| 16750 | " | | 96 | 4 |
| 16751 | " | | 96 | 4 |
| 16752 | 198 | I12/E13 | 101 | — |
| 16753 | " | | 98 | 2 |
| 16754 | " | | 101 | — |
| 16755 | 199 | E12/I12 | 15.5 | 84 |
| 16756 | " | | 96 | 4 |
| 16757 | " | | 91 | 9 |
| 16758 | 200 | I11/E12 | 176 | — |
| 16759 | " | | 81 | 19 |
| 16760 | " | | 76 | 24 |

[1]Emboldened residues, 2'-methoxyethoxy- residues (others are 2'-deoxy-) including "C" residues, 5-methyl-cytosines; all linkages are phosphorothioate linkages.

ISIs 16746, 16748 and 16755 inhibited IL-5 membrane receptor mRNA expression by over 50% and are therefore preferred in this assay. Northern blot analysis indicated that ISIS 16755 inhibited the membrane receptor transcript without significantly inhibiting the soluble form. Thus it is believed that ISIS 16755 redirects splicing in favor of the membrane form, as is consistent with data obtained with other non-RNAse H (e.g., uniform 2'-methoxyethoxy) oligonucleotides targeted to splice sites.

TABLE 22

Modulation of Human IL-5 receptorα protein expression on the Cell Surface by Splice Site Oligonucleotides (36 hr)

| ISIS NO. | NUCLEOTIDE SEQUENCE (5' -> 3') | SEQ ID NO: | TARGET REGION[2] | % of CONTROL | % INHIB |
|---|---|---|---|---|---|
| 16746 | ACCCAGCTTTCTGCAAAACA | 196 | I13/E14 | 35 | 65% |
| 16747 | ACCCAGCTTTCTGCAAAACA | " | | 80.5 | 19.5 |
| 16748 | ACCCAGCTTTCTGCAAAACA | " | | 40.5 | 59.5 |
| 16749 | TCAACATTACCTCATAGTTA | 197 | E13/I13 | 75 | 25 |
| 16750 | TCAACATTACCTCATAGTTA | " | | 91 | 9 |
| 16751 | TCAACATTACCTCATAGTTA | " | | 101 | — |
| 16752 | TAAATGACATCTGAAAACAG | 198 | I12/E13 | 100.5 | — |
| 16753 | TAAATGACATCTGAAAACAG | " | | 96 | 4 |
| 16754 | TAAATGACATCTGAAAACAG | " | | 100.5 | — |
| 16755 | GAACACTTACATTTTACAGA | 199 | E12/I12 | 10.5 | 89.5 |
| 16756 | GAACACTTACATTTTACAGA | " | | 101 | — |
| 16757 | GAACACTTACATTTTACAGA | " | | 81 | 19 |
| 16758 | TCATCATTTCCTGGTGGAAA | 200 | I11/E12 | 5.5 | 94.5 |
| 16759 | TCATCATTTCCTGGTGGAAA | " | | 75.5 | 24.5 |
| 16760 | TCATCATTTCCTGGTGGAAA | " | | 71 | 29 |

[1]Emboldened residues, 2'-methoxyethoxy- residues (others are 2'-deoxy-) including "C" residues, 5-methyl-cytosines; all linkages are phosphorothioate linkages.
[2]Target regions refer to intron/exon junctions (splice sites) to which oligonucleotides are targeted. I13/E14 indicates the junction between the 3' end of intron 13 and the 5' end of exon 14. E13/I13 indicates the junction between the 3' end of exon 13 and the 5' end of intron 13. I12/E13 indicates the junction between the 3' end of intron 12 and the 5' end of exon 13. E12/I12 indicates the junction between the 3' end of exon 12 and the 5' end of intron 12. I11/E12 indicates the junction between the 3' end of intron 11 and the 5' end of exon 12.

ISIS 16746, 16748, 16755 and 16758 inhibited human IL-5 receptorα protein by over 50% in this assay and are therefore preferred. ISIS 16758 and 16755 were chosen for further study. ISIS 16758 was found to have an IC50 of approximately 5 μM for reduction of IL-5 receptorα cell surface protein in TF-1 cells. A 1-mismatch control had an IC50 of 10 μM and 3- and 5-mismatch controls did not inhibit IL-5 receptorα expression. ISIS 16758 inhibited IL-5 receptorα protein expression without reducing mRNA levels, consistent with an RNAse H-independent mechanism as predicted for a uniformly 2'-methoxyethoxy modified oligonucleotide.

Example 31
Induction of Apoptosis in TF-1 Cells Treated with IL-5 Receptorα Oligonucleotide $1 \times 10^6$ TF-1 cells cultured in IL-5 (0.5 ng/ml) were collected 48 hours following oligonucleotide treatment (transfection was by electroporation as described in previous examples) and phosphatidylserine expression was detected as a measure of apoptosis using the Annexin-V flow cytometry kit (Clontech, Palo Alto, Calif.) according to the manufacturer's instructions. Briefly, cells were resuspended in 0.2 ml of staining buffer (10 mM Hepes, pH 7.4, 140 mM NaCl, 5 mM $CaCl_2$) and 10 μM of propidium iodide (50 μg/ml) and 5 μl of Annexin V reagent were added at 4° C. for 10 minutes. The samples were diluted with FacsFlow (Becton Dickinson, Franklin Lakes N.J.) buffer and analyzed on a Becton Dickinson FACScan. Results are shown in Table 23.

TABLE 23

Apoptosis induction mediated by antisense to human IL-5 receptorα

| ISIS No. | Chemistry | Oligo dose (μM) | % Apoptotic cells | SEQ ID NO: |
|---|---|---|---|---|
| No oligo | | | 14 | |
| 16793 | 2'-MOE gapmer "common" sequence | 5 | 19.8 | 190 |
| " | | 10 | 49.2 | " |
| " | | 15 | 62.3 | " |
| 18017 | 5-mismatch for 16793 | 5 | 20.5 | 194 |
| " | | 10 | 17.5 | " |
| " | | 15 | 20.3 | " |
| 16758 | Uniform 2'-MOE | 10 | 33.1 | 200 |
| " | | 15 | 40.1 | " |
| " | | 20 | 50.4 | " |
| 18011 | 5-mismatch for 16758 | 10 | 19 | 203 |
| " | | 15 | 23.6 | " |
| " | | 20 | 21.8 | " |
| 16778 | 2'-MOE gapmer Membrane-specific | 7.5 | 29.9 | 171 |
| " | | 12.5 | 49.2 | " |
| 18014 | 5-mismatch for 16778 | 7.5 | 38 | 175 |
| " | | 12.5 | 32.2 | " |

Apoptosis was shown to be induced in TF-1 cells cultured in the presence of IL-5 by antisense oligonucleotide inhibitors of IL-5 receptorα.

Example 32

Effect of IL-5 Receptor Oligonucleotides on Cell Proliferation $2.5 \times 10^4$ TF-1 cells were incubated in 96-well plates in 200 μl complete RPMI in the absence of IL-5 for 16 hours following electroporation. IL-5 (0.5 ng/ml) was added and the cultures were pulsed with 1 μCi of [$^3$H]-thymidine for the last 8 hours of a 48-hour culture period. The cells were harvested on glass fiber filters and analyzed for thymidine incorporation (proportional to cell proliferation) by liquid scintillation counting.

Results are shown in Table 24. Results are compared to thymidine incorporation in untreated controls.

TABLE 24

Inhibition of IL-5-induced TF-1 cell proliferation by human IL-5 receptorα antisense oligonucleotides

| ISIS No. | Chemistry | Oligo dose (μM) | % of control thymidine incorporation | SEQ ID NO: |
|---|---|---|---|---|
| 16793 | 2'-MOE gapmer "common" sequence | 5 | 44.5 | 190 |
| " | | 10 | 11.1 | " |
| 18017 | 5-mismatch for 16793 | 5 | 89.1 | 194 |
| " | | 10 | 92.8 | " |
| 16758 | Uniform 2'-MOE | 10 | 42.8 | 200 |
| " | | 15 | 39.2 | " |
| " | | 20 | 19.9 | " |
| 18011 | 5-mismatch for 16758 | 10 | 95.6 | 203 |
| " | | 15 | 97.9 | " |
| " | | 20 | 84.6 | " |

These data demonstrate that antisense inhibitors of IL-5 receptorα greatly reduce cellular response to IL-5, i.e., cell proliferation in response to IL-5. Control oligonucleotides were ineffective.

Example 33

Oligonucleotides Targeted to Human IL-5 Receptorα

Oligonucleotides were designed to target the 5' untranslated region of the IL-5 receptorα. These are shown in Table 25. Both 2'-methoxyethoxy gapmers and uniform 2'-methoxyethoxy compounds were designed.

TABLE 25

Nucleotide Sequences of Human IL-5R Oligonucleotides

| ISIS NO. | NUCLEOTIDE SEQUENCE (5' -> 3') | SEQ ID NO: | TARGET SITE[2] | TARGET REGION |
|---|---|---|---|---|
| 16963 | AGCGGCAGAGCATTGAGAAC | 204 | 0562–0581 | 5'-UTR |
| 16964 | AGCGGCAGAGCATTGAGAAC | 205 | " | " |
| 16965 | GAAGCAGCGGCAGAGCATTG | 206 | 0567–0586 | 5'-UTR |
| 16966 | GAAGCAGCGGCAGAGCATTG | 207 | " | " |

[1]Emboldened residues, 2'-methoxyethoxy- residues (others are 2'-deoxy-) including "C" residues, 5-methyl-cytosines; all linkages are phosphorothioate linkages.
[1]Nucleotide numbers are from Genbank Accession No. U18373, locus name "HSU18373", SEQ ID NO. 208 to which oligonucleotides are targeted.

Example 34

Mixed backbone oligonucleotides were designed to target human IL-5 receptorα. These are shown in Table 26.

TABLE 26

Mixed Backbone Nucleotide Analogues of Human IL-5R Oligonucleotides

| ISIS NO. | NUCLEOTIDE SEQUENCE (5' -> 3") | BACKBONE CHEMISTRY | SEQ ID NO: | TARGET REGION |
|---|---|---|---|---|
| 18018 | TCATCATTTCCTGGTGGAAA | P=S | 200 | 16758 |
| 18019 | TCATCATTTCCTGGTGGAAA | P=O | " | " |
| 18020 | GGGTGAGGAATTTGTGGCTC | P=S | 171 | 16778 |
| 18021 | GGGTGAGGAATTTGTGGCTC | P=O/P=S | " | " |
| 18022 | TCTGCACATGGAGCTCACTG | P=S | 190 | 16793 |
| 18023 | TCTGCACATGGAGCTCACTG | P=O/P=S | " | " |

[1]Emboldened residues, 2'-methoxyethoxy- residues (others are 2'-deoxy-) including "C" residues, 5-methyl-cytosines; P=O/P=S indicates phosphodiester linkages in the 2'-MOE regions and phosphorothioate linkages in the 2'-deoxy gap

Example 35
Optimization of Human IL-5 Receptorα Oligonucleotides

A series of antisense oligonucleotides were designed based on active sequences, with various placements of 2' methoxyethoxy regions. These are shown in Table 27.

TABLE 27

Nucleotide Analogues of Human IL-5R Oligonucleotides

| ISIS NO. | NUCLEOTIDE SEQUENCE (5' -> 3') | SEQ ID NO: | TARGET REGION |
|---|---|---|---|
| 18024 | AGCTTAAACAGCCAAACGGG | 169 | 16776 |
| 18025 | AGCTTAAACAGCCAAACGGG | " | " |
| 18026 | AGCTTAAACAGCCAAACGGG | " | " |
| 18027 | AGCTTAAACAGCCAAACGGG | " | " |
| 18028 | AGCTTAAACAGCCAAACGGG | " | " |
| 18029 | AGCTTAAACAGCCAAACGGG | " | " |
| 18030 | CGCAGGTAAATTGAGTGTTG | 166 | 16773 |
| 18031 | CGCAGGTAAATTGAGTGTTG | " | " |
| 18032 | CGCAGGTAAATTGAGTGTTG | " | " |
| 18033 | CGCAGGTAAATTGAGTGTTG | " | " |
| 18034 | CGCAGGTAAATTGAGTGTTG | " | " |
| 18035 | CGCAGGTAAATTGAGTGTTG | " | " |
| 18036 | GGGTGAGGAATTTGTGGCTC | 172 | 16778 |
| 18037 | GGGTGAGGAATTTGTGGCTC | " | " |
| 18038 | GGGTGAGGAATTTGTGGCTC | " | " |
| 18039 | GGGTGAGGAATTTGTGGCTC | " | " |
| 18040 | GGGTGAGGAATTTGTGGCTC | " | " |
| 18041 | GGGTGAGGAATTTGTGGCTC | " | " |
| 18042 | AAGCCAGTCACGCCCTTTGC | 187 | 16790 |
| 18043 | AAGCCAGTCACGCCCTTTGC | " | " |
| 18044 | AAGCCAGTCACGCCCTTTGC | " | " |
| 18045 | AAGCCAGTCACGCCCTTTGC | " | " |
| 18046 | AAGCCAGTCACGCCCTTTGC | " | " |
| 18047 | AAGCCAGTCACGCCCTTTGC | " | " |

TABLE 27-continued

Nucleotide Analogues of Human IL-5R Oligonucleotides

| ISIS NO. | NUCLEOTIDE SEQUENCE (5' -> 3') | SEQ ID NO: | TARGET REGION |
|---|---|---|---|
| 18048 | CAGGATGGTCCGCACACTTG | 183 | 16786 |
| 18049 | CAGGATGGTCCGCACACTTG | " | " |
| 18050 | CAGGATGGTCCGCACACTTG | " | " |
| 18051 | CAGGATGGTCCGCACACTTG | " | " |
| 18052 | CAGGATGGTCCGCACACTTG | " | " |
| 18053 | CAGGATGGTCCGCACACTTG | " | " |
| 18054 | TCTGCACATGGAGCTCACTG | 190 | 16793 |
| 18055 | TCTGCACATGGAGCTCACTG | " | " |
| 18056 | TCTGCACATGGAGCTCACTG | " | " |
| 18057 | TCTGCACATGGAGCTCACTG | " | " |
| 18058 | TCTGCACATGGAGCTCACTG | " | " |
| 18059 | TCTGCACATGGAGCTCACTG | " | " |
| 18060 | GAACACTTACATTTTACAGA | 199 | 16755 |
| 18061 | GAACACTTACATTTTACAGA | " | " |
| 18062 | GAACACTTACATTTTACAGA | " | " |
| 18063 | GAACACTTACATTTACAGA | " | " |
| 18064 | TCATCATTTCCTGGTGGAAA | 200 | 16758 |
| 18065 | TCATCATTTCCTGGTGGAAA | " | " |
| 18066 | TCATCATTCCTGGTGGAAA | " | " |
| 18067 | TCATCATTTCCTGGTGGAAA | " | " |

[1]Emboldened residues, 2'-methoxyethoxy- residues (others are 2'-deoxy-) including "C" residues, 5-methyl-cytosines; all linkages are phosphorothioate linkages.

What is claimed is:

1. An antisense compound 8 to 30 nucleobases in length which is targeted to a 5'-untranslated region, a 3'-untranslated region or a stop codon of a murine or human nucleic acid molecule encoding interleukin-5 and wherein said antisense compound modulates the expression of interleukin-5.

2. The antisense compound of claim 1 which is an antisense oligonucleotide.

3. An antisense compound up to 30 nucleobases in length comprising at least an 8-nucleobase portion of SEQ ID NO: 53 which inhibits the expression of human interleukin-5.

4. An antisense compound up to 30 nucleobases in length comprising at least an 8-nucleobase portion of SEQ ID NO: 162, 166, 167, 169, 170, 171 or 172 which inhibits the expression of human interleukin-5 receptorα.

5. The antisense compound of claim 2 wherein the antisense oligonucleotide comprises at least one modified internucleoside linkage.

6. The antisense compound of claim 5 wherein the modified internucleoside linkage of the antisense oligonucleotide is a phosphorothioate linkage.

7. The antisense compound of claim 2 wherein the antisense oligonucleotide comprises at least one modified sugar moiety.

8. The antisense compound of claim 7 wherein the modified sugar moiety of the antisense oligonucleotide is a 2'-O-methoxyethyl sugar moiety.

9. The antisense compound of claim 8 wherein substantially all sugar moieties of the antisense oligonucleotide are 2'-O-methoxyethyl sugar moieties.

10. The antisense compound of claim 2 wherein the antisense oligonucleotide comprises at least one modified nucleobase.

11. The antisense compound of claim 10 wherein the modified nucleobase of the antisense oligonucleotide is a 5-methylcytosine.

12. The antisense compound of claim 8 wherein each 2'-O-methoxyethyl modified cytosine nucleobase of the antisense oligonucleotide is a 5-methylcytosine.

13. The antisense compound of claim 1 which is a chimeric oligonucleotide.

14. A composition comprising the antisense compound of claim 1 and a pharmaceutically acceptable carrier or diluent.

15. The composition of claim 14 further comprising a colloidal dispersion system.

16. The composition of claim 14 wherein the antisense compound is an antisense oligonucleotide.

17. An antisense compound 8 to 30 nucleobases in length which is targeted to a nucleic acid molecule encoding a human soluble interleukin-5 receptorα and which preferentially inhibits the expression of human soluble interleukin-5 receptorα.

18. The antisense compound of claim 17 which is targeted to a region of a nucleic acid molecule encoding soluble interleukin-5 receptorα which is not found in a nucleic acid molecule encoding membrane interleukin-5 receptorα.

19. An antisense compound 8 to 30 nucleobases in length which is targeted to a nucleic acid molecule encoding a human membrane interleukin-5 receptorα and which preferentially inhibits the expression of human membrane interleukin-5 receptorα.

20. The antisense compound of claim 19 which is targeted to a region of a nucleic acid molecule encoding membrane interleukin-5 receptorα which is not found in a nucleic acid molecule encoding soluble interleukin-5 receptorα.

21. An antisense compound 8 to 30 nucleobases in length which is targeted to exon 9 of a nucleic acid molecule encoding a murine interleukin-5 receptorα and which inhibits the expression of both soluble and membrane forms of murine interleukin-5 receptorα.

22. An antisense compound 8 to 30 nucleobases in length which is targeted to a nucleic acid molecule encoding a human interleukin-5 receptorα and which alters the ratio of human interleukin-5 receptorα isoforms expressed by a cell or tissue.

23. The antisense compound of claim 22 which increases the ratio of the soluble form of interleukin-5 receptorα to the membrane form of interleukin-5 receptorα expressed.

24. The antisense compound of claim 23 which is an antisense oligonucleotide wherein substantially all sugar moieties of the antisense oligonucleotide are 2'-O-methoxyethyl sugar moieties.

25. An antisense compound 8 to 30 nucleobases in length which is targeted to a nucleic acid molecule encoding a human or murine interleukin-5 receptorα and which alters the splicing of an RNA encoding human or murine interleukin-5 receptorα, such that the ratio of interleukin-5 receptorα isoforms is altered.

26. A method of modulating interleukin-5 signal transduction in cells or tissues comprising contacting said cells or tissues in vitro with the antisense compound of claim 1 so that the interleukin-5 signal transduction is modulated.

27. A method of inhibiting the expression of human interleukin-5 in human cells or tissues comprising contacting said cells or tissues in vitro with the antisense compound of claim 1 so that expression of human interleukin-5 is inhibited.

28. A method of inhibiting the expression of human interleukin-5 receptorα in human cells or tissues comprising contacting said cells or tissues in vitro with the antisense compound of claim 6 so that expression of human interleukin-5 receptorα is inhibited.

29. A method of altering the ratio of the isoforms of human interleukin-5 receptorα in human cells or tissues comprising contacting said cells or tissues in vitro with the antisense compound of claim 24 so that the ratio of the human interleukin-5 receptorα isoforms is altered.

30. The composition of claim 14 further comprising a chemotherapeutic agent for the treatment of asthma.

31. A composition comprising the antisense compound of claim 22 and a pharmaceutically acceptable carrier or diluent.

32. An antisense compound consisting of SEQ ID NO: 52 or 62 which inhibits the expression of human interleukin-5.

* * * * *

UNITED STATES PATENT AND TRADEMARK OFFICE
CERTIFICATE OF CORRECTION

PATENT NO. : 6,136,603
DATED : October 24, 2000
INVENTOR(S) : Dean et al.

It is certified that error appears in the above-identified patent and that said Letters Patent is hereby corrected as shown below:

Column 16,
Line 38, please "coichicine" and insert -- colchicine --.

Column 22,
Line 7, please delete "IM" and insert -- 1M --.

Column 28,
Table 3, column 2, please delete the nucleotide sequence of ISIS 17866 "AACTCCCTCGTCCTCCGTGT" and insert -- AACTGCCTCGTCCTCCGTGT --.
Table 3, column 2, please delete the nucleotide sequence of ISIS 17870 "CGTTATCCTTGGCTACATTA" and insert -- GGTTATCCTTGGCTACATTA --.
Table 3, column 2, please delete the nucleotide sequence of ISIS 17983 "GGTTATCCTAGGCTACATTA" and insert
-- GGTTATCCTAGGCTACATTA --.
Table 3, column 2, please delete the nucleotide sequence of ISIS 20394 "GGTTAACGTAGCCAACATTA" and insert -- GGTTAACGTAGCCAACATTA --.

Column 29,
Table 3, column 2, please delete the nucleotide sequence of ISIS 17984 "GGTTATCGTAGCCTACATTA" and insert -- GGTTATCGTAGCCTACATTA --.

Column 35,
Table 4, column 2, bolded residues of nucleotide sequences of ISIS NOs 16096 through 16103, should not be bolded.

Column 37,
Table 6, column 2, residues TTGCC of the nucleotide sequence of ISIS 16095 should be bolded.

Column. 38,
Table 7, column 2, the first five residues and last five residues of the nucleotide sequences of ISIS NO 21883, 22103, 23114, and 23115 should be bolded.

Column 42,
Table 10, column 2, the first five residues and last five residues of the nucleotide sequences of ISIS 18001, 18002, 18003, 18004, 18005, 18006, 18007, and 18008 should be bolded.

UNITED STATES PATENT AND TRADEMARK OFFICE
CERTIFICATE OF CORRECTION

PATENT NO. : 6,136,603
DATED : October 24, 2000
INVENTOR(S) : Dean et al.

It is certified that error appears in the above-identified patent and that said Letters Patent is hereby corrected as shown below:

Column 42, cont'd.,
Table 10, column 2, please delete the nucleotide sequence of ISIS 18006 "TGAGAACATTAACAAGACGA" and insert -- TGAGAAGATTAACAAGACGA --.
Table 10, column 2, please delete the nucleotide sequence of ISIS 18007 "TGCAGATGAGTCAGAAGATT" and insert -- TGCAGATGAGTGAGAAGATT --.

Column 43,
Table 12, column 2, residues of nucleotide sequences of ISIS NO 23235, 23236, 23237, 23238, 23239 and 23240 should all be emboldened.

Column 46,
Table 14, "E8-E10" in column 4 of row 7, should be in column 5 of row 7.

Column 49,
Table 16, column 2, the first five residues and last five residues of all nucleotide sequences in table should be bolded.

Column 51,
Table 18, column 2, the first five residues and last five residues of all nucleotide sequences in table should be bolded.

Column 140,
Line 13 in claim 28, please delete "claim 6 and insert -- claim 4 --.

Signed and Sealed this

Twenty-second Day of April, 2003

JAMES E. ROGAN
*Director of the United States Patent and Trademark Office*